US009744177B2

United States Patent
Labrie et al.

(10) Patent No.: US 9,744,177 B2
(45) Date of Patent: Aug. 29, 2017

(54) TREATMENT OF MALE ANDROGEN DEFICIENCY SYMPTOMS OR DISEASES WITH SEX STEROID PRECURSOR COMBINED WITH SERM

(71) Applicants: Fernand Labrie, Quebec (CA); Sylvain Gauthier, St-Augustin-de-Desmaures (CA)

(72) Inventors: Fernand Labrie, Quebec (CA); Sylvain Gauthier, St-Augustin-de-Desmaures (CA)

(73) Assignee: ENDORECHERCHE, INC. (CA)

( * ) Notice: Subject to any disclaimer, the term of this patent is extended or adjusted under 35 U.S.C. 154(b) by 0 days.

(21) Appl. No.: 14/638,763

(22) Filed: Mar. 4, 2015

(65) Prior Publication Data

US 2015/0250802 A1  Sep. 10, 2015

Related U.S. Application Data

(60) Provisional application No. 61/950,644, filed on Mar. 10, 2014.

(51) Int. Cl.
  *A61K 31/5685* (2006.01)
  *A61K 38/24* (2006.01)
  (Continued)

(52) U.S. Cl.
  CPC ........ *A61K 31/5685* (2013.01); *A61K 31/453* (2013.01); *A61K 38/24* (2013.01); *A61K 45/06* (2013.01)

(58) Field of Classification Search
  None
  See application file for complete search history.

(56) References Cited

U.S. PATENT DOCUMENTS 3,742,951 A  7/1973 Zaffaroni
3,797,444 A  3/1974 Stubbs
(Continued)

FOREIGN PATENT DOCUMENTS

CA  2 334 577 A1  12/1999
CA  2 376 158 A1  1/2001
(Continued)

OTHER PUBLICATIONS

Mayo Clinic, "Alzheimer's disease", Jun. 2014, retrieved from http://www.mayoclinic.org/diseases-conditions/alzheimers-disease/basics/definition/con-20023871.*
(Continued)

*Primary Examiner* — Jianfeng Song
(74) *Attorney, Agent, or Firm* — Ostrolenk Faber LLP

(57) ABSTRACT

Novel methods for prevention, reduction or elimination of the incidence of male androgen deficiency symptoms or diseases including male hypogonadism-associated symptoms and diseases associated with low serum testosterone and/or low DHEA or low total androgens in susceptible warm-blooded animals including humans involving administration of an amount of a sex steroid precursor, particularly dehydroepiandrosterone (DHEA) and a selective estrogen receptor modulator (SERM) (particularly acolbifene), an antiestrogen or a prodrug of the two. The symptoms or diseases are loss of libido, erectile dysfunction, tiredness, loss of energy, depression, bone loss, muscle loss, muscle weakness, fat accumulation, memory loss, cognition loss, Alzheimer's disease, dementia, loss of body hair, fertility problems, insomnia, gynecomastia, anemia, hot flushes, sweats, decreased sense of well-being, obesity, osteoporosis, hypercholesterolemia, hyperlipidemia, atherosclerosis, hypertension, insulin resistance, cardiovascular disease and type 2 diabetes. Pharmaceutical compositions for delivery of
(Continued)

active ingredient(s) and kit(s) useful to the invention are also disclosed.

39 Claims, 21 Drawing Sheets

(51) Int. Cl.
*A61K 31/453* (2006.01)
*A61K 45/06* (2006.01)

(56) References Cited

U.S. PATENT DOCUMENTS

| | | | |
|---|---|---|---|
| 4,568,343 A | 2/1986 | Leeper et al. | |
| 4,624,665 A | 11/1986 | Nuwayser | |
| 4,666,441 A | 5/1987 | Andriola et al. | |
| 5,064,654 A | 11/1991 | Berner et al. | |
| 5,071,644 A | 12/1991 | Viegas et al. | |
| 5,071,657 A | 12/1991 | Oloff et al. | |
| 5,135,480 A | 8/1992 | Bannon et al. | |
| 5,154,922 A | 10/1992 | Govil et al. | |
| 5,162,037 A | 11/1992 | Whitson-Fischman | |
| 5,861,391 A * | 1/1999 | Yen | A61K 31/5685 514/170 |
| 6,060,503 A | 5/2000 | Labrie et al. | |
| 6,107,331 A * | 8/2000 | MacLean | A61K 31/40 514/427 |
| 6,465,445 B1 | 10/2002 | Labrie | |
| 6,576,645 B1 * | 6/2003 | Sodervall | C07C 43/225 514/317 |
| 6,696,432 B1 * | 2/2004 | Elliesen | A61K 31/565 514/169 |
| 6,710,059 B1 | 3/2004 | Labrie et al. | |
| 2005/0233970 A1 * | 10/2005 | Garnick | A61K 31/55 514/10.2 |
| 2006/0293294 A1 | 12/2006 | Blom et al. | |
| 2007/0078091 A1 | 4/2007 | Hubler et al. | |
| 2009/0215733 A1 | 8/2009 | Scally | |
| 2011/0312925 A1 * | 12/2011 | Labrie | A61K 31/35 514/171 |

FOREIGN PATENT DOCUMENTS

| | | |
|---|---|---|
| CA | 2 395 730 A1 | 8/2001 |
| CA | 2 765 446 A1 | 12/2010 |
| CA | 2 802 761 A1 | 12/2011 |
| EP | 0 279 982 A1 | 8/1988 |
| EP | 0 802 183 A1 | 10/1997 |
| EP | 0 802 184 A1 | 10/1997 |
| GB | 2 185 187 A | 7/1987 |
| JP | H10-36347 | 2/1998 |
| WO | WO 97/25034 A1 | 7/1997 |
| WO | WO 97/25035 A1 | 7/1997 |
| WO | WO 97/25036 A1 | 7/1997 |
| WO | WO 97/25037 A1 | 7/1997 |
| WO | WO 97/25038 A1 | 7/1997 |
| WO | WO 97/32837 A1 | 9/1997 |
| WO | WO 01/91744 A1 | 12/2001 |
| WO | WO 03/072092 A1 | 9/2003 |
| WO | WO 2006/024689 A1 | 3/2006 |
| WO | WO 2013/123218 A1 | 8/2013 |
| WO | WO 2013/130832 A1 | 9/2013 |

OTHER PUBLICATIONS

Akaza, H. (2006). "Trends in primary androgen depletion therapy for patients with localized and locally advanced prostate cancer: Japanese perspective." *Cancer Sci* 97(4): 243-247.
Alexandersen, P., J. Haarbo, et al. (1996). "The relationship of natural androgens to coronary heart disease in males: a review." *Atherosclerosis* 125(1): 1-13.
Almeida, O. P., B. B. Yeap, et al. (2008). "Low free testosterone concentration as a potentially treatable cause of depressive symptoms in older men." *Arch Gen Psychiatry* 65(3): 283-289.
Amano, T., T. Imao, et al. (2010). "Testosterone replacement therapy by testosterone ointment relieves lower urinary tract symptoms in late onset hypogonadism patients". *Aging Male* 13(4): 242-246.
American Society of Andrology (2006). "Testosterone replacement therapy for male aging: ASA position statement." *J Androl* 27(2): 133-134.
Anker, S. D., T. P. Chua, et al. (1997). "Hormonal changes and catabolic/anabolic imbalance in chronic heart failure and their importance for cardiac cachexia." *Circulation* 96(2): 526-534.
Anker, S. D., A. L. Clark, et al. (1997). "Tumor necrosis factor and steroid metabolism in chronic heart failure: possible relation to muscle wasting." *J Am Coll Cardiol* 30(4): 997-1001.
Araujo, A. B. and G. A. Wittert (2011). "Endocrinology of the aging male." *Best Pract Res Clin Endocrinol Metab* 25(2): 303-319.
Arlt, W., F. Callies, et al. (1999). "Dehydroepiandrosterone replacement in women with adrenal insufficiency." *N. Engl. J. Med.* 341(14): 1013-1020.
Arlt, W., H. G. Justl, et al. (1998). "Oral dehydroepiandrosterone for adrenal androgen replacement: pharmacokinetics and peripheral conversion to androgens and estrogens in young healthy females after dexamethasone suppression." *J. Clin. Endocrinol. Metab.* 83(6): 1928-1934.
Azad, N., S. Pitale, et al. (2003). "Testosterone treatment enhances regional brain perfusion in hypogonadal men." *J Clin Endocrinol Metab* 88(7): 3064-3068.
Bachmann, G., J. Bancroft, et al. (2002). "Female androgen insufficiency: the Princeton consensus statement on definition, classification, and assessment." *Fertil Steril* 77(4): 660-665.
Baillargeon, J., R. J. Urban, et al. (2013). "Trends in androgen prescribing in the United States, 2001 to 2011." *JAMA Intern Med* 173(15): 1465-1466.
Barnhart, K. T., E. Freeman, et al. (1999). "The effect of dehydroepiandrosterone supplementation to symptomatic perimenopausal women on serum endocrine profiles, lipid parameters, and health-related quality of life." *J Clin Endocrinol Metab* 84(11): 3896-3902.
Barrett-Connor, E. and S. L. Edelstein (1994). "A prospective study of dehydroepiandrosterone sulfate and cognitive function in an older population: the Rancho Bernardo Study." *J Am Geriatr Soc* 42(4): 420-423.
Barrett-Connor, E., K. T. Khaw, et al. (1986). "A prospective study of dehydroepiandrosterone sulfate, mortality and cardiovascular disease." *N. Engl. J. Med.* 315(24): 1519-1524.
Basaria, S., A. D. Coviello, et al. (2010). "Adverse events associated with testosterone administration." *N Engl J Med* 363(2): 109-122.
Basaria, S., M. N. Davda, et al. (2013). "Risk factors associated with cardiovascular events during testosterone administration in older men with mobility limitation." *J Gerontol A Biol Sci Med Sci* 68(2): 153-160.
Bassil, N., S. Alkaade, et al. (2009). "The benefits and risks of testosterone replacement therapy: a review." *Ther Clin Risk Manag* 5(3): 427-448.
Basson, R. (2004). "A New Model of Female Sexual Desire." *Endocrine News* 29: 22.
Beck, S. G. and R. J. Handa (2004). "Dehydroepiandrosterone (DHEA): a misunderstood adrenal hormone and spine-tingling neurosteroid?" *Endocrinology* 145(3): 1039-1041.
Beer, N. A., D. J. Jakubowicz, et al. (1996). "Dehydroepiandrosterone reduces plasma plasminogen activator inhibitor type 1 and tissue plasminogen activator antigen in men." *Am J Med Sci* 311(5):205-210.
Behre, H. M., J. Bohmeyer, et al. (1994). "Prostate volume in testosterone-treated and untreated hypogonadal men in comparison to age-matched normal controls." *Clin Endocrinol (Oxf)* 40(3): 341-349.
Bélanger, A., M. Brochu, et al. (1986). "Levels of plasma steroid glucuronides in intact and castrated men with prostatic cancer." *J. Clin. Endocrinol. Metab.* 62: 812-815.
Bélanger, B., A. Bélanger, et al. (1989). "Comparison of residual C-19 steroids in plasma and prostatic tissue of human, rat and

(56) References Cited

OTHER PUBLICATIONS guinea pig after castration: unique importance of extratesticular androgens in men." *J. Steroid Biochem.* 32: 695-698.

Benz, D. J., M. R. Haussler, et al. (1991). "High-affinity androgen binding and androgenic regulation of a1(I)-procollagen and transforming growth factor-b steady state messenger ribonucleic acid levels in human osteoblast-like osteosarcoma cells." *Endocrinology* 128: 2723-2730.

Bhasin, S., G. R. Cunningham, et al. (2006). "Testosterone therapy in adult men with androgen deficiency syndromes: an endocrine society clinical practice guideline." *J Clin Endocrinol Metab* 91(6): 1995-2010.

Bhasin, S., G. R. Cunningham, et al. (2010). "Testosterone therapy in men with androgen deficiency syndromes: an Endocrine Society clinical practice guideline." *J Clin Endocrinol Metab* 95(6): 2536-2559.

Bhasin, S., T. W. Storer, et al. (1996). "The effects of supraphysiologic doses of testosterone on muscle size and strength in normal men." *N Engl J Med* 335(1): 1-7.

Bhasin, S., T. W. Storer, et al. (1997). "Testosterone replacement increases fat-free mass and muscle size in hypogonadal men." *J Clin Endocrinol Metab* 82(2): 407-413.

Bhasin, S., L. Woodhouse, et al. (2001). "Testosterone dose-response relationships in healthy young men." *Am J Physiol Endocrinol Metab* 281(6): E1172-1181.

Bhasin, S., L. Woodhouse, et al. (2005). "Older men are as responsive as young men to the anabolic effects of graded doses of testosterone on the skeletal muscle." *J Clin Endocrinol Metab* 90(2): 678-688.

Bolona, E. R., M. V. Uraga, et al. (2007). "Testosterone use in men with sexual dysfunction: a systematic review and meta-analysis of randomized placebo-controlled trials." *Mayo Clin Proc* 82(1): 20-28.

Bonnefoy, M., M. C. Patricot, et al. (2002). "[Relation between physical activity, muscle function and IGF-1, testosterone and DHEAS concentrations in the elderly]." *Rev Med Interne* 23(10): 819-827.

Bross, R., R. Casaburi, et al. (1998). "Androgen effects on body composition and muscle function: implications for the use of androgens as anabolic agents in sarcopenic states." *Baillieres Clin Endocrinol Metab* 12(3): 365-378.

Burger, H. G., J. Hailes, et al. (1984). "The management of persistent menopausal symptoms with oestradiol-testosterone implants: clinical, lipid and hormonal results." *Maturitas* 6: 351-358.

Callies, F., M. Fassnacht, et al. (2001). "Dehydroepiandrosterone replacement in women with adrenal insufficiency: effects on body composition, serum leptin, bone turnover, and exercise capacity." *J Clin Endocrinol Metab* 86(5): 1968-1972.

Calof, O. M., A. B. Singh, et al. (2005). "Adverse events associated with testosterone replacement in middle-aged and older men: a meta-analysis of randomized, placebo-controlled trials." *J Gerontol A Biol Sci Med Sci* 60(11): 1451-1457.

Coppola, A. R. (2013). "Testosterone therapy and risk of cardiovascular disease in men." *Jama* 310(17): 1805-1806.

Casson, P. R., R. N. Andersen, et al. (1993). "Oral dehydroepiandrosterone in physiologic doses modulates immune function in postmenopausal women." *Am. J. Obstet. Gynecol.* 169: 1536-1539.

Casson, P. R., N. Santoro, et al. (1998). "Postmenopausal dehydroepiandrosterone administration increases free insulin-like growth factor-I and decreases high-density lipoprotein: a six-month trial." *Fertil Steril* 70(1): 107-110.

Caubet, J. F., T. D. Tosteson, et al. (1997). "Maximum androgen blockade in advanced prostate cancer: a meta-analysis of published randomized controlled trials using nonsteroidal antiandrogens." *Urology* 49: 71-78.

Cefalu, W. T., Z. Q. Wang, et al. (1995). "Contribution of visceral fat mass to the insulin resistance of aging." *Metabolism* 44(7): 954-959.

Chang, D. M., J. L. Lan, et al. (2002). "Dehydroepiandrosterone treatment of women with mild-to-moderate systemic lupus erythematosus: a multicenter randomized, double-blind, placebo-controlled trial." *Arthritis Rheum* 46(11): 2924-2927.

Chang, J. T., S. C. Morton, et al. (2004). "Interventions for the prevention of falls in older adults: systematic review and meta-analysis of randomised clinical trials." *Bmj* 328(7441): 680.

Chen, S., J. Nilsen, et al. (2006). "Dose and temporal pattern of estrogen exposure determines neuroprotective outcome in hippocampal neurons: therapeutic implications." *Endocrinology* 147(11): 5303-5313.

Christopher-Hennings, J., I. D. Kurzman, et al. (1995). "The effect of high fat diet and dehydroepiandrosterone (DHEA) administration in the rhesus monkey." *In Vivo* 9(5): 415-420.

Cleary, M. P. and J. Zisk (1986). "Antiobesity effect of two different levels of dehydroepiandrosterone in lean and obese middle-aged female Zucker rats." *Int. J. Obes.* 10: 193-204.

Coleman, D. L., E. H. Leiter, et al. (1982). "Therapeutic effects of dehydroepiandrosterone (DHEA) in diabetic mice." *Diabetes* 31: 830-833.

Comhaire, F. H. (2000). "Andropause: hormone replacement therapy in the ageing male." *Eur Urol* 38(6): 655-662.

Corona, G., E. A. Jannini, et al. (2006). "Inventories for male and female sexual dysfunctions." *Int J Impot Res* 18(3): 236-250.

Corona, G., E. Mannucci, et al. (2006). "ANDROTEST: a structured interview for the screening of hypogonadism in patients with sexual dysfunction." *J Sex Med* 3(4): 706-715.

Corona, G., G. Rastrelli, et al. (2013). "Dehydroepiandrosterone supplementation in elderly men: a meta-analysis study of placebo-controlled trials." *J Clin Endocrinol Metab* 98(9): 3615-3626.

Corona, G., G. Rastrelli, et al. (2012). "Emerging medication for the treatment of male hypogonadism." *Expert Opin Emerg Drugs* 17(2): 239-259.

Couillard, S., C. Labrie, et al. (1998). "Effect of dehydroepiandrosterone and the antiestrogen EM-800 on the growth of human ZR-75-1 breast cancer xenografts." *J. Natl. Cancer Inst.* 90: 772-778.

Crawford, B. A., P. Y. Liu, et al. (2003). "Randomized placebo-controlled trial of androgen effects on muscle and bone in men requiring long-term systemic glucocorticoid treatment." *J Clin Endocrinol Metab* 88(7): 3167-3176

Cummings, S. R. and M. C. Nevitt (1989). "A hypothesis: the causes of hip fractures." *J Gerontol* 44(4): M107-111.

Cusan, L., A. Dupont, et al. (1994). "Comparison of flutamide and spironolactone in the treatment of hirsutism: a randomized controlled trial." *Fertil. Steril.* 61: 281-287.

Davis, S. R., P. McCloud, et al. (1995). "Testosterone enhances estradiol's effects on postmenopausal density and sexuality." *Maturitas* 21: 227-236.

Dennerstein, L., E. C. Dudley, et al. (1997). "Sexuality, hormones and the menopausal transition." *Maturitas* 26(2): 83-93.

Dhatariya, K., M. L. Bigelow, et al. (2005). "Effect of dehydroepiandrosterone replacement on insulin sensitivity and lipids in hypoadrenal women." *Diabetes* 54(3): 765-769.

Diamond, P., L. Cusan, et al. (1996). "Metabolic effects of 12-month percutaneous DHEA replacement therapy in postmenopausal women." *J. Endocrinol.* 150: S43-S50.

Ding, E. L., Y. Song, et al. (2006). "Sex differences of endogenous sex hormones and risk of type 2 diabetes: a systematic review and meta-analysis." *Jama* 295(11): 1288-1299.

Ebert, T., F. Jockenhovel, et al. (2005). "The current status of therapy for symptomatic late-onset hypogonadism with transdermal testosterone gel." *Eur Urol* 47(2): 137-146.

Eich, D. M., J. E. Nestler, et al. (1993). "Inhibition of accelerated coronary atherosclerosis with dehydroepiandrosterone in the heterotopic rabbit model of cardiac transplantation." *Circulation* 87(1): 261-269.

Elashoff, J. D., A. D. Jacknow, et al. (1991). "Effects of anabolic-androgenic steroids on muscular strength." *Ann Intern Med* 115(5): 387-393.

English, K. M., R. P. Steeds, et al. (2000). "Low-dose transdermal testosterone therapy improves angina threshold in men with chronic

(56) References Cited

OTHER PUBLICATIONS stable angina: A randomized, double-blind, placebo-controlled study." *Circulation* 102(16): 1906-1911.
Evans, W. (1997). "Functional and metabolic consequences of sarcopenia." *J Nutr* 127(5 Suppl): 998S-1003S.
Farhat, R., F. Al-zidjali, et al. (2010). "Outcome of gonadotropin therapy for male infertility due to hypogonadotrophic hypogonadism." *Pituitary* 13(2): 105-110.
Fernandez-Balsells, M. M., M. H. Murad, et al. (2010). "Clinical review 1: Adverse effects of testosterone therapy in adult men: a systematic review and meta-analysis." *J Clin Endocrinol Metab* 95(6): 2560-2575.
Ferrannini, E., A. Natali, et al. (1997). "Insulin resistance, hyperinsulinemia, and blood pressure: role of age and obesity. European Group for the Study of Insulin Resistance (EGIR)." *Hypertension* 30(5): 1144-1149.
Flood, J. F. and E. Roberts (1988). "Dehydroepiandrosterone sulfate improves memory in aging mice." *Brain Res* 448(1): 178-181.
Foy, M. R. (2001). "17beta-estradiol: effect on CA1 hippocampal synaptic plasticity." *Neurobiol Learn Mem* 76(3): 239-252.
Franchi F, Luisi M, et al. (1978). "Long-term study of oral testosterone undecanoate in hypogonadal males." *Int J Androl.* 1: 270-278.
Frontera, W. R., V. A. Hughes, et al. (2000). "Aging of skeletal muscle: a 12-yr longitudinal study." *J Appl Physiol* 88(4): 1321-1326.
Gallagher, A., T. J. Chambers, et al. (1993). "The estrogen antagonist ICI 182780 reduces cancellous bone volume in female rats." *Endocrinology* 133: 2787-2791.
Gauthier, S., B. Caron, et al. (1997). "(S)-(+)-4-[7-(2,2-dimethyl-1-oxopropoxy)-4-methyl-2-[4-[2-(1-piperidinyl)-ethoxy]phenyl]-2H-1-benzopyran-3-yl]-phenyl 2,2-dimethylpropanoate (EM-800): a highly potent, specific, and orally active nonsteroidal antiestrogen." *J. Med. Chem.* 40: 2117-2122.
Gebre-Medhin, G., E. S. Husebye, et al. (2000). "Oral dehydroepiandrosterone (DHEA) replacement therapy in women with Addison's disease." *Clin Endocrinol (Oxf)* 52(6): 775-780.
Genazzani, A. R., S. Inglese, et al. (2004). "Long-term low-dose dehydroepiandrosterone replacement therapy in aging males with partial androgen deficiency." *Aging Male* 7(2): 133-143.
Gibbs, R. B. and P. Aggarwal (1998). "Estrogen and basal forebrain cholinergic neurons: implications for brain aging and Alzheimer's disease-related cognitive decline." *Horm Behav* 34(2): 98-111.
Goldstat, R., E. Briganti, et al. (2003). "Transdermal testosterone therapy improves well-being, mood, and sexual function in pre-menopausal women." *Menopause* 10(5): 390-398.
Gooren, L. J. (1987). "Androgen levels and sex functions in testosterone-treated hypogonadal men." *Arch Sex Behav* 16(6): 463-473.
Gooren, L. J. (1994). "A ten-year safety study of the oral androgen testosterone undecanoate." *J Androl* 15(3): 212-215.
Gordon, C. M., E. Grace, et al. (2002). "Effects of oral dehydroepiandrosterone on bone density in young women with anorexia nervosa: a randomized trial." *J Clin Endocrinol Metab* 87(11): 4935-4941.
Gordon, G. B., D. E. Bush, et al. (1988). "Reduction of atherosclerosis by administration of dehydroepiandrosterone. A study in the hypercholesterolemic New Zealand white rabbit with aortic intimal injury." *J. Clin. Invest.* 82: 712-720.
Gordon, G. B., L. M. Shantz, et al. (1987). "Modulation of growth, differentiation and carcinogenesis by dehydroepiandrosterone." *Adv. Enzyme Regul.* 26: 355-382.
Gray, P. B., A. B. Singh, et al. (2005). "Dose-dependent effects of testosterone on sexual function, mood, and visuospatial cognition in older men." *J Clin Endocrinol Metab* 90(7): 3838-3846.
Grimley Evans, J., R. Malouf, et al. (2006). "Dehydroepiandrosterone (DHEA) supplementation for cognitive function in healthy elderly people." *Cochrane Database Syst Rev*(4): CD006221.
Guay, A. T., J. Jacobson, et al. (2003). "Clomiphene increases free testosterone levels in men with both secondary hypogonadism and erectile dysfunction: who does and does not benefit?" *Int J Impot Res* 15(3): 156-165.
Gurnell, E. M., P. J. Hunt, et al. (2008). "Long-term DHEA replacement in primary adrenal insufficiency: a randomized, controlled trial." *J Clin Endocrinol Metab* 93(2): 400-409.
Hackbert, L. and J. R. Heiman (2002). "Acute dehydroepiandrosterone (DHEA) effects on sexual arousal in post-menopausal women." *J Womens Health Gend Based Med* 11(2): 155-162.
Haddad, R. M., C. C. Kennedy, et al. (2007). "Testosterone and cardiovascular risk in men: a systematic review and meta-analysis of randomized placebo-controlled trials." *Mayo Clin Proc* 82(1): 29-39.
Haffner, S. M., R. S. Kushwaha, et al. (1983). "Studies on the metabolic mechanism of reduced high density lipoproteins during anabolic steroid therapy." *Metabolism* 32(4): 413-420.
Hajszan, T., N. J. MacLusky, et al. (2007). "Effects of androgens and estradiol on spine synapse formation in the prefrontal cortex of normal and testicular feminization mutant male rats." *Endocrinology* 148(5): 1963-1967.
Hak, A. E., J. C. Witteman, et al. (2002). "Low levels of endogenous androgens increase the risk of atherosclerosis in elderly men: the Rotterdam study." *J Clin Endocrinol Metab* 87(8): 3632-3639.
Hall, S. A., G. R. Esche, et al. (2008). "Correlates of low testosterone and symptomatic androgen deficiency in a population-based sample." *J Clin Endocrinol Metab* 93(10): 3870-3877.
Han, D. H., P. A. Hansen, et al. (1998). "DHEA treatment reduces fat accumulation and protects against insulin resistance in male rats." *J Gerontol A Biol Sci Med Sci* 53(1): B19-24.
Handelsman, D. J. (2006). "Clinical review: The rationale for banning human chorionic gonadotropin and estrogen blockers in sport." *J Clin Endocrinol Metab* 91(5): 1646-1653.
Hansen, P. A., D. H. Han, et al. (1997). "DHEA protects against visceral obesity and muscle insulin resistance in rats fed a high-fat diet." *Am J Physiol* 273(5 Pt 2): R1704-1708.
Harman, S. M., E. J. Metter, et al. (2001). "Longitudinal effects of aging on serum total and free testosterone levels in healthy men. Baltimore Longitudinal Study of Aging." *J Clin Endocrinol Metab* 86(2): 724-731.
Hayashi, T., T. Esaki, et al. (2000). "Dehydroepiandrosterone retards atherosclerosis formation through its conversion to estrogen: the possible role of nitric oxide." *Arterioscler Thromb Vasc Biol* 20(3): 782-792.
Hazzard, W. R., S. M. Haffner, et al. (1984). "Preliminary report: kinetic studies on the modulation of high-density lipoprotein, apolipoprotein, and subfraction metabolism by sex steroids in a postmenopausal woman." *Metabolism* 33(9): 779-784.
Henderson, E., J. Y. Yang, et al. (1992). "Dehydroepiandrosterone (DHEA) and sysnthetic DHEA analogs are modest inhibitors of HIV-1 IIIB replication." *Aids Res. Hum. Retroviruses* 8: 625-631.
Hennernan, P. M. and S. Wallach (1957). "The role of androgens and estrogens and their metabolic effects. A review of the prolonged use of estrogens and androgens in postmenopausal and senile osteoporosis." *AMA: Arch. Int. Med.* 100: 715-723.
Herrington, D. M., G. B. Gordon, et al. (1990). "Plasma dehydroepiandrosterone and dehydroepiandrosterone sulfate in patients undergoing diagnostic coronary angiography." *J. Am. Coll. Cardiol.* 16: 862-870.
Herrington, D. M., N. Nanjee, et al. (1996). "Dehydroepiandrosterone and cardiac allograft vasculopathy." *J Heart Lung Transplant* 15(1 Pt 1): 88-93.
Hogervorst, E., S. Bandelow, et al. (2004). "Low free testosterone is an independent risk factor for Alzheimer's disease." *Exp Gerontol* 39(11-12): 1633-1639.
Hogervorst, E., J. Williams, et al. (2000). "The nature of the effect of female gonadal hormone replacement therapy on cognitive function in post-menopausal women: a meta-analysis." *Neuroscience* 101(3): 485-512.
Holland, J., S. Bandelow, et al. (2011). "Testosterone levels and cognition in elderly men: a review." *Maturitas* 69(4): 322-337.

(56) References Cited

OTHER PUBLICATIONS

Holmang, S., P. Marin, et al. (1993). "Effect of long-term oral testosterone undecanoate treatment on prostate volume and serum prostate-specific antigen concentration in eugonadal middle-aged men." *Prostate* 23(2): 99-106.
Huang, J., H. Guan, et al. (2004). "Estrogen regulates neprilysin activity in rat brain." *Neurosci Lett* 367(1): 85-87.
Huggins, C. and C. V. Hodges (1941). "Studies of prostatic cancer. I. Effect of castration, estrogen and androgen injections on serum phosphatases in metastatic carcinoma of the prostate." *Cancer Res.* 1: 293-307.
Hughes, V. A., W. R. Frontera, et al. (2002). "Longitudinal changes in body composition in older men and women: role of body weight change and physical activity." *Am J Clin Nutr* 76(2): 473-481.
Hunt, P. J., E. M. Gurnell, et al. (2000). "Improvement in mood and fatigue after dehydroepiandrosterone replacement in Addison's disease in a randomized, double blind trial." *J Clin Endocrinol Metab* 85(12): 4650-4656.
Huppert, F. A. and J. K. Van Niekerk (2001). "Dehydroepiandrosterone (DHEA) supplementation for cognitive function." *Cochrane Database Syst Rev* 2(2): CD 000304.
Iannuzzi-Sucich, M., K. M. Prestwood, et al. (2002). "Prevalence of sarcopenia and predictors of skeletal muscle mass in healthy, older men and women." *J Gerontol A Biol Sci Med Sci* 57(12): M772-777.
Isidori, A. M., M. Caprio, et al. (1999). "Leptin and androgens in male obesity: evidence for leptin contribution to reduced androgen levels." *J Clin Endocrinol Metab* 84(10): 3673-3680.
Isidori, A. M., E. Giannetta, et al. (2005). "Effects of testosterone on body composition, bone metabolism and serum lipid profile in middle-aged men: a meta-analysis." *Clin Endocrinol (Oxf)* 63(3): 280-293.
Johannsson, G., P. Burman, et al. (2002). "Low dose dehydroepiandrosterone affects behavior in hypopituitary androgen-deficient women: a placebo-controlled trial." *J Clin Endocrinol Metab* 87(5): 2046-2052.
Jones, T. H., S. Arver, et al. (2011). "Testosterone replacement in hypogonadal men with type 2 diabetes and/or metabolic syndrome (the TIMES2 study)." *Diabetes Care* 34(4): 828-837.
Jones, T. H. and F. Saad (2009). "The effects of testosterone on risk factors for, and the mediators of, the atherosclerotic process." *Atherosclerosis* 207(2): 318-327.
Jordan, V. C., E. Phelps, et al. (1987). "Effects of antiestrogens on bone in castrated and intact female rats." *Breast Cancer Res. Treat.* 10: 31-35.
Kallman, D. A., C. C. Plato, et al. (1990). "The role of muscle loss in the age-related decline of grip strength: cross-sectional and longitudinal perspectives." *J Gerontol* 45(3): M82-88.
Kantor, M. A., A. Bianchini, et al. (1985). "Androgens reduce HDL2-cholesterol and increase hepatic triglyceride lipase activity." *Med Sci Sports Exerc* 17(4): 462-465.
Kapoor, D., E. Goodwin, et al. (2006). "Testosterone replacement therapy improves insulin resistance, glycaemic control, visceral adiposity and hypercholesterolaemia in hypogonadal men with type 2 diabetes." *Eur J Endocrinol* 154(6): 899-906.
Kapoor, D., C. J. Malkin, et al. (2005). "Androgens, insulin resistance and vascular disease in men." *Clin Endocrinol (Oxf)* 63(3): 239-250.
Kapur, S. P. and A. H. Reddi (1989). "Influence of testosterone and dihydrotestosterone on bone-matrix induced endochondral bone formation." *Calcif. Tissue Int.* 44: 108-113.
Katz, D. J., O. Nabulsi, et al. (2011). "Outcomes of clomiphene citrate treatment in young hypogonadal men." *BJU Int* 110(4): 573-578.
Kawano, H., H. Yasue, et al. (2003). "Dehydroepiandrosterone supplementation improves endothelial function and insulin sensitivity in men." *J Clin Endocrinol Metab* 88(7): 3190-3195.
Kelleher, S., A. J. Conway, et al. (2004). "Blood testosterone threshold for androgen deficiency symptoms." *J Clin Endocrinol Metab* 89(8): 3813-3817.

Kenny, A. M., K M. Prestwood, in older men with low 272. et al. (2001). "Effects of transdermal testosterone on bone and muscle bioavailable testosterone levels." *J Gerontol A Biol Sci Med Sci* 56(5): M266-272.
Khaw, K T., M. Dowsett, et al (2007). "Endogenous testosterone and mortality due to all causes, cardiovascular disease, and cancer in men: European prospective investigation into cancer in Norfolk (EPIC-Norfolk) Prospective Population Study." *Circulation* 116(23): 2694-2701.
Kim, E. D., L. Crosnoe, et al. (2013). "The treatment of hypogonadism in men of reproductive age." *Fertil Steril* 99(3): 718-724.
Kleerekoper, M., A. R. Villanueva, et al. (1985). "The role of three-dimensional trabecular microstructure in the pathogenesis of vertebral compression fractures." *Calcif. Tissue Int.* 37: 594-597.
Komesaroff, P. A. (2008). "Unravelling the enigma of dehydroepiandrosterone: moving forward step by step." *Endocrinology* 149(3): 886-888.
Kopelman, P. G. (2000). "Obesity as a medical problem." *Nature* 404(6778): 635-643.
Kostka, T., L. M. Arsac, et al. (2000). "Leg extensor power and dehydroepiandrosterone sulfate, insulin-like growth factor-I and testosterone in healthy active elderly people." *Eur J Appl Physiol* 82(1-2): 83-90.
Kramer, C. Y. (1956). "Extension of multiple range tests to group means with unique numbers of replications." *Biometrics* 12: 307-310.
Koller, C. and P. Buri (1987). "Propriétés et intérêt pharmaceutique des gels thermoréversibles á base de poloxamers et poloxamines." *S. T. P. Pharma* 3(2): 115-124.
Kurzman, I. D., D. L. Panciera, et al. (1998). "The effect of dehydroepiandrosterone combined with a low-fat diet in spontaneously obese dogs: a clinical trial." *Obes Res* 6(1): 20-28.
Kushnir, M. M., T. Blamires, et al. (2010). "Liquid chromatography-tandem mass spectrometry assay for androstenedione, dehydroepiandrosterone, and testosterone with pediatric and adult reference intervals." *Clin Chem* 56(7): 1138-1147.
Labrie, C., A. Bélanger, et al. (1988). "Androgenic activity of dehydroepiandrosterone and androstenedione in the rat ventral prostate." *Endocrinology* 123: 1412-1417.
Labrie, F. (1991). "Intracrinology." *Mol. Cell. Endocrinol.* 78: C113-C118.
Labrie, F. (2010a). "DHEA after Menopause—Sole source of sex steroids and potential sex steroid deficiency treatment." *Menopause Management* 19: 14-24.
Labrie, F. (2010b). DHEA, important source of sex steroids in men and even more in women. *Neuroendocrinology, The Normal Neuroendocrine System, Progress in Brain Research.* L. Martini, Chrousos G.P, Labrie F, Pacak K and D. Pfaff, eds., Elsevier. 182 (Chapter 4): 97-148.
Labrie, F. (2011). "Blockade of testicular and adrenal androgens in prostate cancer treatment." *Nat Rev. Urol* 8(2): 73-85.
Labrie, F., D. Archer, et al. (2009a). "Effect on intravaginal dehydroepiandrosterone (Prasterone) on libido and sexual dysfunction in postmenopausal women." *Menopause* 16: 923-931.
Labrie, F., D. Archer, et al. (2009b). "Intravaginal dehydroepiandrosterone (Prasterone), a physiological and highly efficient treatment of vaginal atrophy." *Menopause* 16: 907-922.
Labrie, F., D. Archer, et al. (2009c). "Serum steroid levels during 12-week intravaginal dehydroepiandrosterone administration." *Menopause* 16: 897-906.
Labrie, F., A. Bélanger, et al. (2006). "Androgen glucuronides, instead of testosterone, as the new markers of androgenic activity in women." *J Steroid Biochem Mol Biol* 99: 182-188.
Labrie, F., A. Bélanger, et al. (1997a). "Physiological changes in dehydroepiandrosterone are not reflected by serum levels of active androgens and estrogens but of their metabolites: intracrinology." *J Clin Endocrinol Metab* 82(8): 2403-2409.
Labrie, F., A. Bélanger, et al. (1997b). "Marked decline in serum concentrations of adrenal C19 sex steroid precursors and conjugated androgen metabolites during aging." *J Clin Endocrinol Metab* 82: 2396-2402.

(56) References Cited

OTHER PUBLICATIONS

Labrie, F., A. Bélanger, et al. (1993). "Science behind total androgen blockade: from gene to combination therapy." Clin. Invest. Med. 16: 475-492.
Labrie, F., A. Belanger, et al. (1998). "DHEA and the intracrine formation of androgens and estrogens in peripheral target tissues: its role during aging." Steroids 63(5-6): 322-328.
Labrie, F., A. Bélanger, et al. (2005). "Gonadotropin-releasing hormone agonists in the treatment of prostate cancer." Endocrine Reviews 26(3): 361-379.
Labrie, F., B. Candas, et al. (2002). "Can combined androgen blockade provide long-term control or possible cure of localized prostate cancer?" Urology 60(1): 115-119.
Labrie, F., L. Cusan, et al. (2009). "Comparable amounts of sex steroids are made outside the gonads in men and women: strong lesson for hormone therapy of prostate and breast cancer." J Steroid Biochem Mol Biol 113: 52-56.
Labrie, F., P. Diamond, et al. (1997a). "Effect of 12-month DHEA replacement therapy on bone, vagina, and endometrium in postmenopausal women." J. Clin. Endocrinol. Metab. 82: 3498-3505.
Labrie, F., A. Dupont, et al. (1985). Complete androgen blockade for the treatment of prostate cancer. Important Advances in Oncology. V. T. de Vita, S. Hellman and S. A. Rosenberg. Philadelphia, J.B. Lippincott: 193-217.
Labrie, F., A. Dupont, et al. (1982). "New hormonal therapy in prostatic carcinoma: combined treatment with an LHRH agonist and an antiandrogen." Clin. Invest. Med. 5: 267-275.
Labrie, F., V. Luu-The, et al. (1997). "The key role of 17b-HSDs in sex steroid biology." Steroids 62: 148-158.
Labrie, F., C. Martel, et al. (2011). "Wide distribution of the serum dehydroepiandrosterone and sex steroid levels in postmenopausal women: role of the ovary?" Menopause 18(1): 30-43.
Labrie, F., J. Simard, et al. (1992a). "Structure, function and tissue-specific gene expression of 3b-hydroxysteroid dehydrogenase/5-ene-4-ene isomerase enzymes in classical and peripheral intracrine steroidogenic tissues." J. Steroid Biochem. Mol. Biol. 43: 805-826.
Labrie, F., J. Simard, et al. (1996a). The 3β-hydroxysteroid dehydrogenase/isomerase gene family: lessons from type II 3β-HSD congenital deficiency. Signal Transduction in Testicular Cells. Ernst Schering Research Foundation Workshop. V. Hansson, F. O. Levy and K. TaskZn. Berlin, Heidelberg, New York, Springer-Verlag. Suppl. 2: 185-218.
Labrie, F., J. Simard, et al. (1992b). "Structure and tissue-specific expression of 3b-hydroxysteroid dehydrogenase/5-ene-4-ene isomerase genes in human and rat classical and peripheral steroidogenic tissues." J. Steroid Biochem. Mol. Biol. 41: 421-435.
Labrie, F., J. Simard, et al. (1994). "Structure, regulation and role of 3b-hydroxysteroid dehydrogenase, 17b-hydroxysteroid dehydrogenase and aromatase enzymes in formation of sex steroids in classical and peripheral intracrine tissues." Hormone, Enzymes and Receptors: 451-474.
Labrie, F., Y. Sugimoto, et al. (1992). "Structure of human type II 5α-reductase." Endocrinology 131: 1571-1573.
Labrie, Y., F. Durocher, et al. (1995). "The human type II 17β-hydroxysteroid dehydrogenase gene encodes two alternatively-spliced messenger RNA species." DNA Cell Biol. 14: 849-861.
Lamberts, S. W. (2003). "The endocrinology of gonadal involution: menopause and andropause." Ann Endocrinol (Paris) 64(2): 77-81.
Larsson, L., G. Grimby, et al. (1979). "Muscle strength and speed of movement in relation to age and muscle morphology." J Appl Physiol 46(3): 451-456.
Lasco, A., N. Frisina, et al. (2001). "Metabolic effects of dehydroepiandrosterone replacement therapy in postmenopausal women." Eur J Endocrinol 145: 457-461.
Lauffenburger, T., A. J. Olah, et al. (1977). "Bone remodeling and calcium metabolism: a correlated histomorphometric, calcium kinetic, and biochemical study in patients with osteoporosis and Paget's disease." Metabolism 26: 589-606.
Laumann, E. O., A. Paik, et al. (1999). "Sexual dysfunction in the United States: prevalence and predictors." Jama 281(6): 537-5/11.
LeBlanc, E. S., J. Janowsky, et al. (2001). "Hormone replacement therapy and cognition: systematic review and meta-analysis." Jama 285(11): 1489-1499.
Li, S., X. Yan, et al. (1993). "Prevention by dehydroepiandrosterone of the development of mammary carcinoma induced by 7,12-dimethylbenz(a)anthracene (DMBA) in the rat." Breast Cancer Res. Treat. 29: 203-217.
Libe, R., L. Barbetta, et al. (2004). "Effects of dehydroepiandrosterone (DHEA) supplementation on hormonal, metabolic and behavioral status in patients with hypoadrenalism." J Endocrinol Invest 27(8): 736-741.
Liu, P. Y., H. W. Baker, et al. (2009). "Induction of spermatogenesis and fertility during gonadotropin treatment of gonadotropin-deficient infertile men: predictors of fertility outcome." J Clin Endocrinol Metab 94(3): 801-808.
Liu, P. Y., R. S. Swerdloff, et al. (2006). "Rate, extent, and modifiers of spermatogenic recovery after hormonal male contraception: an integrated analysis." Lancet 367(9520): 1412-1420.
Lobo, R. A. (1991). "Clinical review 27: Effects of hormonal replacement on lipids and lipoproteins in postmenopausal women." J. Clin. Endocrinol. Metab. 73(5): 925-930.
Lobo, R. A., R. C. Rosen, et al. (2003). "Comparative effects of oral esterified estrogens with and without methyltestosterone on endocrine profiles and dimensions of sexual function in postmenopausal women with hypoactive sexual desire." Fertil Steril 79(6): 1341-1352.
Lovas, K., G. Gebre-Medhin, et al. (2003). "Replacement of dehydroepiandrosterone in adrenal failure: no benefit for subjective health status and sexuality in a 9-month, randomized, parallel group clinical trial." J Clin Endocrinol Metab 88(3): 1112-1118.
Lovas, K. and E. S. Husebye (2008). "Replacement therapy for Addison's disease: recent developments." Expert Opin Investig Drugs 17(4): 497-509.
Lunenfeld, B. and E. Nieschlag (2007). "Testosterone therapy in the aging male." Aging Male 10(3): 139-153.
Luo, S., A. Sourla, et al. (1997). "Combined effects of dehydroepiandrosterone and EM-800 on bone mass, serum lipids, and the development of dimethylbenz(a)anthracene (DMBA)-induced mammary carcinoma in the rat." Endocrinology 138: 4435-4444.
Luu-The, V., I. Dufort, et al. (1995). "Structural characterization and expression of the human dehydroepiandrosterone sulfotransferase gene." DNA Cell Biol. 14: 511-518.
Luu-The, V., Y. Zhang, et al. (1995). "Characteristics of human types 1, 2 and 3 17b-hydroxysteroid dehydrogenase activities: oxidation-reduction and inhibition." J. Steroid Biochem. Mol. Biol. 55: 581-587.
MacEwen, E. G. and I. D. Kurzman (1991). "Obesity in the dog: role of the adrenal steroid dehydroepiandrosterone (DHEA)." J. Nutr. 121: S51-S55.
Maggi, M., J. Buvat, et al. (2013). "Hormonal causes of male sexual dysfunctions and their management (hyperprolactinemia, thyroid disorders, GH disorders, and DHEA)." J Sex Med 10(3): 661-677.
Malkin, C. J., P. J. Pugh, et al. (2004). "Testosterone replacement in hypogonadal men with angina improves ischaemic threshold and quality of life." Heart 90(8): 871-876.
Malkin, C. J., P. J. Pugh, et al. (2006). "Testosterone therapy in men with moderate severity heart failure: a double-blind randomized placebo controlled trial." Eur Heart J 3 27(1): 57-64.
Manson, J. E., S. S. Bassuk, et al. (2006). "Postmenopausal hormone therapy: new questions and the case for new clinical trials." Menopause 13(1): 139-147.
Marin, P., S. Holmang, et al. (1993). "Androgen treatment of abdominally obese women." Obes. Res. 1: 245-251.
Marks, L. S., N. A. Mazer, et al. (2006). "Effect of testosterone replacement therapy on prostate tissue in men with late-onset hypogonadism: a randomized controlled trial." Jama 296(19): 2351-2361.
Martel, C., A. Sourla, et al. (1998). "Predominant androgenic component in the stimulatory effect of dehydroepiandrosterone on bone mineral density in the rat." J. Endocrinol. 157: 433-442.

(56) References Cited

OTHER PUBLICATIONS

Matsumoto, A. M. (2002). "Andropause: clinical implications of the decline in serum testosterone levels with aging in men." *J Gerontol A Biol Sci Med Sci* 57(2): M76-99.

McEwen, B. S. and S. E. Alves (1999). "Estrogen actions in the central nervous system." *Endocr Rev* 20(3): 279-307.

McEwen, B. S., E. Gould, et al. (1995). "Oestrogens and the structural and functional plasticity of neurons: implications for memory, ageing and neurodegenerative processes." *Ciba Found Symp* 191: 52-66; discussion 66-73.

Melsen, F., B. Melsen, et al. (1978). "Histomorphometric analysis of normal bone from the iliac crest." *Acta Pathol. Microbiol. Scand.* 86: 70-81.

Melton, L. J., 3rd, S. Khosla, et al. (2000). "Epidemiology of sarcopenia." *Mayo Clin Proc* 75 Suppl: S10-12; discussion S12-13.

Meunier, P. J., C. Salson, et al. (1987). "Skeletal distribution and biochemical parameters of Paget's disease." *Clin. Orthop.* 217: 37-44.

Miller, K. K., W. Rosner, et al. (2004). "Measurement of free testosterone in normal women and women with androgen deficiency: comparison of methods." *J Clin Endocrinol Metab* 89(2): 525-533.

Mitchell, L. E., D. L. Sprecher, et al. (1994). "Evidence for an association between dehydroepiandrosterone sulfate and nonfatal, premature myocardial infarction in males." *Circulation* 89(1): 89-93.

Mohan, P. F., J. S. Ihnen, et al. (1990). "Effects of dehydroepiandrosterone treatment in rats with diet-induced obesity." *J. Nutr.* 120: 1103-1114.

Monk, D. and H. Brodaty (2000). "Use of estrogens for the prevention and treatment of Alzheimer's disease." *Dement Geriatr Cogn Disord* 11(1): 1-10.

Moore, C., D. Huebler, et al. (2004). "The Aging Males' Symptoms scale (AMS) as outcome measure for treatment of androgen deficiency." *Eur Urol* 46(1): 80-87.

Morales, A. J., R. H. Haubrich, et al. (1998). "The effect of six months treatment with a 100 mg daily dose of dehydroepiandrosterone (DHEA) on circulating sex steroids, body composition and muscle strength in age-advanced men and women." *Clin Endocrinol (Oxf)* 49(4): 421-432.

Morales, A. J., J. J. Nolan, et al. (1994). "Effects of replacement dose of dehydroepiandrosterone in men and women of advancing age." *J. Clin. Endocrinol. Metab.* 78: 1360-1367.

Morley, J. E. (2003). "Testosterone and behavior." *Clin Geriatr Med* 19(3): 605-616.

Morley, J. E., E. Charlton, et al. (2000). "Validation of a screening questionnaire for androgen deficiency in aging males." *Metabolism* 49(9): 1239-1242.

Morley, J. E. and H. M. Perry, 3rd (2003). "Andropause: an old concept in new clothing." *Clin Geriatr Med* 19(3): 507-528.

Morrison, J. H., R. D. Brinton, et al. (2006). "Estrogen, menopause, and the aging brain: how basic neuroscience can inform hormone therapy in women." *J Neurosci* 26(41): 10332-10348.

Mortola, J. F. and S. S. Yen (1990). "The effects of oral dehydroepiandrosterone on endocrine-metabolic parameters in postmenopausal women." *J Clin Endocrinol Metab* 71(3): 696-704.

Mostaghel, E. A., S. T. Page, et al. (2007). "Intraprostatic androgens and androgen-regulated gene expression persist after testosterone suppression: therapeutic implications for castration-resistant prostate cancer." *Cancer Res* 67(10): 5033-5041.

Murray, R. and P. Pitt (1985). "Treatment of advanced prostatic cancer, resistant to conventional therapy, with aminoglutethimide." *Eur J Cancer Clin Oncol* 21(4): 453-458.

Nair, K. S., R. A. Rizza, et al. (2006). "DHEA in elderly women and DHEA or testosterone in elderly men." *N Engl J Med* 355(16): 1647-1659.

Nathorst-Boos, J. and B. von Schoultz (1992). "Psychological reactions and sexual life after hysterectomy with and without oophorectomy." *Gynecol Obstet Invest* 34(2): 97-101.

Need, A. G., M. Horowitz, et al. (1989). "Effects of nandrolone decanoate and antiresorptive therapy on vertebral density in osteoporotic postmenopausal women." *Arch. Intern. Med.* 149: 57-60.

Nestler, J. E., C. O. Barlascini, et al. (1988). "Dehydroepiandrosterone reduces serum low density lipoprotein levels and body fat but does not alter insulin sensitivity in normal men." *J. Clin. Endocrinol. Metab.* 66: 57-61.

Nishiyama, T., Y. Hashimoto, et al. (2004). "The influence of androgen deprivation therapy on dihydrotestosterone levels in the prostatic tissue of patients with prostate cancer." *Clin Cancer Res.* 10(21): 7121-7126.

Notelovitz, M., N. Watts, et al. (1992). *Effects of estrogen plus low dose androgen vs estrogen alone on menopausal symptoms in oophorectomized/hysterectomized women*. North Am. Menopause Soc., Clevland.

O'Connor, D. B., D. M. Lee, et al. (2011). "The Relationships between Sex Hormones and Sexual Function in Middle-Aged and Older European Men." *J Clin Endocrinol Metab* 96(10): E1577-E1587.

O'Leary, M. P., F. J. Fowler, et al. (1995). "A brief male sexual function inventory for urology." *Urology* 46(5): 697-706.

Ohlsson, C., F. Labrie, et al. (2010). "Low serum levels of dehydroepiandrosterone sulfate predict all-cause and cardiovascular mortality in elderly men." *J Clin Endocrinol Metab* 95: 4406-4414.

Ota, H., M. Akishita, et al. (2012). "Testosterone deficiency accelerates neuronal and vascular aging of SAMP8 mice: protective role of eNOS and SIRT1." *PLoS One* 7(1): e29598.

Page, S. T., J. K. Amory, et al. (2005). "Exogenous testosterone alone or with finasteride increases physical performance, grip strength, and lean body mass in older men with low serum T." *J Clin Endocrinol Metab* 90(3): 1502-1510.

Pechersky, A. V., V. I. Mazurov, et al. (2002). "Androgen administration in middle-aged and ageing men: effects of oral testosterone undecanoate on dihydrotestosterone, oestradiol and prostate volume." *Int J Androl* 25(2): 119-125.

Percheron, G., J. Y. Hogrel, et al. (2003). "Effect of 1-year oral administration of dehydroepiandrosterone to 60- to 80-year-old individuals on muscle function and cross-sectional area: a double-blind placebo-controlled trial." *Arch Intern Med* 163(6): 720-727.

Petri, M. A., R. G. Lahita, et al. (2002). "Effects of prasterone on corticosteroid requirements of women with systemic lupus erythematosus: a double-blind, randomized, placebo-controlled trial." *Arthritis Rheum* 46(7): 1820-1829.

Petri, M. A., P. J. Mease, et al. (2004). "Effects of prasterone on disease activity and symptoms in women with active systemic lupus erythematosus." *Arthritis Rheum* 50(9): 2858-2868.

Pike, C. J., J. C. Carroll, et al. (2009). "Protective actions of sex steroid hormones in Alzheimer's disease." *Front Neuroendocrinol* 30(2): 239-258.

Poretsky, L., D. J. Brillon, et al. (2006). "Endocrine effects of oral dehydroepiandrosterone in men with HIV infection: a prospective, randomized, double-blind, placebo-controlled trial." *Metabolism* 55(7): 858-870.

Prostate Cancer Triallists' Collaborative Group (2000). "Maximum androgen blockade in advanced prostate cancer: an overview of the randomised trials." *Lancet* 355: 1491-1498.

Pugh, P. J., R. D. Jones, et al. (2004). "Testosterone treatment for men with chronic heart failure." *Heart* 90(4): 446-447.

Raisz, L. G., B. Wiita, et al. (1996). "Comparison of the effects of estrogen alone and estrogen plus androgen on biochemical markers of bone formation and resorption in postmenopausal women." *J Clin Endocrinol Metab* 81(1): 37-43.

Rasmussen, K. R., M. J. Arrowood, et al. (1992). "Effectiveness of dehydroepiandrosterone in reduction of cryptosporidial activity in immunosuppressed rats." *Antimicrob. Agents Chemother.* 36: 220-222.

Raven, P. W. and J. P. Hinson (2007). "Dehydroepiandrosterone (DHEA) and the menopause: an update." *Menopause Int* 13(2): 75-78.

Rocca, W. A., J. H. Bower, et al. (2007). "Increased risk of cognitive impairment or dementia in women who underwent oophorectomy before menopause." *Neurology* 69(11): 1074-1083.

(56) References Cited

OTHER PUBLICATIONS

Rocca, W. A., B. R. Grossardt, et al. (2006). "Survival patterns after oophorectomy in premenopausal women: a population-based cohort study." *Lancet Oncol* 7(10): 821-828.
Roy, T. A., M. R. Blackman, et al. (2002). "Interrelationships of serum testosterone and free testosterone index with FFM and strength in aging men." *Am J Physiol Endocrinol Metab* 283(2): E284-294.
Saad, F., L. J. Gooren, et al. (2008). "A dose-response study of testosterone on sexual dysfunction and features of the metabolic syndrome using testosterone gel and parenteral testosterone undecanoate." *J Androl* 29(1): 102-105.
Salmimies, P., G. Kockott, et al. (1982). "Effects of testosterone replacement on sexual behavior in hypogonadal men." *Arch Sex Behav* 11(4): 345-353.
Savvas, M., J. W. W. Studd, et al. (1988). "Skeletal effects of oral oestrogen compared with subcutaneous oestrogen and testosterone in postmenopausal women." *Br. Med. J.* 297: 331-333.
Schaap, L. A., S. M. Pluijm, et al. (2005). "The association of sex hormone levels with poor mobility, low muscle strength and incidence of falls among older men and women." *Clin Endocrinol (Oxf)* 63(2): 152-160.
Schriock, E. D., C. K. Buffington, et al. (1988). "Divergent correlations of circulating dehydroepiandrosterone sulfate and testosterone with insulin levels and insulin receptor binding." *J. Clin. Endocrinol. Metab.* 66: 1329-1331.
Schwartz, A. G., L. Pashko, et al. (1986). "Inhibition of tumor development by dehydroepiandrosterone and related steroids." *Toxicol. Pathol.* 14: 357-362.
Seftel, A. D., R. J. Mack, et al. (2004). "Restorative increases in serum testosterone levels are significantly correlated to improvements in sexual functioning." *J Androl* 25(6): 963-972.
Shabsigh, A., Y. Kang, et al. (2005). "Clomiphene citrate effects on testosterone/estrogen ratio in male hypogonadism." *J Sex Med* 2(5): 716-721.
Sherwin, B. B. (1988). "Affective changes with estrogen and androgen replacement therapy in surgically menopausal women." *J. Affect. Disord.* 14: 177-187.
Sherwin, B. B. and M. M. Gelfand (1985). "Differential symptom response to parenteral estrogen and/or androgen administration in the surgical menopause." *Am. J. Obstet. Gynecol.* 151: 153-160.
Sherwin, B. B. and M. M. Gelfand (1987). "The role of androgen in the maintenance of sexual functioning in oophorectomized women." *Psychosom Med.* 49: 397-409.
Shifren, J. L., G. D. Braunstein, et al. (2000). "Transdermal testosterone treatment in women with impaired sexual function after oophorectomy." *N Engl J Med* 343(10): 682-688.
Shigehara, K. and M. Namiki (2011). "Late-onset hypogonadism syndrome and lower urinary tract symptoms." *Korean J Urol* 52(10): 657-663.
Shimokata, H., J. D. Tobin, et al. (1989). "Studies in the distribution of body fat: I. Effects of age, sex, and obesity." *J Gerontol* 44(2): M66-73.
Shores, M. M., N. L. Smith, et al. (2012). "Testosterone treatment and mortality in men with low testosterone levels." *J Clin Endocrinol Metab* 97(6): 2050-2058.
Sibonga, J. D., G. L. Evans, et al. (1996). "Ovarian status influences the skeletal effects of tamoxifen in adult rats." *Breast Cancer Res. Treat.* 41: 71-79.
Sih, R., J. E. Morley, et al. (1997). "Testosterone replacement in older hypogonadal men: a 12-month randomized controlled trial." *J Clin Endocrinol Metab* 82(6): 1661-1667.
Simard, J., R. Sanchez, et al. (1997). "Blockade of the stimulatory effect of estrogens, OH-Tamoxifen, OH-Toremifene, Droloxifene and Raloxifene on alkaline phosphatase activity by the antiestrogen EM-800 in human endometrial adenocarcinoma Ishikawa cells." *Cancer Res.* 57: 3494-3497.
Simpkins, J. W., P. S. Green, et al. (1997). "Role of estrogen replacement therapy in memory enhancement and the prevention of neuronal loss associated with Alzheimer's disease." *Am J Med* 103(3A): 19S-25S.
Siris, E. S., Y. T. Chen, et al. (2004). "Bone mineral density thresholds for pharmacological intervention to prevent fractures." *Arch Intern Med* 164(10): 1108-1112.
Smith, K. W., H. A. Feldman, et al. (2000). "Construction and field validation of a self-administered screener for testosterone deficiency (hypogonadism) in ageing men." *Clin Endocrinol (Oxf)* 53(6): 703-711.
Smith, M. R. (2006). "Treatment-related osteoporosis in men with prostate cancer." *Clin Cancer Res* 12(20 Pt 2): 6315s-6319s.
Snyder, P. J., H. Peachey, et al. (2000). "Effects of testosterone replacement in hypogonadal men." *J Clin Endocrinol Metab* 85(8): 2670-2677.
Snyder, P. J., H. Peachey, et al. (1999). "Effect of testosterone treatment on body composition and muscle strength in men over 65 years of age." *J Clin Endocrinol Metab* 84(8): 2647-2653.
Storer, T. W., L. Magliano, et al. (2003). "Testosterone dose-dependently increases maximal voluntary strength and leg power, but does not affect fatigability or specific tension." *J Clin Endocrinol Metab* 88(4): 1478-1485.
Studd, J. W., W. P. Collins, et al. (1977). "Oestradiol and testosterone implants in the treatment of psychosexual problems in the post-menopausal woman." *Br. J. Obstet. Gynecol.* 84: 314-315.
Suzuki, T., N. Suzuki, et al. (1991). "Dehydroepiandrosterone enhances IL2 production and cytotoxic effector function of human T cells." *Clin. Immunol. Immunopathol.* 61: 202-211.
Tagliaferro, A. R., J. R. Davis, et al. (1986). "Effects of dehydroepiandrosterone acetate on metabolism, body weight and composition of male and female rats." *J. Nutr.* 116: 1977-1983.
Takao, T., A. Tsujimura, et al. (2009). "Lower urinary tract symptoms after hormone replacement therapy in Japanese patients with late-onset hypogonadism: a preliminary report." *Int J Urol* 16(2): 212-214.
Tan, K. C., S. W. Shiu, et al. (1998). "Effects of testosterone replacement on HDL subfractions and apolipoprotein A-I containing lipoproteins." *Clin Endocrinol (Oxf)* 48(2): 187-194.
Tan, R. S. and S. J. Pu (2003). "A pilot study on the effects of testosterone in hypogonadal aging male patients with Alzheimer's disease." *Aging Male* 6(1): 13-17.
Taylor, F. and L. Levine (2010). "Clomiphene citrate and testosterone gel replacement therapy for male hypogonadism: efficacy and treatment cost." *J Sex Med* 7(1 Pt 1): 269-276.
Tchernof, A., J. P. Després, et al. (1995). "Reduced testosterone and adrenal C19 steroid levels in obese men." *Metabolism* 44: 513-519.
Tchernof, A., F. Labrie, et al. (1996). "Obesity and metabolic complications: contribution of DHEA and other steroid hormones." *J. Endocrinol.* 150: S155-S164.
Tenover, J. S. (1992). "Effects of testosterone supplementation in the aging male." *J Clin Endocrinol Metab* 75(4): 1092-1098.
Tivesten, A., L. Vandenput, et al. (2009). "Low serum testosterone and estradiol predict mortality in elderly men." *J Clin Endocrinol Metab* 94(7): 2482-2488.
Traish, A. M., A. Guay, et al. (2009). "The dark side of testosterone deficiency: I. Metabolic syndrome and erectile dysfunction." *J Androl* 30(1): 10-22.
Traish, A. M., A. Haider, et al. (2013). "Long-term testosterone therapy in hypogonadal men ameliorates elements of the metabolic syndrome: an observational, long-term registry study." *Int J Clin Pract.*
Traish, A. M., H. P. Kang, et al. (2011). "Dehydroepiandrosterone (DHEA)—a precursor steroid or an active hormone in human physiology." *J Sex Med* 8(11): 2960-2982; quiz 2983.
Travison, T. G., J. E. Morley, et al. (2006). "The relationship between libido and testosterone levels in aging men." *J Clin Endocrinol Metab* 91(7): 2509-2513.
Trenell, M. I., N. S. Marshall, et al. (2007). "Sleep and metabolic control: waking to a problem?" *Clin Exp Pharmacol Physiol* 34(1-2): 1-9.

(56) References Cited

OTHER PUBLICATIONS

Turhan, S., C. Tulunay, et al. (2007). "The association between androgen levels and premature coronary artery disease in men." *Coron Artery Dis* 18(3): 159-162.
Ueno, S., M. Namiki, et al. (2006). "Efficacy of primary hormonal therapy for patients with localized and locally advanced prostate cancer: a retrospective multicenter study." *Int J Urol* 13(12): 1494-1500.
Valenti, G., L. Denti, et al. (2004). "Effect of DHEAS on skeletal muscle over the life span: the InCHIANTI study." *J Gerontol A Biol Sci Med Sci* 59(5): 466-472.
Vallee, M., W. Mayo, et al. (2001). "Role of pregnenolone, dehydroepiandrosterone and their sulfate esters on learning and memory in cognitive aging." *Brain Res Brain Res Rev* 37(1-3): 301-312.
Vermeulen, A. (2003). "Diagnosis of partial androgen deficiency in the aging male." *Ann Endocrinol (Paris)* 64(2): 109-114.
Vigen, R., C. I. O'Donnell, et al. (2013). "Association of testosterone therapy with mortality, myocardial infarction, and stroke in men with low testosterone levels." *Jama* 310(17): 1829-1836.
Villareal, D. T. and J. O. Holloszy (2004). "Effect of DHEA on abdominal fat and insulin action in elderly women and men: a randomized controlled trial." *JAMA* 292(18): 2243-2248.
Villareal, D. T., J. O. Holloszy, et al. (2000). "Effects of DHEA replacement on bone mineral density and body composition in elderly women and men." *Clin Endocrinol (Oxf)* 53(5): 561-568.
Wakeling, A. E. (1993). "The future of new pure antiestrogens in clinical breast cancer." *Breast Cancer Res. Treat.* 25: 1-9.
Wang, C., G. Cunningham, et al. (2004). "Long-term testosterone gel (AndroGel) treatment maintains beneficial effects on sexual function and mood, lean and fat mass, and bone mineral density in hypogonadal men." *J Clin Endocrinol Metab* 89(5): 2085-2098.
Wang, C., E. Nieschlag, et al. (2009a). "Investigation, treatment, and monitoring of late-onset hypogonadism in males: ISA, ISSAM, EAU, EAA, and ASA recommendations." *J Androl* 30(1): 1-9.
Wang, C., E. Nieschlag, et al. (2009b). "ISA, ISSAM, EAU, EAA and ASA recommendations: investigation, treatment and monitoring of late-onset hypogonadism in males." *Aging Male* 12(1): 5-12.
Wang, C., R. S. Swerdloff, et al. (2000). "Transdermal testosterone gel improves sexual function, mood, muscle strength, and body composition parameters in hypogonadal men." *J Clin Endocrinol Metab* 85(8): 2839-2853.
Weill-Engerer, S., J. P. David, et al. (2002). "Neurosteroid quantification in human brain regions: comparison between Alzheimer's and nondemented patients." *J Clin Endocrinol Metab* 87(11): 5138-5143.
Weinstein, R. S. and M. S. Hutson (1987). "Decreased trabecular width and increased trabecular spacing contribute to bone loss with aging." *Bone* 8: 137-142.
Whitten, S. J., A. K. Nangia, et al. (2006). "Select patients with hypogonadotropic hypogonadism may respond to treatment with clomiphene citrate." *Fertil Steril* 86(6): 1664-1668.
Williams, M. R., T. Dawood, et al. (2004). "Dehydroepiandrosterone increases endothelial cell proliferation in vitro and improves endothelial function in vivo by mechanisms independent of androgen and estrogen receptors." *J Clin Endocrinol Metab* 89(9): 4708-4715.

Wolkowitz, O. M., V. I. Reus, et al. (1999). "Double-blind treatment of major depression with dehydroepiandrosterone." *Am T Psychiatry* 156(4): 646-649.
Wu, F. C., A. Tajar, et al. (2010). "Identification of late-onset hypogonadism in middle-aged and elderly men." *N Engl J Med* 363(2): 123-135.
Wu, F. C. and A. von Eckardstein (2003). "Androgens and coronary artery disease." *Endocr Rev* 24(2): 183-217.
Yaffe, K. (1998). "Estrogen therapy in postmenopausal women: effects on cognitive function and dementia." *JAMA* 279: 688-695.
Yau, J. L., S. Rasmuson, et al. (2003). "Dehydroepiandrosterone 7-hydroxylase CYP7B: predominant expression in primate hippocampus and reduced expression in Alzheimer's disease." *Neuroscience* 121(2): 307-314.
Yen, S. S., A. J. Morales, et al. (1995). "Replacement of DHEA in aging men and women. Potential remedial effects." *Ann. N.Y. Acad. Sci.* 774: 128-142.
Yen, T. T., J. A. Allan, et al. (1977). "Prevention of obesity in Avy/a mice by dehydroepiandrosterone." *Lipids* 12: 409-413.
Zitzmann, M. (2009). "Testosterone deficiency, insulin resistance and the metabolic syndrome." *Nat Rev Endocrinol* 5(12): 673-681.
Zitzmann, M., S. Faber, et al. (2006). "Association of specific symptoms and metabolic risks with serum testosterone in older men." *J Clin Endocrinol Metab* 91(11): 4335-4343.
H. Bundgaard "5. Design and Application of Prodrugs" (In a textbook of Drug Design and Development. Edited by P. Krogsgaard-Larsen and H. Bundgaard; Harwood Academic Publishers GmbH, Chur, Switzerland, 1991.
Leigh C. Murphy, et al., "Antitumor Activity of Clomiphene Analogs in Vitro: Relationship to Affinity for the Estrogen Receptor and Another High Affinity Antiestrogen-Binding Site," Journal of Clinical Endocrinology and Metabolism, vol. 57, No. 2, 1983 pp. 373-379.
O.E. Young, et al., "Effects of Fulvestrant 750 mg in Premenopausal Women With Oestrogen-Receptor-Positive Primary Breast Cancer," European Journal of Cancer, 44, 2008, pp. 391-399.
Ahalya Premkumar, et al., "Gynecologic and Hormonal Effects of Raloxifene in Premenopausal Women," Fertility and Sterility, vol. 88, No. 6, Dec. 2007, pp. 1637-1644.
Nicolas C. Nicolaides, M.D., et al., "Adrenal Insufficiency," Endotext—NCBI Bookshelf, 2013, pp. 1-24.
Marie-France Kong, et al., "Eighty-Six Cases of Addison's Disease," Clinical Endocrinology, 1994, 41, pp. 757-761.
Giovanni Corona, et al., "Emerging Medication for the Treatment of Male Hypogonadism," Expert Opinion Emerging Drugs, 2012, 17(2), pp. 239-259.
International Preliminary Report on Patentability dated Sep. 13, 2016 containing the Written Opinion of the International Searching Authority in corresponding International Application No. PCT/CA2015/000142 (7 total pages).
International Search Report dated Jun. 10, 2015 in corresponding International Application No. PCT/CA2015/000142 (7 total pages).
Gherardo Mazziotti, MD, PhD, et al., "Drug-Induced Osteoporosis: Mechanisms and Clinical Implications," The American Journal of Medicine (2010) 123, pp. 877-884.
Ronny B. W. Tan, MBBS, MRCSEd, M Med (Surgery) FAMS (Urology), et al., "Clinical Use of Aromatase Inhibitors in Adult Males," Sex Med Rev (2014) 2, pp. 79-90.

* cited by examiner

**STEROIDOGENIC ENZYMES
ADRENAL - INTRACRINE TISSUES**

Figure 12

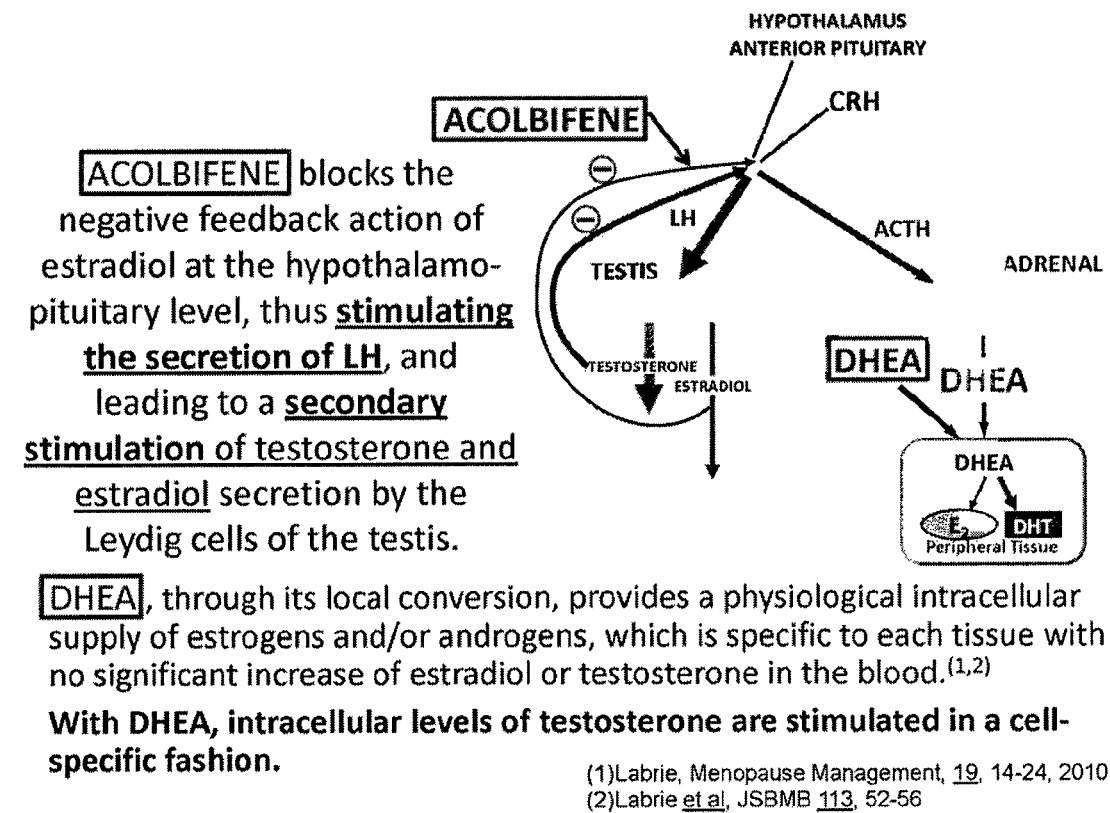

ACOLBIFENE blocks the negative feedback action of estradiol at the hypothalamo-pituitary level, thus <u>stimulating the secretion of LH</u>, and leading to a <u>secondary stimulation of testosterone and estradiol</u> secretion by the Leydig cells of the testis.

DHEA, through its local conversion, provides a physiological intracellular supply of estrogens and/or androgens, which is specific to each tissue with no significant increase of estradiol or testosterone in the blood.[1,2]

With DHEA, intracellular levels of testosterone are stimulated in a cell-specific fashion.

(1) Labrie, Menopause Management, 19, 14-24, 2010
(2) Labrie et al, JSBMB 113, 52-56

TREATMENT OF MALE ANDROGEN DEFICIENCY SYMPTOMS OR DISEASES WITH SEX STEROID PRECURSOR COMBINED WITH SERM

CROSS REFERENCE OF THE RELATED APPLICATION(S)

This present application claims benefit of and priority to U.S. Provisional Application No. 61/950,644 filed on Mar. 10, 2014 by Fernand Labrie et al. and entitled "TREATMENT OF MALE ANDROGEN DEFICIENCY SYMPTOMS OR DISEASES WITH SEX STEROID PRECURSOR COMBINED WITH SERM", the entire contents of which are hereby incorporated by reference.

FIELD OF THE INVENTION

The present invention relates to a novel treatment of low total androgens accompanied by one or more symptoms classically attributed to male hypogonadism or low testosterone. The number of individuals over 65 years of age has increased more than 10-fold compared with the 1990s (Shigehara and Namiki 2011). In the aging process, low testosterone is often accompanied by decreased sense of well-being, depression, decreased libido and increased erectile dysfunction (Lunenfeld and Nieschlag 2007). The decrease in serum testosterone levels associated with aging has been called late-onset hypogonadism (LOH) (Wang, Nieschlag et al. 2009b). The diagnosis of male hypogonadism usually combined symptomatology in addition to low serum testosterone reported as below 2.0-3.5 ng/mL.

The precise threshold testosterone level below which symptoms of androgen deficiency and adverse health outcomes occur is not known and may be age-dependent (Kelleher, Conway et al. 2004; Zitzmann, Faber et al. 2006; Hall, Esche et al. 2008).

At a threshold of 3.0 ng testosterone/mL, symptoms occur more below this value (Kelleher, Conway et al. 2004; Zitzmann, Faber et al. 2006; Bhasin, Cunningham et al. 2010). The guidelines from the US Endocrine Society have defined LOH as a serum testosterone less than 2.0 ng/mL in conjunction with one or more signs and symptoms of classical hypogonadism (Bhasin, Cunningham et al. 2006). The American Society of Andrology recommends less than 3.0 ng/mL in symptomatic men (American Society of Andrology 2006). On the other hand, according to the International Society for the Study of the Aging Male (ISSAM), symptomatic aged men should be considered hypogonadal at less than 3.50 ng testosterone/mL (Wang, Nieschlag et al. 2009a).

In parallel, the testosterone concentration below which testosterone administration improves outcomes is unclear and may vary among individuals and among target organs. Therefore, the available evidence does not support use of an arbitrary threshold for testosterone level below which clinical androgen deficiency occurs and that confirms the diagnosis of hypogonadism in all patients (Bhasin, Cunningham et al. 2006).

A correlation between low physical vigor and low serum testosterone has been repeatedly low (Xu, Gouras et al. 1998; Travison, Morley et al. 2006). It is also quite possible, as mentioned above, that various thresholds exist for the various androgen-dependent targets (Bhasin, Woodhouse et al. 2005; Gray, Singh et al. 2005; Zitzmann, Faber et al. 2006; Shigehara and Namiki 2011).

A novel component at the basis of the present invention is that consideration should also be given to isolated or combined low intracrine peripheral formation of androgens from low serum dehydroepiandrosterone (DHEA) with a symptomatology similar to that attributed to hypogonadism. Accordingly, the DHEA-derived androgen metabolites, especially androsterone glucuronide (ADT-G), can be measured as described (Labrie, Bélanger et al. 2006). The normal values of dehydroepiandrosterone (DHEA) and androgen metabolite glucuronides, namely ADT-G (estimate of total androgenicity) and other androgens and metabolites can be seen in (Labrie, Cusan et al. 2009; Labrie 2010b; Ohlsson, Labrie et al. 2010; Labrie 2011; O'Connor, Lee et al. 2011). Values of serum DHEA below 2.0 ng/mL by themselves can be considered low with normal testosterone but the concentration of serum testosterone must also be taken into consideration and the symptoms of low total androgens results from the combination of low testosterone and/or low DHEA resulting in low total androgens reflected by low androgen metabolites. Serum ADT-G below 25 ng/mL can be considered a parameter of low total hypoandrogenecity (Labrie, Diamond et al. 1997b).

Male hypogonadism can represent deficiency in spermatogenesis or a deficiency in testicular testosterone secretion. This second part will be involved in the present invention (please see (Corona, Rastrelli et al. 2012) for more details).

Typically, late-onset hypogonadism (LOH) appearing in the aging male combines low serum testosterone with one or more symptoms of hypoandrogenecity. However, since up to 50% of total androgens derive from DHEA, low DHEA can be as responsible as low testosterone of the signs and symptoms of hypogonadism.

Consequently, the signs and symptoms of hypogonadism and/or low peripheral androgen formation can be appropriate conditions for therapy. Free testosterone can also be measured according to Vermeulen's formula www.issam.ch/freetesto.htm, but is not usually very informative.

In addition to testosterone, the testis, through the action of aromatase secretes the estrogens estrone and estradiol (FIG. 1). The secretion of luteinizing hormone (LH) by the anterior pituitary gland is stimulated by the pulsatile secretion of GnRH (Gonadotropin-Releasing Hormone) from the hypothalamus while both testosterone and estradiol exert global inhibitory effects at the hypothalamo-pituitary level on LH secretion (Corona, Rastrelli et al. 2012). LH then stimulates testosterone secretion by the Leydig cells in the testis (FIG. 1).

The guidelines of the US Endocrine Society recommend testosterone treatment only in men with "consistent symptoms and signs and unequivocally low serum testosterone levels". However, it has been found that only half the men receiving testosterone replacement therapy were diagnosed with male hypogonadism. In fact, 34% were treated for fatigue, 31% for erectile dysfunction and 12% for psychosexual dysfunction (Baillargeon, Urban et al. 2013).

As mentioned above, it must be considered that up to 50% of total androgens in men are made locally in peripheral tissues from DHEA that decreases with age by as much as 80% on average in men aged 75 years or more (Labrie, Bélanger et al. 1997b), thus providing a reason why low DHEA has at least an equal role compared to low serum testosterone to explain the symptoms and signs so-far attributed to male hypogonadism (Labrie, Bélanger et al. 1997a).

The Endocrine Society has a Clinical Practice Guideline on testosterone therapy, namely Testosterone Therapy in Men with Androgen Deficiency Syndrome (2006; revised 2010) at www.endocrine.org. It includes the revised recommendations on the Prostate Specific Antigen exclusion criteria and PSA follow-up guidance.

Low testosterone can be accompanied by any single or a combination of the following signs or symptoms:
- loss of libido (interest in sex)
- difficulty in getting an erection (erectile dysfunction)
- tiredness and lack of energy (loss of energy, energy loss)
- depression
- loss of bone (decreased bone mineral density and increased risk of fracture)
- loss of muscle and muscle weakness
- loss of body hair
- fertility problems Additional benefits such as treatment or reduction of the likelihood or risk of acquiring the following medical problems, namely hypercholesterolemia, hyperlipidemia, atherosclerosis, hypertension, Alzheimer's disease, loss of memory, loss of cognition, dementia, insomnia, cardiovascular diseases, insulin resistance, Type 2 diabetes and obesity (especially abdominal obesity) (Comhaire 2000; Ding, Song et al. 2006; Khaw, Dowsett et al. 2007; Bassil, Alkaade et al. 2009; Zitzmann 2009) are also provided by treatment with the invention.

Low serum testosterone in men is associated with low muscle mass, decreased muscle strength and poor mobility (Roy, Blackman et al. 2002; Schaap, Pluijm et al. 2005). Testosterone supplementation in healthy older men increases muscle mass and strength and leg power, these being important factors of mobility (Bhasin, Storer et al. 1996; Sih, Morley et al. 1997; Snyder, Peachey et al. 1999; Storer, Magliano et al. 2003; Bhasin, Woodhouse et al. 2005; Page, Amory et al. 2005).

Symptoms/signs of androgen deficiency in aging males can be as stated in the Clinical Practice Guideline of the Endocrine Society (Bhasin, Cunningham et al. 2006).

TABLE 1A

Symptoms and signs suggestive of androgen deficiency in aging men

Reduced sexual desire (libido) and activity
Decreased spontaneous erections
Breast discomfort, gynecomastia
Loss of body (axillary and pubic) hair, reduced shaving
Very small or shrinking testes (especially <5 mL)
Inability to father children, low or zero sperm counts
Height loss, low trauma fracture, low bone mineral density
Reduced muscle bulk and strength
Hot flushes, sweats

TABLE 1B

Other symptoms and signs associated with androgen deficiency that are less specific than those in Table 1A Decreased energy, motivation, initiative, aggressiveness, self-confidence
Feeling sad or blue, depressed mood, dysthymia
Poor concentration and memory
Sleep disturbance, increased sleepiness
Mild anemia (normochromic, normocytic, in the female range)
Increased body fat, body mass index
Diminished physical or work performance (Bhasin, Cunningham et al. 2006)

Aging itself is often associated with a decline in sexual functioning in men (Vermeulen 2003; Ebert, Jockenhovel et al. 2005).

The diagnosis of male hypogonadism can be helped by the ANDROTEST (Corona, Jannini et al. 2006; Corona, Mannucci et al. 2006). Differential diagnosis can also be helped by the information provided by (Corona, Rastrelli et al. 2012). LOH has also been defined by the presence of at least three sexual symptoms associated with a total testosterone level of less than 3.2 ng/mL (Wu, Tajar et al. 2010). In that study performed in a random population sample of 3369 men aged 40 to 79 years, differences between asymptomatic and symptomatic men in relation with serum testosterone were minimal. One possible explanation could be, as indicated above, that serum testosterone is not the exclusive source of androgenic activity which is, as mentioned above, up to 50% from DHEA-derived androgens (Labrie, Dupont et al. 1985; Labrie 2011).

The physiological role of testosterone in male sexual behavior is poorly understood. Many studies with attempts to correlate male sexual behavior and the concentration of serum testosterone have given conflicting results. There are wide variations between serum testosterone levels and erectile dysfunction (Salmimies, Kockott et al. 1982; Gooren 1987; Bhasin, Cunningham et al. 2006; Traish, Guay et al. 2009). It remains, however, that low serum testosterone has become standard clinical practice in the evaluation of sexual disorders in men.

Diagnosis of late-onset male hypogonadism can be helped by questionnaires, although clinical evaluation of the total clinical picture is of major importance. The instruments which can be used are, without limitation, Androgen Deficiency in Aging Males (ADAM) (Morley, Charlton et al. 2000), the Aging Males Symptoms (AMS) Rating Scale (Moore, Huebler et al. 2004) and the Massachusetts Male Ageing Study (MMAS) Questionnaire (Smith, Feldman et al. 2000). Diagnosis can be helped with the Brief Sexual Function Inventory (BSFI) (O'Leary, Fowler et al. 1995). The instrument covers sexual drive (two items), erection (three items), ejaculation (two items), perception of problems in each area (three items) and overall satisfaction (one item).

There is an emerging medication for the treatment of male hypogonadism (see the two following recent reviews: (Corona, Rastrelli et al. 2012; Kim, Crosnoe et al. 2013)). In addition to the existing exogenous testosterone treatment, clinical data with selective estrogen receptor modulators (SERMs) are available. A SERM binds to the estrogen receptor in the hypothalamus and pituitary gland in competition with estradiol. The neutralization of inhibitory action of estradiol in the hypothalamus increases GnRH (gonadotropin-releasing hormone) secretion which stimulates LH secretion which increases testosterone production by the testes. Several studies with clomiphene citrate have been performed. Clomiphene citrate increases serum testosterone levels in the blood like the use of testosterone gels (Taylor and Levine 2010). Clomiphene citrate improves sexual function in hypogonadal men (Guay, Jacobson et al. 2003). Clomiphene citrate improves the testosterone-estradiol ratio in hypogonadal men (Shabsigh, Kang et al. 2005). Clomiphene citrate increases circulating testosterone and improves several hypogonadism-related symptoms (decreased libido, lack of energy) in young hypogonadal men (Katz, Nabulsi et al. 2011).

Enclomiphene (Androxal; Repros) is under development for male hypogonadism and infertility. Patents literature also indicates that SERMs or antiestrogens could be useful for male androgen deficiency including male hypogonadism (US 2006/0293294, US 2009/0215733, WO 01/91744, WO 03/072092, WO 2006/024689 and WO 2013/123218) and in combination with other active agents (US 2007/0078091 and WO 2013/130832). Other classes of compounds have been suggested to treat male hypogonadism, namely gonadotropins, 5α-reductase inhibitors, testosterone precursors, non-aromatizable androgens, aromatase inhibitors, selective estrogen receptor β agonists and selective androgen receptor modulators (SARMs). Gonadotropin therapy remains one of the few effective treatments for infertility in men with secondary hypogonadism (Liu, Baker et al. 2009; Farhat, Al-zidjali et al. 2010). Human chorionic gonadotropin is an LH analogue that stimulates Leydig cell production of testosterone and it can be derived from urine as well as recombinant sources.

In particular, the treatment includes the administration of a precursor of sex steroids in combination with a cell-specific selective estrogen receptor modulator (SERM), in particular acolbifene.

The invention also provides kits and pharmaceutical compositions for practicing the foregoing combination.

It is known that a large number of diseases, conditions and undesirable symptoms respond favorably to administering exogenous sex steroids, or precursors thereof. For example, estrogens are believed to decrease the rate of bone loss while androgens have been shown to build bone mass by stimulating bone formation.

Long-term testosterone treatment in hypogonadal men improves metabolic syndrome components. It reduced total cholesterol, low-density lipoprotein cholesterol, tryglycerides and increased HDL cholesterol levels. It also reduced blood glucose levels (Traish, Haider et al. 2013).

Treatment with dihydrotestosterone (DHT) for 2 years had no effect on prostate volume but decreased fat mass, increased lean mass, suppressed serum testosterone and decreased spinal bone mineral density, probably due to inhibition of LH secretion. Many other studies have shown the benefits of androgen replacement therapy with no significant change of prostatic volume or urinary symptoms (Sih, Morley et al. 1997; Kenny, Prestwood et al. 2001; Marks, Mazer et al. 2006; Saad, Gooren et al. 2008; Takao, Tsujimura et al. 2009). In a 10-year study with oral testosterone undecanoate, no increase in prostate size and no evidence of cancer was noted (Gooren 1994).

In hypogonadal men, even an improvement of lower urinary tract symptoms was observed (Pechersky, Mazurov et al. 2002), for review see (Amano, Imao et al. 2010; Shigehara and Namiki 2011). Oral testosterone undecanoate replacement for 8 months at doses of 40 to 160 mg/day did not change the prostate size nor showed deterioration of voiding symptoms (Franchi F, Luisi M et al. 1978). A study where 100 mg testosterone enanthate was injected weekly for 3 months similarly did not change prostate volume or post voiding residual volume (Tenover 1992).

In another study, androgen replacement therapy for 8 months increased prostate volume by 18% with no change in uroflowmetry data (Holmang, Marin et al. 1993). No difference in prostate volume was observed in another study (Behre, Bohmeyer et al. 1994).

Reduced libido and erectile dysfunction are considered as being the most proeminent symptoms of hypogonadism in men (Harman, Metter et al. 2001; Matsumoto 2002). In the Massachusetts Male Aging Study, the prevalence of complete erectile dysfunction increased 3-fold from 5% to 15% between the ages 40 and 70 years (Morley 2003).

In the European Male Aging Study (EMAS), on the other hand, a correlation was found between low serum testosterone and the symptoms poor morning erection, low sexual desire and erectile dysfunction (testosterone range 2.3 to 3.7 ng/mL) leading to the LOH (Late-Onset Hypogonadism) definition in men having the 3 symptoms and serum testosterone less than 3.2 ng/mL or 11 nmole per liter (Wu, Tajar et al. 2010). Testosterone controls gonadotropin secretion, masculinization during sexual maturation, induction and maintenance of sperm production, as well as libido and sexual function.

Both estrogens derived from androgens and androgens themselves exert a global negative effect on GnRH/LH secretion (FIG. 1). Estradiol, while being at much lower concentrations in the blood, is an efficient inhibitor of GnRH/LH secretion.

Serum testosterone levels vary significantly as a result of circadian and circannual rhythms, episodic secretion, and measurement variations. Testosterone concentrations may be affected by illness and certain medications (e.g. opiates and glucocorticoids).

In the TOM trial performed in men older than 65 years with chronic conditions and limitations in mobility, twice as many adverse events (AEs) were reported in the testosterone gel versus the placebo groups (Basaria, Coviello et al. 2010). In that relatively small group (testosterone in older men with mobility limitations, TOM) of 209 men with serum testosterone of 1.0 to 3.5 ng/mL with a high prevalence of chronic disease, namely hypertension, hyperlipidemia, diabetes and obesity, a higher incidence of cardiovascular events in the testosterone gel group stopped the trial. Greater improvement of leg-press and chest-press strength and in stair climbing while carrying a load was seen in the testosterone-treated versus placebo groups (Basaria, Coviello et al. 2010). The risk of cardiovascular AEs was greater in testosterone-treated men.

Testosterone replacement therapy is also associated with infertility as side effect due to decreased sperm count as well as decrease in testicular-size.

Testosterone injections have the advantage of low cost but have the disadvantage of non physiological peak and trough levels over the weekly, bi-weekly or long term dosing regimen.

In a group of 8709 Veteran Administration patients with serum testosterone<3.0 ng/mL, after a median of 531 days post coronography, 1223 of them started testosterone therapy (Vigen, O'Donnell et al. 2013). In that retrospective observational study, the rates of deaths at 3 years were 15.4% vs 18.5% in the control and testosterone groups, respectively. As stated, "this signal warrants cautions testosterone prescribing . . . " (Cappola 2013).

Metaanalysis of testosterone therapy trials, except the TOM trial, however, did not demonstrate adverse cardiovascular events (Calof, Singh et al. 2005; Haddad, Kennedy et al. 2007; Fernandez-Balsells, Murad et al. 2010).

Testosterone replacement therapy has been associated with increased sexual functioning and mood (Seftel, Mack et al. 2004; Wang, Cunningham et al. 2004).

In addition to improving sexual function (Wang, Swerdloff et al. 2000; Isidori, Giannetta et al. 2005; Bolona, Uraga et al. 2007), the administration of testosterone to men with symptomatic androgen deficiency increases bone mineral density (Snyder, Peachey et al. 2000; Isidori, Giannetta et al. 2005) increases fat-free mass (Isidori, Caprio et al. 1999; Snyder, Peachey et al. 2000; Isidori, Giannetta et al. 2005) and strength (Sih, Morley et al. 1997), improves insulin resistance (Jones and Saad 2009; Jones, Arver et al. 2011) and improves the lipid profile (Marin, Holmang et al. 1993; Jones and Saad 2009; Jones, Arver et al. 2011).

A significant problem with testosterone replacement therapy is that it suppresses testicular endogenous testosterone secretion and can result in azoospermia or impairment of spermatogenesis as indicated by the labeling accepted by the Food and Drug Administration (Kim, Crosnoe et al. 2013). Exogeneous testosterone inhibits the hypothalamo-pituitary-testicular axis and can result in infertility. Intramuscular testosterone has even been studied as a contraceptive agent (Liu, Swerdloff et al. 2006). In the present invention, the low testicular testosterone formation secondary to inhibition of LH secretion is avoided by the use of a SERM, in particular acolbifene that stimulates LH secretion instead of blocking endogenous LH and, secondarily, testosterone secretion.

SUMMARY OF THE INVENTION

It is an object of the present invention to provide a method of preventing, reducing or eliminating the incidence of male androgen deficiency symptoms or diseases including male hypogonadism-associated symptoms and diseases due to low testosterone and/or low peripheral androgen formation.

It is another object to provide methods of preventing, reducing or eliminating the incidence of loss of libido, erectile dysfunction, tiredness, loss of energy, depression, bone loss, muscle loss, muscle weakness, fat accumulation, memory loss, cognition loss, Alzheimer's disease, dementia, loss of body hair, fertility problems, insomnia, gynecomastia, anemia, hot flushes, sweats, decreased sense of well-being, obesity, osteoporosis, hypercholesterolemia, hyperlipidemia, atherosclerosis, hypertension, insulin resistance, cardiovascular disease and type 2 diabetes.

It is another object to provide methods of reducing the risk of the male patients acquiring breast cancer.

It is another object to provide kits and pharmaceutical compositions suitable for use in the above methods. Preferably, these products are packaged with directions for using the contents thereof for preventing, reducing or eliminating the incidence of male androgen deficiency symptoms or diseases including male hypogonadism-associated symptoms and diseases.

It is another object to provide kits and pharmaceutical compositions suitable for use in the above methods. Preferably, these products are packaged with directions for using the contents thereof for preventing, reducing or eliminating the incidence of loss of libido, erectile dysfunction, tiredness, loss of energy, depression, bone loss, muscle loss, muscle weakness, fat accumulation, memory loss, cognition loss, Alzheimer's disease, dementia, loss of body hair, fertility problems, insomnia, gynecomastia, anemia, hot flushes, sweats, decreased sense of well-being, obesity, osteoporosis, hypercholesterolemia, hyperlipidemia, atherosclerosis, hypertension, insulin resistance, cardiovascular disease and type 2 diabetes.

In one embodiment, the invention provides a method of preventing, reducing or eliminating the incidence of male androgen deficiency symptoms or diseases including male hypogonadism-associated symptoms and diseases, said method comprising administering to male patient in need of said prevention, reduction or elimination, a therapeutically effective amount of a sex steroid precursor or prodrug thereof in association with a therapeutically effective amount of a selective estrogen receptor modulator or an antiestrogen or prodrug of either.

It is preferred that the sex steroid precursor is selected from the group consisting of dehydroepiandrosterone, dehydroepiandrosterone-sulfate, androst-5-ene-3β,17β-diol, 4-androstene-3,17-dione, and a prodrug of any of the foregoing additional agents.

It is preferred that the selective estrogen receptor modulator is selected from the group comprising of Tamoxifen, Toremifene, CC 8490, SERM 3471, HMR 3339, HMR 3656, Raloxifene, LY 335124, LY 326315, Arzoxifene (LY 353381), Pipendoxifene (ERA 923), Bazedoxifene (TSE 424, WAY 140424), Oporia (Lasofoxifene), EM-652, EM-800, EM-652-HCl (acolbifene, EM-1538), 4-hydroxy-Tamoxifen, 4-hydroxy-Toremifene, Droloxifene, LY 335563, GW-5638, Idoxifene, Levormeloxifene, Iproxifen (TAT-59), Ospemifene (FC 1271), Fispemifene, Centchroman, CHF 4227, LY 2066948, LY 2120310, Sivifene, SR 16234, Clomiphene, Enclomiphene, Zuclomiphene, GW 7603, BL 3040, SRI 16158, SR 16157, SRI 16137, SR 16137, Rad 1901, (+)-3-(4-hydroxyphenyl)-2-[4-[2-(1-piperidinyl)ethoxy]phenyl]-4-(trifluoromethyl)-2H-1-benzopyran-7-ol, Femarelle, Nafoxidine and Endoxifen.

It is preferred that the antiestrogen is selected from the group comprising of Faslodex (ICI 182780, fulvestrant, 7α-[9-(4,4,5,5,5-pentafluoro-pentylsulphinyl)nonyl]oestra-1,3,5(10)-triene-3,17β-diol), ICI 164384, CH 4893237, ZK 246965 and SH 646.

It is preferred that the selective estrogen receptor modulator has one of the following formulae selected from the group comprising of:

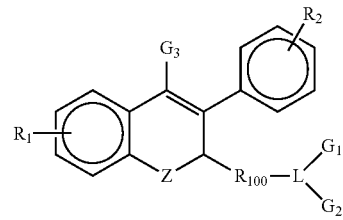

wherein $R_1$ and $R_2$ are independently hydrogen, hydroxyl, halogen, $C_1$-$C_6$ alkyl or a moiety which is converted to hydroxyl in vivo;

wherein Z is either absent or selected from the group consisting of —$CH_2$—, —O—, —S— and —$NR_3$— ($R_3$ being hydrogen or $C_1$-$C_6$ alkyl);

wherein the $R_{100}$ is a bivalent moiety which distances L from the B-ring by 4-10 intervening atoms;

wherein L is a bivalent or trivalent moiety selected from the group of —SO—, —CON<, —N<, and —SON<;

wherein $G_1$ is selected from the group consisting of hydrogen, a $C_1$ to $C_5$ hydrocarbon, a bivalent moiety which in combination with $G_2$ and L is a 5- to 7-membered heterocyclic ring, and halo or unsaturated derivatives of the foregoing;

wherein $G_2$ is either absent or selected from the group consisting of hydrogen, a to $C_5$ hydrocarbon, a bivalent moiety which in combination with $G_1$ and L is a 5- to 7-membered heterocyclic ring, and halo or unsaturated derivatives of the foregoing;

wherein $G_3$ is selected from the group consisting of hydrogen, methyl, ethyl and trifluoromethyl;

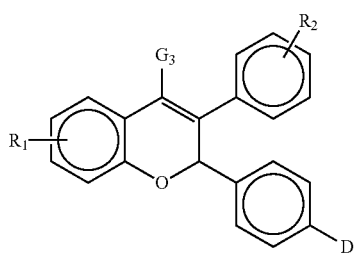

or a pharmaceutically acceptable salt thereof,
wherein D is —OCH$_2$CH$_2$N(R$_3$)R$_4$ (R$_3$ and R$_4$ either being independently selected from the group consisting of C$_1$-C$_4$ alkyl, or R$_3$, R$_4$ and the nitrogen atom to which they are bound, together being a ring structure selected from the group consisting of pyrrolidinyl, 2,2-dimethylpyrrolidinyl, 2-methylpyrrolidinyl, piperidino, hexamethyleneimino, and morpholino);
wherein R$_1$ and R$_2$ are independently selected from the group consisting of: hydrogen, hydroxyl, halogen, C$_1$-C$_6$ alkyl, and a moiety converted in vivo to hydroxyl;
wherein G$_3$ is selected from the group consisting of hydrogen, methyl, ethyl and trifluoromethyl;

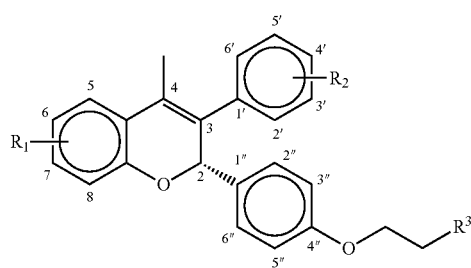

or a pharmaceutically acceptable salt thereof;
wherein a benzopyran compound which is an optically active compound having an absolute configuration S on carbon 2;
wherein R$_1$ and R$_2$ are independently selected from the group consisting of hydroxyl, halogen, C$_1$-C$_6$ alkyl, and a moiety convertible in vivo to hydroxyl;
wherein R$^3$ is a species selected from the group consisting of saturated, unsaturated or substituted pyrrolidinyl, saturated, unsaturated or substituted piperidino, saturated, unsaturated or substituted piperidinyl, saturated, unsaturated or substituted morpholino, nitrogen-containing cyclic moiety, nitrogen-containing polycyclic moiety, and NRaRb (Ra and Rb being independently hydrogen, straight or branched C$_1$-C$_6$ alkyl, straight or branched C$_2$-C$_6$ alkenyl, or straight or branched C$_2$-C$_6$ alkynyl);
wherein a salt of an acid selected from the group consisting of acetic acid, adipic acid, benzenesulfonic acid, benzoic acid, camphorsulfonic acid, citric acid, fumaric acid, hydroiodic acid, hydrobromic acid, hydrochloric acid, hydrochlorothiazide acid, hydroxy-naphthoic acid, lactic acid, maleic acid, methanesulfonic acid, methylsulfuric acid, 1,5-naphthalenedisulfonic acid, nitric acid, palmitic acid, pivalic acid, phosphoric acid, propionic acid, succinic acid, sulfuric acid, tartaric acid, terephthalic acid, p-toluenesulfonic acid, and valeric acid.

In another embodiment, the invention provides a method which further comprising administering as part of a combination therapy, a therapeutically effective amount of human chorionic gonadotropin.

In another embodiment, the invention provides a pharmaceutical composition comprising:
a) a pharmaceutically acceptable excipient, diluent or carrier;
b) a therapeutically effective amount of at least one sex steroid precursor or prodrug thereof; and
c) a therapeutically effective amount of at least one SERM, antiestrogen or prodrug.

In another embodiment, the invention provides a pill, a tablet, a capsule, a gel, a cream, an ovule, a rectal suppository, or an injection comprising:
a) a pharmaceutically acceptable excipient, diluent or carrier;
b) a therapeutically effective amount of at least one sex steroid precursor or prodrug thereof; and
c) a therapeutically effective amount of at least one SERM, antiestrogen or prodrug.

In another embodiment, the invention provides a kit comprising a first container containing a pharmaceutical formulation comprising a therapeutically effective amount of at least one sex steroid precursor or a prodrug thereof; and said kit further comprising a second container containing a pharmaceutical formulation comprising a therapeutically effective amount of at least one SERM, antiestrogen or prodrug as part of combination therapy.

In another embodiment, the invention pertains to a method of preventing, reducing or eliminating the incidence of male androgen deficiency symptoms or diseases including male hypogonadism-associated symptoms and diseases by increasing levels of a sex steroid precursor selected from the group consisting of dehydroepiandrosterone (DHEA), dehydroepiandrosterone-sulfate (DHEA-S), androst-5-ene-3β,17β-diol (5-diol) and 4-androstene-3,17-dione in a patient in need of said prevention, reduction or elimination of the incidence, and further comprising administering to said patient a therapeutically effective amount of at least one SERM, antiestrogen or prodrug as part of combination therapy.

In another embodiment, the invention pertains to a method of preventing, reducing or eliminating the incidence of male androgen deficiency symptoms or diseases including male hypogonadism-associated symptoms and diseases by increasing levels of circulating testicular testosterone by the action of SERM or antiestrogen in a patient in need of said prevention, reduction or elimination of the incidence, and further comprising administering to said patient a therapeutically effective amount of at least one sex steroid precursor or prodrug as part of combination therapy.

In another embodiment, the invention provides a method of preventing, reducing or eliminating the incidence of male androgen deficiency symptoms or diseases including male hypogonadism-associated symptoms and diseases by increasing the levels of circulating androgen metabolites consisting of androsterone glucuronide (ADT-G), androstane-3α,17β-diol-3-glucuronide (3α-diol-3G) and androstane-3α,17β-diol-17-glucuronide (3α-diol-17G), said method comprising administering to male patient in need of said prevention, reduction or elimination, a therapeutically effective amount of a sex steroid precursor or prodrug thereof in association with a therapeutically effective amount of a selective estrogen receptor modulator or an antiestrogen or prodrug of either.

As used herein, "Pure SERM" means that the SERM does not have any estrogenic activity in breast or uterine tissue at physiological or pharmacological concentrations.

In another embodiment, the invention provides a kit comprising a first container containing a therapeutically effective amount of at least one precursor of sex steroids and further comprising a second container containing a therapeutically effective amount of at least one SERM.

In another embodiment, the invention provides, in one container, a pharmaceutical composition comprising:
  a) a pharmaceutically acceptable excipient, diluent or carrier;
  b) a therapeutically effective amount of at least one precursor of sex steroids; and
  c) a therapeutically effective amount of at least one SERM.

In another embodiment, the invention provides a method of preventing, reducing or eliminating the incidence of male androgen deficiency symptoms or diseases including male hypogonadism-associated symptoms and diseases, said method comprising administering to male patient in need of said prevention, reduction or elimination, a therapeutically effective amount of a sex steroid precursor or prodrug thereof in association with a therapeutically effective amount of a selective estrogen receptor modulator or an antiestrogen or prodrug of either, wherein the selective estrogen receptor modulator or antiestrogen stimulates LH secretion which increases the level of circulating testosterone.

In another embodiment, the invention provides a pharmaceutical composition for preventing, reducing or eliminating the incidence of male androgen deficiency symptoms or diseases including male hypogonadism-associated symptoms and diseases comprising:
  a) a pharmaceutically acceptable excipient, diluent or carrier;
  b) at least one sex steroid precursor or prodrug thereof; and
  c) at least one selective estrogen receptor modulator or an antiestrogen or prodrug of either;
wherein said pharmaceutical composition is provided in packaging that directs use of said composition for prevention, reduction or elimination of at least one male androgen deficiency symptom or disease.

In another embodiment, the invention provides a kit for preventing, reducing or eliminating the incidence of male androgen deficiency symptoms or diseases including male hypogonadism-associated symptoms and diseases, comprising (i) a first container having therein at least one sex steroid precursor or a prodrug thereof; (ii) a second container having therein at least one selective estrogen receptor modulator, or an antiestrogen or prodrug of either of the foregoing; and (iii) instructions for using the kit for the prevention, reduction or elimination of at least one male androgen deficiency symptom or disease.

It is preferred that the sex steroid precursor is dehydroepiandrosterone and the selective estrogen receptor modulator is acolbifene.

As used herein, compounds administered to a patient "in association with" other compounds are administered sufficiently close to administration of said other compound that a patient obtains the physiological effects of both compounds simultaneously, even though the compounds were not administered in close time proximity. When compounds are administered as part of a combination therapy they are administered in association with each other. Preferred SERM (acolbifene) discussed herein is preferably used in combination with preferred sex steroid precursors dehydroepiandrosterone, dehydroepiandrosterone-sulfate, androst-5-ene-3β,17β-diol or 4-androstene-3,17-dione, especially dehydroepiandrosterone.

The applicant believes that the addition of a precursor of sex steroids to acolbifene treatment will increase intracellular levels of testosterone (as well demonstrated in patients with prostate cancer where intracellular androgens, especially dihydrotestosterone, is coming from endogenous DHEA (Labrie, Dupont et al. 1985; Labrie, Cusan et al. 2009; Labrie 2011)).

As used herein, a SERM is a compound that functions as an estrogen receptor antagonist (antiestrogen) in breast tissue, yet provides estrogenic or estrogen-like effect on bone tissue and on serum cholesterol levels (i.e. by reducing serum cholesterol). Non-steroidal compounds that function as estrogen receptor antagonists in vitro or in human or rat breast tissue (especially if the compound acts as an antiestrogen on human breast cancer cells) is likely to function as a SERM. Conversely, steroidal antiestrogens tend not to function as SERMs because they tend not to display any beneficial effect on serum cholesterol. Non-steroidal antiestrogens we have tested and found to function as SERMs include EM-800, EM-652.HCl, raloxifene, tamoxifen, 4-hydroxy-tamoxifen, toremifene, 4-hydroxy-toremifene, droloxifene, LY 353 381, LY 335 563, GW-5638, lasofoxifene, bazedoxifene (TSE 424; WAY-TSE 424; WAY 140424; 1-[[4[2-(hexahydro-1H-azepin-1-yl)ethoxy]phenyl]methyl]-2-(4-hydroxyphenyl)-3 methyl-1H-indol-5-ol), pipendoxifene (ERA 923; 2-(4-hydroxyphenyl)-3-methyl-1-[[4-[2-(1-piperidinyl)ethoxy]phenyl]methyl]-1H-indol-5-ol) ospemifene and idoxifene, but are not limited to these compounds.

But we have found also that all SERMs do not react in the same manner and may be divided into two subclasses: "pure SERMs" and "mixed SERMs". Thus, some SERMs like EM-800 and EM-652.HCl do not have any estrogenic activity in breast and endometrial tissues at physiological or pharmacological concentrations and have hypocholesterolemic and hypotriglyceridemic effects in the rat. These SERMS may be called "pure SERMs". The ideal SERM is a pure SERM of the type EM-652.HCl because of its potent and pure antiestrogenic activity in the mammary gland. Others, like raloxifene, tamoxifen, droloxifene, 4-hydroxy-tamoxifen (1-(4-dimethylaminoethoxyphenyl)-1-(4-hydroxylphenyl)-2-phenyl-but-1-ene), toremifene, 4-hydroxy-toremifene[(Z)-(2)-2-[4-(4-chloro-1-(4-hydroxyphenyl)-2-phenyl-1-butenyl)phenoxyl]-N,N-dimethylethanamine), LY 353 381, LY 335 563, GW-5638, lasofoxifene, idoxifene, bazedoxifene and ospemifene have some estrogenic activities in the breast and endometrium. This second series of SERMs may be called "mixed SERMs". The unwanted estrogenic activities of these "mixed SERMs" may be inhibited by addition of pure "SERMs" as shown in FIGS. 2 and 3 in vitro tests and in FIG. 4 in an in vivo test of breast cancer. Since human breast carcinoma xenografts in nude mice are the closest available model of human breast cancer, we have thus compared the effect of EM-800 and tamoxifen alone and in combination on the growth of ZR-75-1 breast cancer xenografts in nude mice.

In one embodiment, the invention uses selective estrogen receptor modulators of the following molecular structure

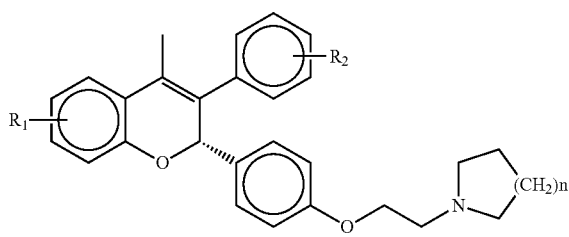

wherein R1 and R2 are independently hydrogen, hydroxyl or a moiety which is converted to hydroxyl in vivo, and n=1 or 2.

The applicant believes that it is very important that SERMs of the invention act as pure antiestrogens in breast because SERMs have to counteract potential side-effects of estrogens, particularly those formed from the exogenous precursors of sex steroids which can increase the proliferation of this tissue. Particularly, the applicant believes that benzopyran derivatives of the invention having the absolute configuration 2S at position 2 is more suitable than its racemic mixture. Thus, in U.S. Pat. No. 6,060,503, optically active benzopyran antiestrogens having 2S configuration are disclosed to treat estrogen-exacerbated breast and endometrial cancer and these compounds are shown to be significantly more efficient than racemic mixtures (See FIGS. 1-5 of U.S. Pat. No. 6,060,503).

The enantiomer of 2S configuration being difficult to be industrially obtained as a pure state, the applicant believes that less than 10%, preferably less than 5% and more preferably less than 2% by weight of contamination by the 2R enantiomer is preferred.

Prodrug forms of active pharmaceutical ingredient are well known in the art. See, e.g. H. Bundgaard "5. Design and Application of Prodrugs" (In A textbook of Drug Design and Development. Edited by P. Krogsgaard-Larsen and H. Bundgaard; Harwood Academic Publishers GmbH, Chur, Switzerland, 1991), the contents of which are incorporated herein by reference. In particular, see page 114 defining prodrug: a prodrug is a pharmacologically inactive derivative of a parent drug molecule that requires spontaneous or enzymatic transformation within the body in order to release the active drug, and that has improved delivery properties over the parent drug molecule. In the present application, the prodrugs of sex steroid precursor are derivatives of the 3- and/or 17-hydroxyl group(s) and/or 3- and/or 17-ketone group(s), and the prodrugs of selective estrogen receptor modulators and antiestrogens are derivatives of the hydroxyl group. The prodrug forms of the hydroxyl group are esters, carbonate esters, phosphate esters, ethers, and α-acyloxyalkyl ethers, and the prodrug forms of the ketone group are ketals, imines, enol esters, oxazolidines and thiazolidines but not limited by these examples (see page 154). The previous-cited SERM EM-800 (diester derivative, dipivaloate) is a prodrug of EM-652 (Gauthier, Caron et al. 1997).

Serum testosterone is higher in the morning and decreases to a minimum concentration after sleep (Trenell, Marshall et al. 2007). Serum testosterone should be monitored (with the judgment of the treating physician concerning its frequency) at months 1 and 2 of treatment and then every 3 months to assure proper increases in serum testosterone. Similar measurements should be made for DHEA. Serum DHEA also follows a circadian rythm being lowest in the morning. For proper comparison, it is preferable to measure serum testosterone and DHEA at the same time of the day at different treatment time intervals, i.e., at month 1 and 2 and then every 3 months.

BRIEF DESCRIPTION OF THE DRAWINGS

FIG. 12: Schematic representation of the role of testicular and adrenal sources of sex steroids in men and the effect of adding acolbifene to counteract the inhibitory effect of estrogens at the hypothalamo-pituitary level on the secretion of LH. ACTH, adrenocorticotropin; CRH, corticotropin-releasing hormone; DHEA, dehydroepiandrosterone; DHT, dihydrotestosterone; $E_2$, 17β-estradiol; LH, luteinizing hormone; GnRH, gonadotropin-releasing hormone.

DETAILED DESCRIPTION OF THE INVENTION

Beneficial Effects of DHEA

We feel that the increased understanding of androgen and estrogen formation and action in peripheral target tissues called intracrinology (Labrie 1991; Labrie, Simard et al. 1992a; Labrie, Simard et al. 1992b; Labrie, Simard et al. 1994; Labrie, Durocher et al. 1995; Luu-The, Dufort et al. 1995; Labrie, Simard et al. 1996b; Labrie, Bélanger et al. 1997a; Labrie, Bélanger et al. 1997b; Labrie, Diamond et al. 1997b; Labrie, Luu-The et al. 1997) as well as our recent observations indicating the predominant role of androgens over that of estrogens in the prevention of bone loss after ovariectomy in the rat (Martel, Sourla et al. 1998) and the observation of a similar situation in postmenopausal women (Labrie, Diamond et al. 1997a) have paved the way for a timely and potentially highly significant progress in the field of sex steroid replacement therapy and aging. Such a possibility is well supported by our observations.

The present invention is thus based upon the recent progress achieved in our understanding of sex steroid physiology in men and women (Labrie 1991; Labrie, Simard et al. 1992a; Labrie, Simard et al. 1992b; Labrie, Simard et al. 1994; Labrie, Durocher et al. 1995; Luu-The, Dufort et al. 1995; Labrie, Simard et al. 1996b; Labrie, Bélanger et al. 1997a; Labrie, Bélanger et al. 1997b; Labrie, Diamond et al. 1997b; Labrie, Luu-The et al. 1997).

The pool of androgens in men decreases progressively from the age of 30 years in parallel with the decrease in the serum concentration of DHEA and DHEA-S (Labrie, Bélanger et al. 1997b). Since serum DHEA is responsible for up to 50% of the androgens present in peripheral tissues (Labrie, Dupont et al. 1985; Labrie, Cusan et al. 2009; Labrie 2010b; Labrie 2011) such a decrease of the biosynthesis of androgens from DHEA with aging is likely to play an important role in the appearance of LOH (Late Onset Hypogonadism) and all the problems mentioned earlier related to low androgens.

Figure 1:
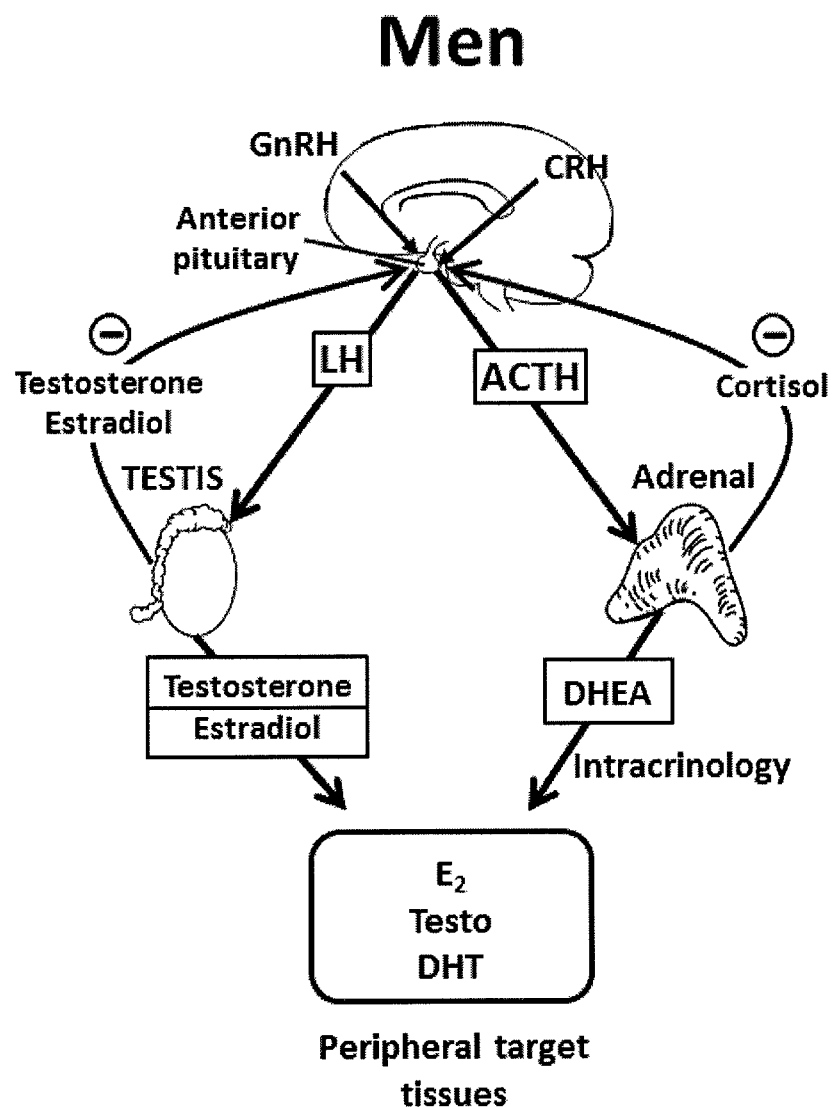
FIG. 1 is a schematic representation of the hypothalamo-pituitary-testicular and hypothalamo-pituitary-adrenal axes. GnRH, gonadotropin-releasing hormone; CRH, corticotropin-releasing hormone; LH, luteinizing hormone; ACTH, adrenocorticotropin; DHEA, dehydroepiandrosterone; $E_2$, estradiol; DHT, dihydrotestosterone; Testo, testosterone.
Figure 2:
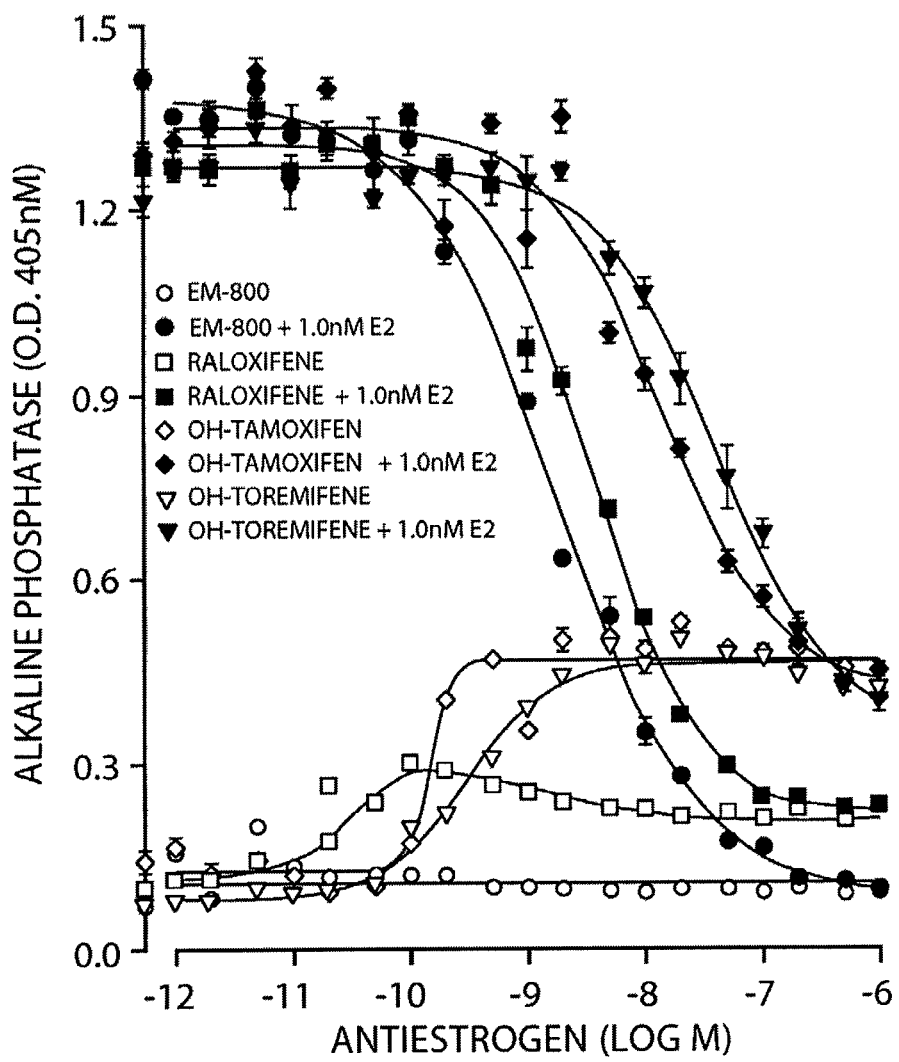
FIG. 2 shows the effect of increasing concentrations of EM-800 (prodrug of acolbifene, free salt), (Z)-4-OH-tamoxifen, (Z)-4-OH-toremifene and raloxifene on alkaline phosphatase activity in human endometrial cancer Ishikawa cells. Alkaline phosphatase activity was measured after a 5-day exposure to increasing concentrations of indicated compounds in the presence or absence of 1.0 nM $E_2$. The data are expressed as the means±SEM of four wells. When SEM overlaps with the symbol used, only the symbol is shown (Simard, Sanchez et al. 1997).
Figure 3:
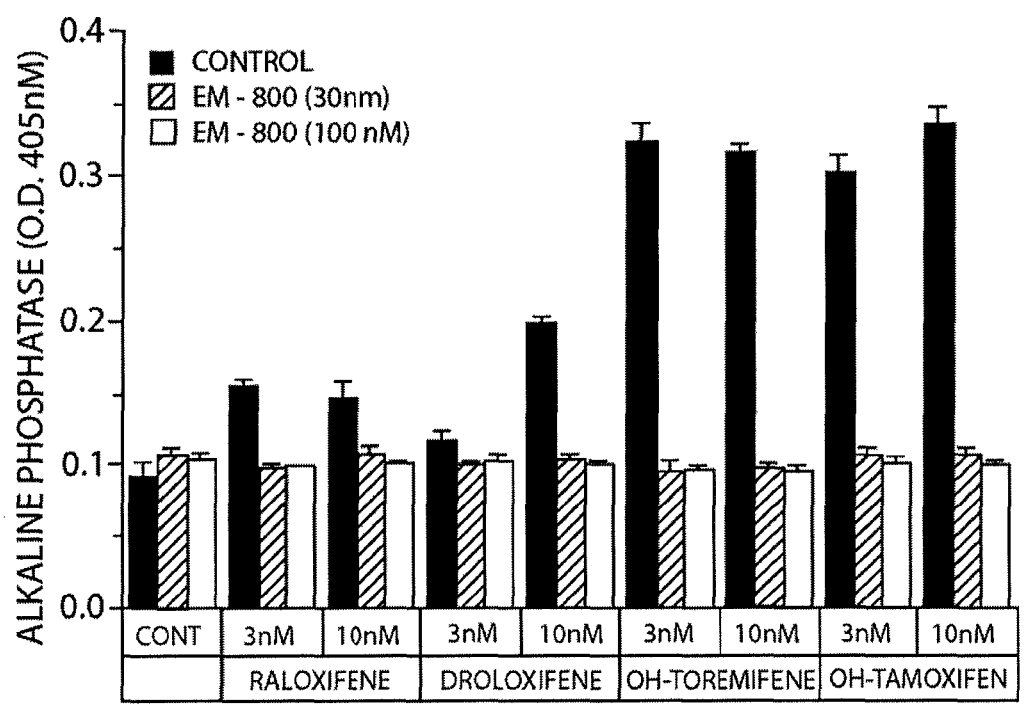
FIG. 3 shows the blockade of the stimulatory effect of (Z)-4-OH-tamoxifen, (Z)-4-OH-toremifene, droloxifene and raloxifene on alkaline phosphatase activity by the antiestrogen EM-800 (prodrug of acolbifene, free salt) in human Ishikawa (endometrial) carcinoma cells. Alkaline phosphatase activity was measured after a 5-day exposure to 3 or 10 nM of the indicated compounds in the presence or absence of 30 or 100 nM EM-800. The data are expressed as the means±SD of eight wells with the exception of the control groups were data are obtained from 16 wells (Simard, Sanchez et al. 1997).
Figure 5:
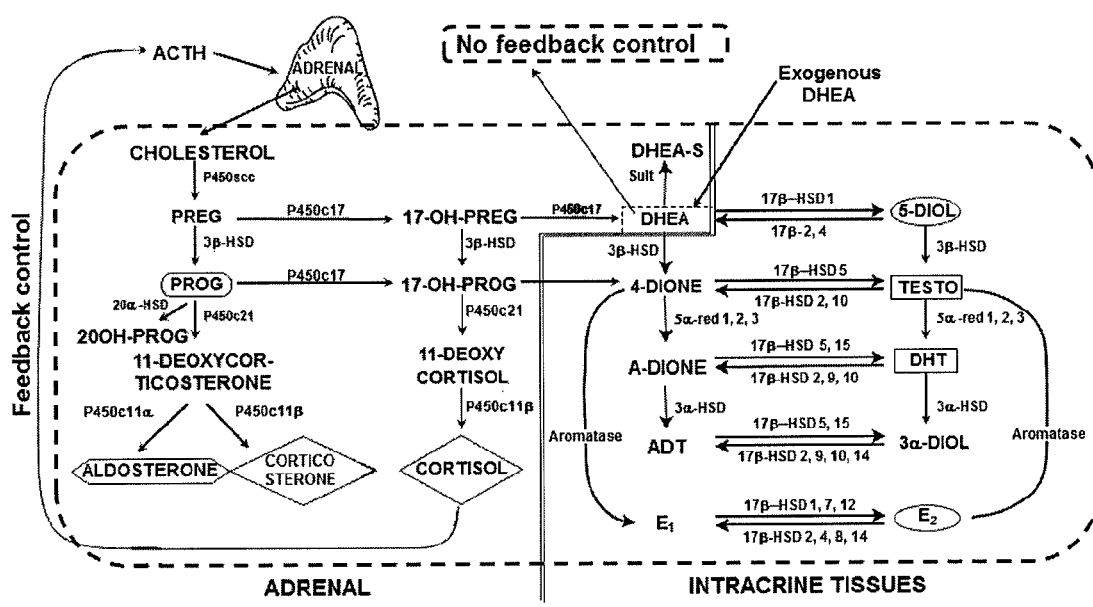
FIG. 5. Schematic representation of the adrenal and intracrine steroidogenic pathways, DHEA, dehydroepiandrosterone; DHEA-S, DHEA-sulphate; DHT, dihydrotestosterone; HSD, hydroxysteroid dehydrogenase.

DHEA, an Important Source of Peripheral Androgens Made by the Intracrine Mechanisms in Men Humans, with some other primates, are unique among animal species in having adrenals that secrete large amounts of the inactive precursor steroids DHEA and DHEA-S, which are converted into potent androgens and/or estrogens in peripheral tissues. It is remarkable that man, in addition to possessing very sophisticated endocrine and paracrine systems, has largely invested in sex steroid formation in peripheral tissues (Labrie, Dupont et al. 1985; Labrie, Bélanger et al. 1988; Labrie 1991; Labrie, Bélanger et al. 1997a) (FIGS. 1, 2 and 5).

In men, the 95% (or more) fall in serum testosterone induced by castration and the clinical benefits of this partial elimination of androgens with advanced prostate cancer (Huggins and Hodges 1941) have led to erroneously believe that castration eliminates 95% (or more) of androgens and that castration alone is an appropriate treatment for prostate cancer.

In men, the finding that 25-50% of androgens are left in the prostate after castration (Labrie, Dupont et al. 1985; Bélanger, Bélanger et al. 1989; Nishiyama, Hashimoto et al. 2004; Mostaghel, Page et al. 2007) explains why the addition of a pure (non-steroidal) anti-androgen to castration achieves a more complete blockade of androgens and has been the first treatment shown to prolong life in prostate cancer (Labrie, Dupont et al. 1982; Labrie, Dupont et al. 1985; Caubet, Tosteson et al. 1997; Prostate Cancer Trialists' Collaborative Group 2000; Labrie, Bélanger et al. 2005). The androgens remaining at relatively high levels after castration also explain why combined androgen blockades or the blockade of the androgens of both testicular and adrenal origins at start of treatment can provide cure for most patients when the treatment is started at the localized stage of the cancer (Labrie, Candas et al. 2002; Akaza 2006; Ueno Namiki et al. 2006), thus clearly demonstrating the major role of extratesticular androgens or intracrinology in men.

Transformation of the adrenal precursor steroid DHEA into androgens and/or estrogens in peripheral target tissues depends upon the levels of expression of the various steroidogenic and metabolizing enzymes in each cell of these tissues. This situation of a high secretion rate of adrenal precursor sex steroids in men and women is thus completely different from all animal models used in the laboratory (namely rats, mice, guinea pigs and all others except monkeys), where the secretion of sex steroids takes place exclusively in the gonads (Labrie, Dupont et al. 1985; Labrie, Bélanger at al. 1988; Bélanger, Bélanger et al. 1989; Labrie, Bélanger et al. 1997a).

The androgens testosterone and DHT as well as $E_2$ made in peripheral tissues from DHEA of adrenal origin exert their action locally in the same cells where their synthesis takes place (FIG. 5). This sophisticated mechanism permits to maintain biologically active levels of intracellular estrogens and/or androgens in specific tissues in need of these sex steroids while the same steroids leak in the blood at very low levels, thus sparing the other tissues from a potentially negative influence. Following their cell-specific local formation and immediate availability for local intracellular action, testosterone and DHT (the most active natural androgen) and $E_2$ are inactivated and transformed in the same cells into water-soluble glucuronide or sulphate derivatives which can then diffuse quantitatively into the general circulation where they can be measured by mass spectrometry (Labrie, Bélanger et al. 2006) before their elimination by the kidneys.

It should also be noted that the importance of the intracrine formation of androgens and estrogens extends to non-malignant diseases such as acne, seborrhoea, hirsutism and androgenic alopecia as well as to osteoporosis and vulvovaginal atrophy (Cusan, Dupont et al. 1994; Labrie, Bélanger et al. 1997a; Labrie, Archer et al. 2009b; Labrie, Archer et al. 2009a; Labrie, Archer et al. 2009c). Practically all tissues possess, at various levels, a battery of steroidogenic enzymes that can transform DHEA. Each tissue, however, possesses a highly tissue-specific set of steroidogenic and steroid-inactivating enzymes which require experimentation to be known.

Figure 4:
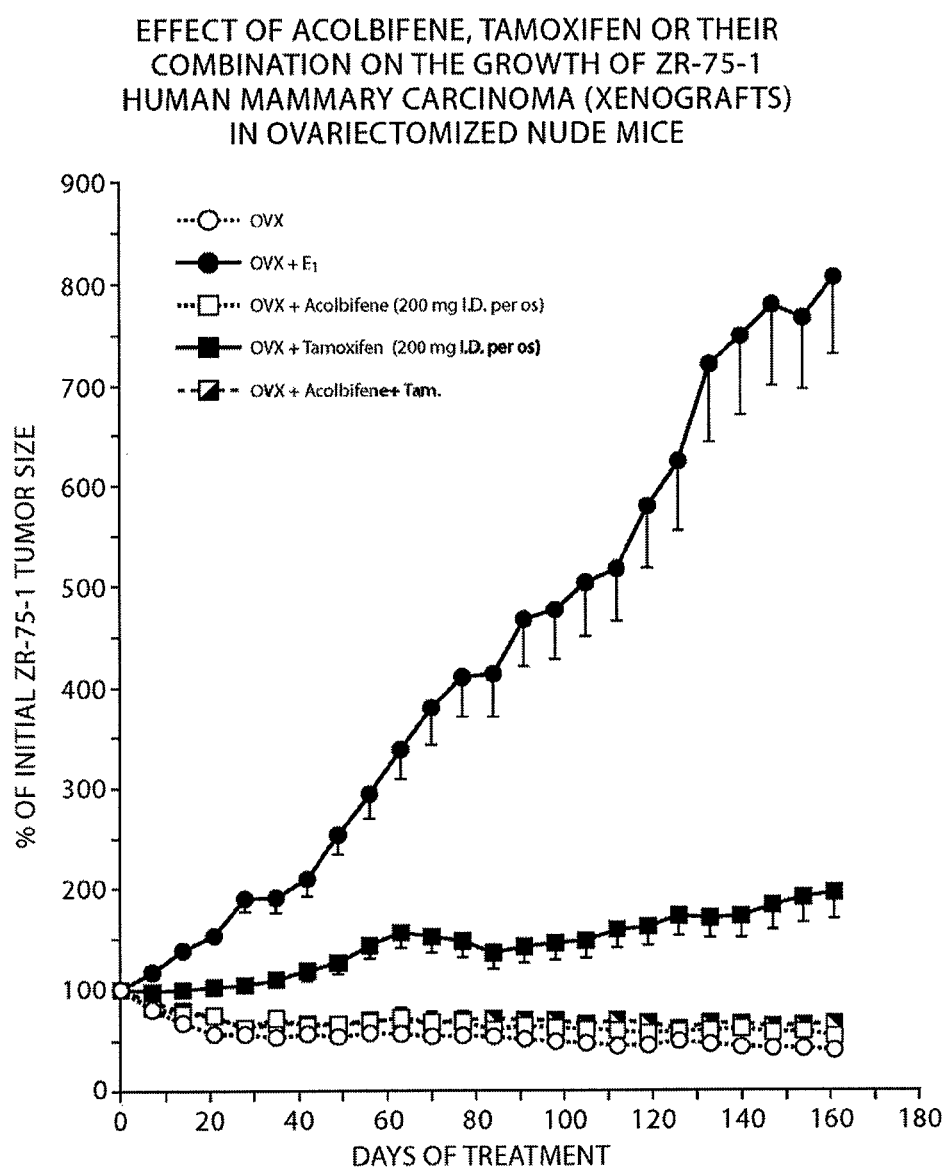
FIG. 4 shows that the stimulatory effect of tamoxifen on the growth of human breast cancer ZR-75-1 xenografts is completely blocked by simultaneous administration of EM-652.HCl (acolbifene). Acolbifene, by itself, in agreement with its pure antiestrogenic activity has no effect on tumor growth in the absence of tamoxifen.

While the serum levels of testosterone are reduced by 97.4% following castration in 69-80-year-old men (Labrie, Cusan et al. 2009), the sum of the metabolites of androgens, the only accurate and valid parameter of total androgenic activity measurable in the circulation (Labrie, Bélanger et al. 2006), is only reduced by 58.9% (Labrie, Cusan et al. 2009), thus indicating that a very important proportion (41.1%) of androgens remains in men after complete elimination of testicular androgens. Such data are in close agreement with the concentration of intraprostatic DHT that shows that, on average, 39% of DHT is left in the prostate after castration in various studies, namely 45% (Labrie, Dupont et al. 1985), 51% (Bélanger, Brochu et al. 1986), 25% (Nishiyama, Hashimoto at al. 2004) and 35% (Mostaghel, Page et al. 2007) (see FIG. 4 in (Labrie 2010b)).

Figure 6:
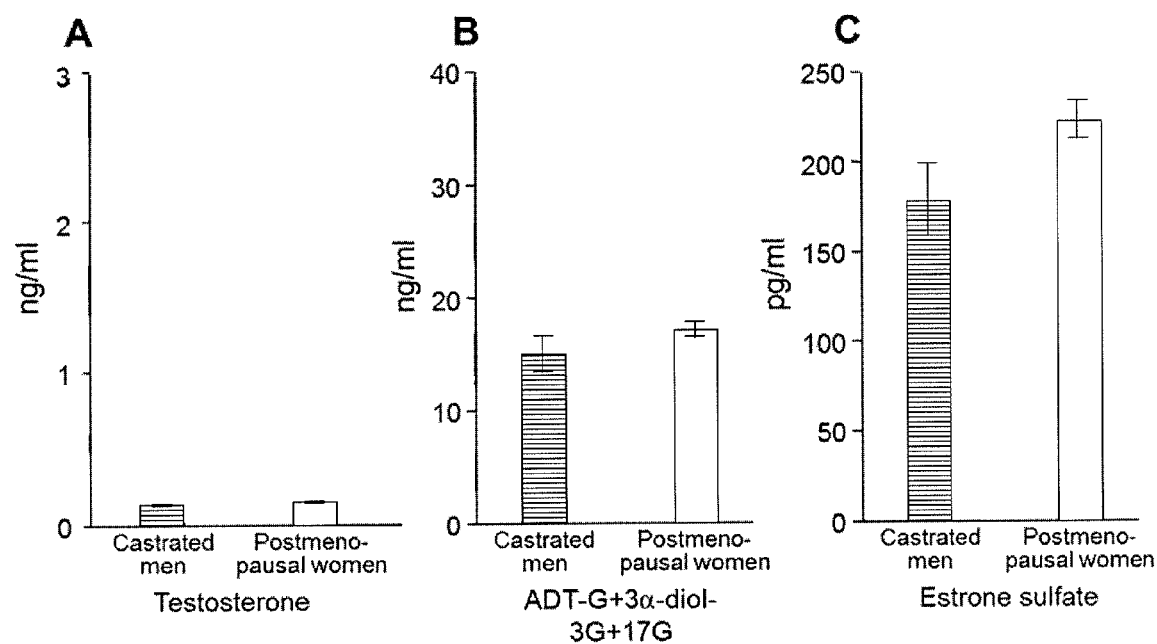
FIG. 6. Comparison of the serum concentrations of testosterone (A), total androgenic pool (sum of ADT-G, 3α-diol-3G and 3α-diol-17G) (B) and $E_1S$ (C) in castrated 69-80-year-old men (n=34) and intact 55-65-year-old postmenopausal women (n=377) (Labrie, Bélanger et al. 2006; Labrie, Cusan et al. 2009).

With the knowledge of the major importance of androgens of adrenal origin in men, it is of interest to compare the data mentioned above for men with the serum levels of the same steroids measured in intact postmenopausal women. As can be seen in FIGS. 6A and 6B, the serum levels of testosterone and of the total androgen metabolites are almost superimposable in castrated men and postmenopausal women of comparable age. Most interestingly, it can also be seen that the serum levels of estrone sulphate ($E_1S$) are also comparable (FIG. 6C). It could also be seen that the serum levels of $E_1$ and $E_2$ are also comparable, thus indicating that similar amounts of estrogens of adrenal origin are found in both men and women (Labrie, Cusan et al. 2009).

The above-summarized data show that ~40% of androgens are made in peripheral tissues in the absence of testicles in 69-80-year-old men. Since serum DHEA decreases markedly with age starting in the thirties (Labrie, Dupont et al. 1985), and testicular androgen secretion decreases only slightly, it is most likely that androgens of adrenal origin have an even greater relative and absolute importance at younger ages.

As mentioned above, the local synthesis and action of sex steroids in peripheral target tissues has been called intracrinology (Labrie, Bélanger et al. 1988; Labrie 1991). Recent and rapid progress in this area has been made possible by the elucidation of the structure of most of the tissue-specific genes that encode the steroidogenic enzymes responsible for the transformation of DHEA-S and DHEA into androgens and/or estrogens locally in peripheral tissues (Labrie, Simard et al. 1992a; Labrie, Sugimoto et al. 1992; Labrie, Durocher et al. 1995; Luu-The, Zhang et al. 1995; Labrie, Simard et al. 1996a; Labrie, Luu-The et al. 1997) (FIG. 5).

The major importance of DHEA and DHEA-S in human sex steroid physiology is illustrated by the estimate that up to 50% of total androgens in adult men derive from these adrenal precursor steroids (Labrie, Dupont et al. 1985; Bélanger, Brochu et al. 1986; Labrie, Bélanger et al. 1993).

Concerning the breast, DHEA is known to prevent the development (Luo Sourla et al. 1997) and to inhibit the growth (Li, Yan et al. 1993) of dimethylbenz(a)anthracene mammary tumors in the rat. DHEA, in addition, inhibits the growth of human breast cancer xenografts in nude mice (See example 1 and (Couillard, Labrie et al. 1998). Thus, contrary to estrogens and progestins which exert stimulatory effects, DHEA is expected to inhibit both the development and the growth of breast cancer in women.

As well demonstrated in our previous studies, supplementation with physiological amounts of exogenous DHEA permits the biosynthesis of androgens and estrogens only in the appropriate target tissues which contain the specific steroidogenic enzymes. The active androgens and estrogens thus synthesized remain in the cells of origin and very little leakage occurs into the circulation.

In fact, the most striking effects of DHEA administration are on the circulating levels of the glucuronide derivatives of the metabolites of DHT, namely ADT-G and 3α-diol-G, these metabolites being produced locally in the peripheral intracrine tissues which possess the appropriate steroidogenic enzymes to synthesize DHT from the adrenal precursors DHEA and DHEA-S and, thereafter, to further metabolize DHT into inactive conjugates (Labrie 1991; Labrie, Simard et al. 1996a). This local biosynthesis and action of androgens in target tissues eliminates the exposure of other tissues to androgens and thus minimizes the risks of undesirable masculinizing or other androgen-related side effects. The same applies to estrogens although we feel that a reliable parameter of total estrogen secretion (comparable to the glucuronides for androgens) is not yet available.

DHEA, Muscle and Lean Body Mass

Since 40-50% of androgens in 60-70-year-old men originate from adrenal DHEA (Labrie, Cusan et al. 2009), it is reasonable to believe that adrenal DHEA has an importance comparable to testicular testosterone in the control of muscle mass and strength in men.

There is no doubt that androgens play the predominant role in muscle growth, development and function. Androgens are well known to increase muscle mass in normal men (Bhasin, Storer et al. 1996; Bhasin, Woodhouse et al. 2001), this effect being related to the ban of androgens by the International Olympic Committee. In fact, the major form of sports doping remains androgenicanabolic abuse. At suitable doses, exogenous androgens enhance muscle mass and strength in all men and women athletes (Handelsman 2006). As a result, since the early 1970s, exogenous androgens have been banned for men and women in sports.

The marked decline in serum DHEA in aging women and men has led to the suggestion that a series of changes associated with aging, including loss of muscle mass and strength, may be due to declining DHEA with age (Labrie, Bélanger et al. 1998; Lamberts 2003). The beneficial effects of DHEA in rodents on body composition are well known (Tagliaferro, Davis at al. 1986; Han, Hansen et al. 1998). Several age-related changes observed in men, especially loss of muscle and bone mass, as well as sexual function and increase in fat mass are similar to those observed in androgen deficiency (Matsumoto 2002; Morley and Perry 2003).

Based on cross-sectional data, maximal muscle strength at the age of 70 years is 30-50% of peak muscle strength found at the age of 30 years (Murray and Pitt 1985; Kallman, Plato et al. 1990). The age associated muscle strength loss seems to be correlated with a reduced cross-sectional area of the muscles (Larsson, Grimby at al. 1979; Kallman, Plato et al. 1990). Age-related sarcopenia increases the risk of falls, fractures, disability and life-threatening complications (Evans 1997; Frontera, Hughes et al. 2000; Melton, Khosla et al. 2000; Hughes, Frontera et al. 2002; Iannuzzi-Sucich, Prestwood et al. 2002).

Following studies where apparently too low doses of testosterone were used (Elashoff, Jacknow et al. 1991), a series of recent studies have unequivocally demonstrated a dose-response stimulatory effect of androgens on muscle size and strength (Bhasin, Storer et al. 1996; Bhasin, Storer et al. 1997; Bross, Casaburi et al. 1998; Bhasin, Woodhouse et al. 2001; Storer, Magliano et al. 2003; Bhasin, Woodhouse et al. 2005) have compared the efficacy of increasing doses of testosterone on androgen-sensitive parameters in 60-75-year-old and 19-35-year-old men. All men were treated with a GnRH agonist to eliminate endogenous and variable levels of testicular androgens. The weekly doses of testosterone enanthate were 25, 50, 125, 300 and 600 mg for 20 weeks. The effects observed in both young and old men were dose related. The increases in fat-free mass and muscle strength were correlated with the testosterone dose and were not different in old and young men. The best tolerance was achieved with the 125 mg dose, a dose giving high normal serum testosterone levels, low levels of adverse effects and an increase in fat-free mass and muscle strength (Bhasin, Woodhouse et al. 2005). The effects of androgens on the muscle are well recognized in hypogonadal men (Bhasin, Storer et al. 1997; Snyder, Peachey et al. 2000) and men receiving glucocorticoid therapy (Crawford, Liu et al. 2003).

In a study of 558 men aged 20-95 years, serum DHEA-S was found to be an independent predictor of muscle strength and mass in men aged 60-79 years (Valenti, Denti et al. 2004). These results are in agreement with another study showing a correlation between serum DHEA-S and muscle power (Kostka, Arsac et al. 2000; Bonnefoy, Patricot et al. 2002).

The administration of a daily dose of 50 or 100 mg DHEA for 6 or 12 months, respectively, improved knee extension strength in older men (Yen, Morales et al. 1995). No significant effect, however, was found following the administration of DHEA in 60-80-year-old women but the number of subjects was small. Muscle mass increase following DHEA administration has been observed by (Yen, Morales et al. 1995; Diamond, Cusan et al. 1996; Morales, Haubrich et al. 1998; Gebre-Medhin, Husebye et al. 2000; Villareal, Holloszy et al. 2000; Gordon, Grace et al. 2002; Johannsson, Burman et al. 2002) while others found no significant effect (Yen, Morales et al. 1995; Callies, Fassnacht et al. 2001; Percheron, Hogrel et al. 2003) in women.

Lean body mass has been reported to be increased by DHEA treatment (Diamond, Cusan et al. 1996; Morales, Haubrich et al. 1998; Gebre-Medhin, Husebye et al. 2000; Villareal, Holloszy et al. 2000; Nair, Rizza et al. 2006; Gurnell, Hunt et al. 2008).

Postural imbalance and falls are increasingly associated with hip fractures during aging (Cummings and Nevitt 1989). In fact, it is estimated that 80% of fractures in the elderly occur in the absence of peripheral osteoporosis (Siris, Chen et al. 2004) Such data stress the major importance of preventing falls in older adults by maintaining muscle mass and strength (Chang, Morton et al. 2004). A large proportion of fractures thus result from falls due to loss of muscle mass and strength which should be preventable, up to an unknown extent, by appropriate DHEA replacement.

Role of Androgens and Estrogens in Bone Physiology

A predominant role of androgens on bone physiology is well documented (Labrie, Diamond et al. 1997b; Martel, Sourla et al. 1998) In fact, both testosterone and DHT increased the transcription of α (I) procollagen mRNA in osteoblast-like osteosarcoma cells (Benz, Haussler et al. 1991). Treatment with DHT has also been shown to stimulate endochondral bone development in the orchiectomized rat (Kapur and Reddi 1989). Moreover, bone mineral density measured in the lumbar spine, femoral trochanter and total body was increased more by estrogen+testosterone implants than by $E_2$ alone over a 24-month treatment period in postmenopausal women (Davis, McCloud et al. 1995).

Moreover, in established osteoporosis, anabolic steroids have been reported to help prevent bone loss (Hennernan and Wallach 1957). Similarly, subcutaneous $E_2$ and testosterone implants have been found to be more efficient than oral estrogen in preventing osteoporosis in postmenopausal women (Savvas, Studd et al. 1988). Although the difference observed in that study has been attributed to the different routes of administration of the estrogen, the cause of the difference could well be the action of testosterone. As index of increased bone formation, an increase in serum osteocalcin, a marker of bone formation has been found in postmenopausal women receiving methyltestosterone plus estrogen, compared with estrogen alone (Raisz, Wiita et al. 1996). A similar stimulatory effect on serum osteocalcin has been observed following treatment of postmenopausal women with percutaneous DHEA for 12 months (Labrie, Diamond et al. 1997a). Moreover, androgen therapy, as observed with nandrolone decanoate, has been found to increase vertebral bone mineral density in postmenopausal women (Need, Horowitz et al. 1989). Although androgens are gaining increasing support due to their unique actions in postmenopausal women, virilizing effects are observed with the use of testosterone (Burger, Hailes et al. 1984; Studd, Collins et al. 1977).

Figure 7:
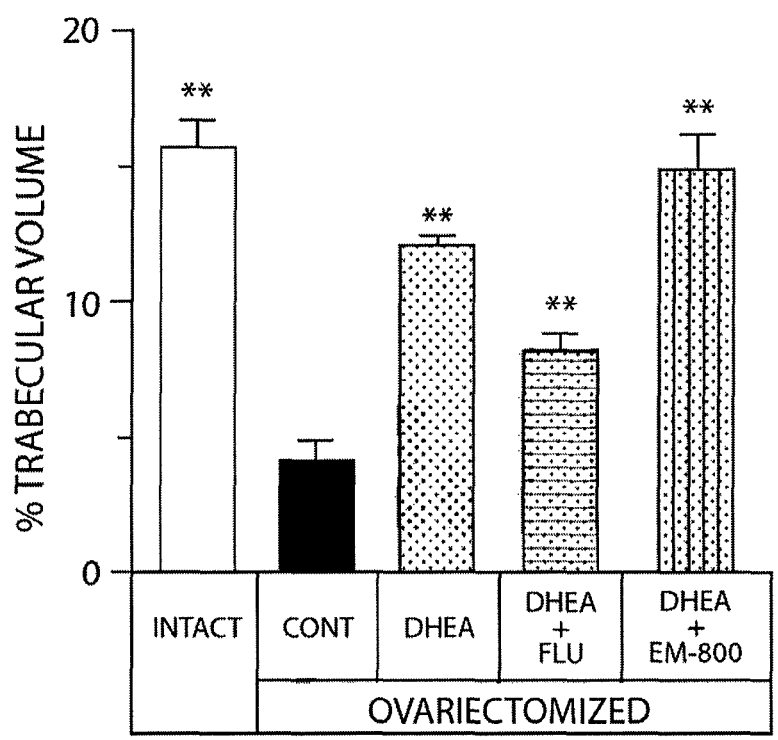
FIG. 7 shows the effect of 12-month treatment with dehydroepiandrosterone (DHEA) alone or in combination with Flutamide or EM-800 (prodrug of acolbifene, free salt) on trabecular bone volume in ovariectomized rats. Intact animals are added as additional controls. Data are presented as mean±SEM**p<0.01 versus OVX Control.
Figure 8:
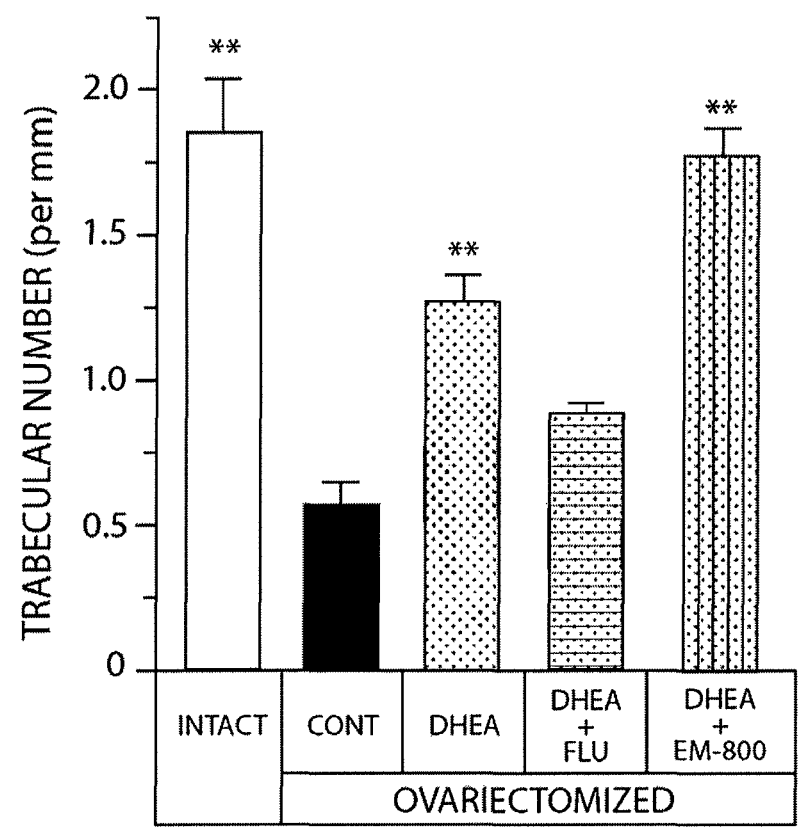
FIG. 8 shows the effect of 12-month treatment with dehydroepiandrosterone (DHEA) alone or in combination with Flutamide or EM-800 (prodrug of acolbifene, free salt) on trabecular number in ovariectomized rats. Intact animals are added as additional controls. Data are presented as mean±SEM**p<0.01 versus OVX Control.
Figure 9:
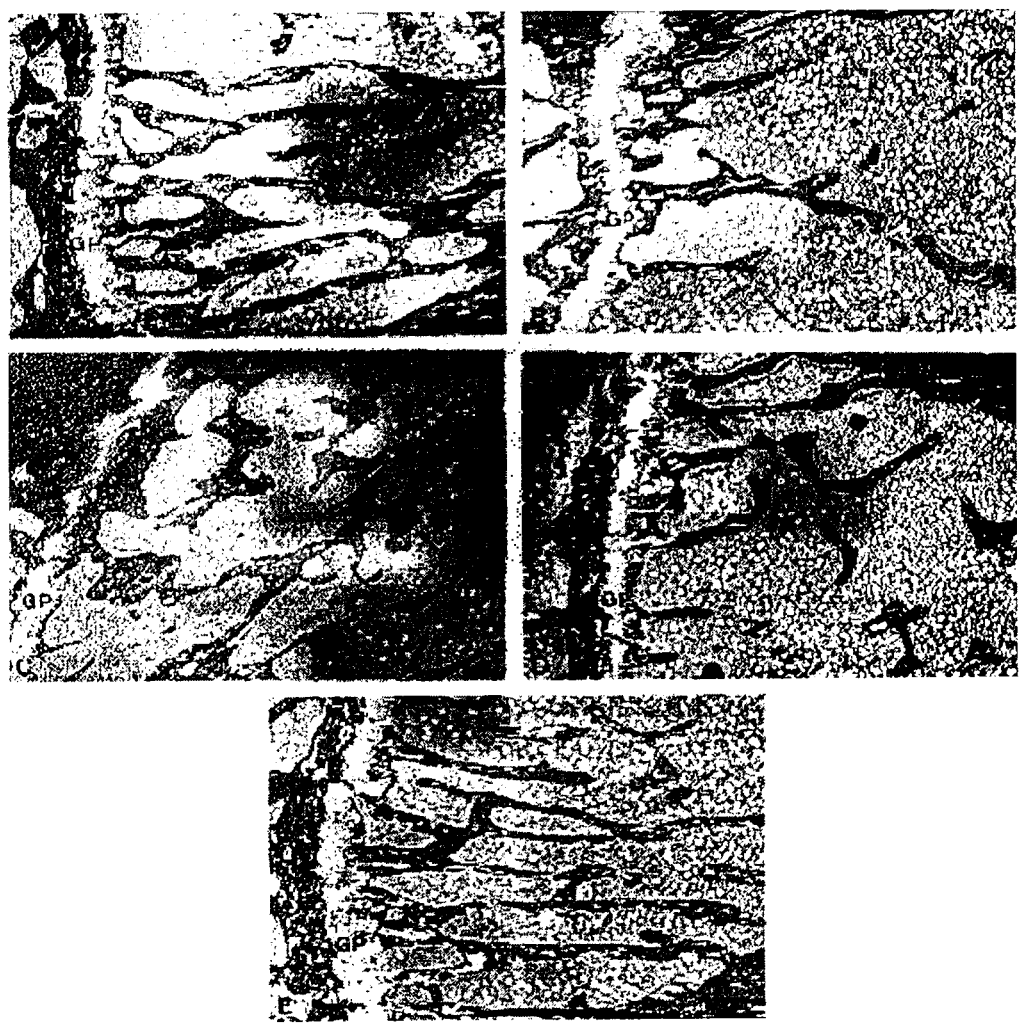
FIG. 9 shows proximal tibia metaphyses from intact control (A), ovariectomized control (B), and ovariectomized rats treated with DHEA alone (C) or in combination with Flutamide (D) or EM-800 (prodrug of acolbifene, free salt) (E). Note the reduced amount of trabecular bone (T) in ovariectomized control animals (B), and the significant increase in trabecular bone volume (T) induced after DHEA administration (C). The addition of Flutamide to DHEA partially blocked the effect of DHEA on the trabecular bone volume (D), whereas the combination of DHEA and EM-800 (prodrug of acolbifene, free salt) provided complete protection against the ovariectomy-associated bone loss. Modified trichrome Masson-Goldner, magn.×80. T: Trabeculae, GP: Growth Plate.

We have shown that DHEA exerts beneficial effects on bone in both the female rat (Luo, Sourla et al. 1997), and postmenopausal women (Labrie, Diamond et al. 1997a). Thus, in intact female rats, treatment with DHEA increases bone mineral density (BMD) of total skeleton, lumbar spine and femur (Luo, Sourla et al. 1997) (FIGS. 7, 8 and 9).

That the SERMs raloxifene and toremifene increase bone mineral density has been demonstrated (Smith 2006). Clomiphene citrate has shown positive results on serum testosterone and symptoms/signs of hypogonadism (Shabsigh, Kang et al. 2005; Whitten, Nangia et al. 2006).

DHEA and Abdominal Obesity

Abdominal obesity is associated with an increased risk of insulin resistance, type 2 diabetes and atherosclerosis (Shimokata, Tobin et al. 1989; Cefalu, Wang et al. 1995; Ferrannini, Natali et al. 1997; Kopelman 2000). Among other factors, hormonal changes, especially the declining secretion of DHEA and DHEA-S by the adrenals is thought to be a factor involved (Tchernof, Labrie et al. 1996). In rat and mouse models, DHEA administration reduces visceral fat accumulation in diet-induced (Yen, Allan et al. 1977; Cleary and Zisk 1986; Mohan, Ihnen et al. 1990; Hansen, Han et al. 1997) obesity. A beneficial effect of DHEA has also been observed on the decrease in insulin resistance that occurs with age (Han, Hansen et al. 1998).

In a study performed in postmenopausal women who received a DHEA cream for 12 months, we have found that insulin resistance was decreased while subcutaneous fat at the level of the thigh was also decreased (Diamond, Cusan et al. 1996). Moreover, the daily administration of 50 mg DHEA for 6 months in 65 to 78-year-old men and women decreased abdominal visceral fat by 10.2% in women and 7.4% in men (Villareal and Holloszy 2004). In the same study, abdominal subcutaneous fat was decreased by 6% in both women and men. Moreover, the responsiveness of serum insulin to the glucose tolerance test was decreased by 13% with no change in the glucose response, thus leading to a 34% improvement in the insulin sensitivity index following DHEA administration. An improvement in DHEA action has also been found in middle-aged men suffering from hypercholesterolemia (Kawano, Yasue et al. 2003).

In a previous study performed by the same group, DHEA administration for 6 months decreased total body fat mass by 1.4 kg while fat-free mass was increased by 0.9 kg (Villareal, Holloszy et al. 2000).

Of 25 randomized small size clinical trials enrolling 1353 elderly men with a men follow-up of 36 weeks, DHEA was associated with a decrease of fat mass which was strictly associated with its conversion into its biologically active androgen metabolites (Corona, Rastrelli et al. 2013). No significant effect was seen on lipid and glycemic metabolism, bone, sexual function and quality of life.

DHEA and Sexual Function

Community-based studies suggest self-reported sexual dysfunctions in women which range from 8% to 50%. In fact, low libido and sexual dysfunction increases with age in women from the third decade (Laumann, Paik et al. 1999) as well as after ovariectomy (Nathorst-Boos and von Schoultz 1992). While phychosocial and health factors are involved in low arousal and sexual desire (Dennerstein, Dudley et al. 1997) it is believed that low androgens play an independent role (Bachmann, Bancroft et al. 2002; Miller, Rosner et al. 2004).

Androgens are known to play a role in women's arousability, pleasure as well as intensity and ease of orgasm. Androgens are also involved in the neurovascular smooth muscle response of swelling and increased lubrication (Basson 2004).

In addition, the detailed benefits of androgens added to ERT or HRT have been described on general well-being, energy, mood, and general quality of life (Sherwin and Gelfand 1985; Sherwin 1988). Improvements in the major psychologic and psychomatic symptoms, namely irritability, nervousness, memory, and insomnia have been observed following addition of androgens to estrogen replacement therapy (ERT) (Notelovitz, Watts et al. 4-9-94-1992).

Loss of libido and/or sexual satisfaction are common in early postmenopause. The addition of androgens to hormone replacement therapy (HRT) is known to have beneficial effects on these problems. (Shifren, Braunstein et al. 2000) have found that transdermal testosterone administered by patch improved sexual frequency, pleasure and mood in surgically menopausal women. The effect was seen at a daily 300 μg dose of testosterone, a dose that led to serum testosterone levels in the upper limit of normal. Testosterone treatment has also been studied in non androgen-deficient women complaining of decreased libido (Goldstat, Briganti et al. 2003). Such treatment with testosterone improved libido, sexual function as well as quality of life compared to placebo. Similarly, in menopausal women with normal levels of androgens, the addition of methyltestosterone to estrogen increased sexual desire and frequency as compared to estrogen alone (Lobo, Rosen et al. 2003). Among women with dysfunction of sexual interest, desire, androgen therapy has been suggested for those having free serum testosterone levels within the lower quantile of the reference range (Bachmann, Bancroft et al. 2002). In fact, there is increased use of testosterone to treat hypoactive sexual desire disorder (HSDD) (Sherwin and Gelfand 1987; Davis, McCloud et al. 1995; Shifren, Braunstein et al. 2000; Goldstat, Briganti et al. 2003). These randomized clinical trials demonstrate that testosterone is effective in women with HSDD.

A clear example of nature of androgen deficiency of adrenal origin is provided by cases of adrenal insufficiency. (Arlt, Callies et al. 1999) have studied the effect of DHEA, 50 mg daily and placebo for 4 months in a population of women suffering from adrenal insufficiency. Treatment with DHEA raised serum testosterone in the low normal range. Such treatment increased the frequency of sexual thoughts, interest and satisfaction. Well-being, depression and anxiety were also improved. In a study where DHEA was administered at a high 300 mg daily dose, a greater subjective mental ($p<0.016$) and physical ($p<0.030$) was observed in response to an erotic video (Hackbert and Heiman 2002).

Since it is now understood that serum testosterone does not reflect the total androgen pool (Labrie, Bélanger et al. 2006), it is not surprising that serum testosterone needs to be increased to supraphysiological levels to improve sexual function since the serum levels represent only a fraction of total androgens, which are up to 50% made intracellularly and not reflected by circulating testosterone levels.

Since androgens appear so crucial for sexual dysfunction in women and practically 100% of androgens in women originate from DHEA (Labrie 2010a; Labrie, Martel et al. 2011) and women benefit from DHEA administration (Labrie, Archer et al. 2009a), it is reasonable to believe that DHEA administration in men having symptoms of loss of libido and sexual dysfunction (or other symptoms of androgen deficiency) in the presence or absence of low serum testosterone will similarly have beneficial effects from DHEA administration.

DHEA and Cardiovascular Disease

There is convincing evidence that androgens have beneficial effects on cardiovascular disease (CVD) in men (Alexandersen, Haarbo et al. 1996; Anker, Chua et al. 1997) (Beer, Jakubowicz et al. 1996; Anker, Clark et al. 1997; Hak, Witteman et al. 2002). This is in agreement with the observation that high serum DHEA is associated with decreased deaths and CVD (Alexandersen, Haarbo et al. 1996).

Clinical trials suggest that testosterone replacement therapy in men may help testosterone deficient men with angina (English, Steeds et al. 2000; Malkin, Pugh et al. 2004), congestive cardiac failure (Pugh, Jones et al. 2004; Malkin, Pugh et al. 2006) and type 2 diabetes (Kapoor, Malkin et al. 2005; Kapoor, Goodwin et al. 2006). Moreover, in the human, data indicate that DHEA inhibits atherosclerosis (Eich, Nestler et al. 1993; Kurzman, Panciera et al. 1998; Hayashi, Esaki et al. 2000; Komesaroff 2008), reduces cardiovascular risk markers (Mortola and Yen 1990; Beer, Jakubowicz et al. 1996) and improves endothelial function (Kawano, Yasue et al. 2003; Williams, Dawood et al. 2004). A protective role of DHEA against atherosclerosis has also been observed in primates (Christopher-Hennings, Kurzman et al. 1995) and is particularly well known in rabbits (Gordon, Bush et al. 1988; Eich, Nestler et al. 1993).

Apart from the TOM trial, metaanalysis of a series of trials did not show adverse cardiovascular outcome (Calof, Singh et al. 2005; Haddad, Kennedy et al. 2007; Fernandez-Balsells, Murad et al. 2010). Shores et al, 2012 observed a 39% decrease in mortality risk in patients treated with testosterone and a 20% lower incidence of heart disease (Shores, Smith et al. 2012).

In the Testosterone in Older Men with Mobility Limitation (TOM) trial, the men who experienced cardiovascular events had greater increases in serum free testosterone level than those who did not (Basaria, Davda et al. 2013).

Low serum DHEA-S has been found to be positively associated with the incidence of cardiovascular events (Mitchell, Sprecher et al. 1994), the extent (Herrington, Gordon et al. 1990) as well as the incidence (Herrington, Nanjee et al. 1996), of angiographic coronary stenosis, thus suggesting a protective role of DHEA-S on CVD. Moreover, low serum testosterone has been associated with an increased risk of coronary artery disease in men (Turhan, Tulunay et al. 2007) while low DHEA levels have been reported to predispose to earlier death from CVD (Barrett-Connor, Khaw et al. 1986; Tivesten, Vandenput et al. 2009; Ohlsson, Labrie et al. 2010).

DHEA and the Brain

In addition to the traditional symptoms of menopause (Raven and Hinson 2007), the DHEA decline with age has been linked to loss of memory and cognitive function (Flood and Roberts 1988; Grimley Evans, Malouf et al. 2006).

A role of DHEA has been proposed in the etiology and treatment of neuronal damage induced by Alzheimer's disease (Simpkins, Green et al. 1997; Weill-Engerer, David et al. 2002; Yau, Rasmuson et al. 2003). The hippocampus is a brain region involved in learning, cognition and memory. This brain area shows pronounced changes during aging and in Alzheimer's disease (Beck and Handa 2004). Estrogens and DHEA which can form estrogens locally in the brain have been shown to enhance memory and learning functions (McEwen, Gould et al. 1995; Foy 2001; Vallee, Mayo et al. 2001). Studies have shown that DHEA-S can influence brain function and positively affect memory mood and energy and indirectly physical activity (Wolkowitz, Reus et al. 1999; Hunt, Gurnell et al. 2000; Huppert and Van Niekerk 2001).

the human, tests of long-term memory have been improved by DHEA administration (Barrett-Connor and Edelstein 1994). In addition, the oral administration of 25 mg DHEA per day for 12 months in aging males with partial androgen deficiency improved mood and fatigue in addition to joint pain (Genazzani, Inqlese et al. 2004).

A role of androgens has been proposed on depression, memory loss, loss of cognition and brain cell activity (Azad, Pitale et al. 2003; Hajszan, MacLusky et al. 2007; Almeida, Yeap et al. 2008). Estrogens which can also be synthesized in brain from DHEA have been shown to have a beneficial role in Alzheimer's disease, memory loss and loss of cognition (Rocca, Bower et al. 2007). Three metaanalyses have shown a 20 to 40% decreased risk of Alzheimer's disease in women who used estrogen after menopause (Yaffe 1998; Hogervorst, Williams et al. 2000; LeBlanc, Janowsky et al. 2001). Estrogen reduces beta-amyloid deposition in the brain whereas progesterone has the opposite effect (Xu, Gouras et al. 1998; Huang, Guan et al. 2004). There is now solid evidence from clinical studies that there is a critical age window for the beneficial effects of estrogens on neuroprotection (Rocca, Bower et al. 2007), cardiovascular disease (Manson, Bassuk et al. 2006) and overall mortality (Rocca, Grossardt et al. 2006).

An association between lack of estrogen and cognitive impairment or dementia is supported by laboratory data. Among them estrogen improves synapse formation on dendritic spines in the hippocampi of oophorectomized rats (McEwen and Alves 1999; Monk and Brodaty 2000). Moreover, estrogen improves cerebral blood flow and glucose metabolism and it may act as an antioxidant (Gibbs and Aggarwal 1998; McEwen and Alves 1999; Monk and Brodaty 2000). Estrogen has also been found to prevent B-Amyloid 1-42 from inducing a rise in intracellular calcium and from causing mitochondrial damage (Chen, Nilsen et al. 2006; Morrison, Brinton et al. 2006).

More and more evidence suggests a role of sex steroids, namely estradiol and testosterone in neuroprotection on the brain (Pike, Carroll et al. 2009). Data from cell culture and animal studies support testosterone as neuroprotective (Holland, Bandelow et al. 2011) and same data suggests a beneficial effect in older men on cognition (Tan and Pu 2003). In a recent preclinical study, testosterone reduced neuronal and vascular aging in hippocampal cells while (Ota, Akishita et al. 2012) decreasing cognitive decline.

Lower serum testosterone levels were found in old men with Alzheimer's disease compared to controls (Hogervorst, Bandelow et al. 2004).

Low DHEA in Longevity

Low DHEA-S has been associated to low longevity (Kushnir, Blamires et al. 2010; Labrie 2010b; Arauio and Wittert 2011; Traish, Kanq et al. 2011; Maggi, Buvat et al. 2013).

Other Potential Benefits of DHEA

The 70 to 95% reduction in the formation of DHEA and DHEA-S by the adrenals during aging results in a dramatic reduction in the formation of androgens and estrogens in peripheral target tissues, which could well be involved in the pathogenesis of age-related diseases such as insulin resistance (Coleman, Leiter et al. 1982; Schriock, Buffington et al. 1988) and obesity (Nestler, Barlascini et al. 1988; MacEwen and Kurzman 1991; Tchernof, Després et al. 1995). DHEA has been found to exert antioncogenic activity in a series of animal models (Schwartz, Pashko et al. 1986; Gordon, Shantz et al. 1987; Li Yan et al. 1993). DHEA has also been shown to have immuno modulatory effects in vitro (Suzuki, Suzuki et al. 1991) and in vivo in fungal and viral diseases (Rasmussen, Arrowood et al. 1992), including HIV (Henderson, Yang et al. 1992). On the other hand, a stimulatory effect of DHEA on the immune system has been described in postmenopausal women (Casson, Andersen et al. 1993).

DHEA and Lipids

Following administration of various doses of DHEA for variable periods of time, small but significant decreases in total and high-density lipoprotein (HDL) cholesterol have been reported (Nestler, Barlascini et al. 1988; Mortola and Yen 1990; Arlt, Callies et al. 1999; Barnhart, Freeman et al. 1999; Petri, Lahita et al. 2002; Petri, Mease et al. 2004) while, in other studies, low-density lipoprotein (LDL) cholesterol was also decreased in addition to total and HDL cholesterol (Gebre-Medhin, Husebye et al. 2000; Dhatariya, Bigelow et al. 2005). A small decrease in serum HDL cholesterol has been reported in previous studies with DHEA administered at the daily dose of 50 mg (Arlt, Callies et al. 1999; Barnhart, Freeman et al. 1999; Hunt, Gurnell et al. 2000), 4-6 g 10% DHEA cream (Labrie, Bélanger et al. 1997a), 1600 mg (Mortola and Yen 1990) or 25 mg (Casson, Santoro et al. 1998) while, in other studies, no significant effect was seen at 50 mg/day (Morales, Nolan et al. 1994; Barnhart, Freeman et al. 1999; Villareal, Holloszy et al. 2000) or 25 mg/day (Kawano, Yasue et al. 2003; Lovas, Gebre-Medhin et al. 2003).

DHEA, contrary to estrogens, does not increase triglycerides (Diamond, Cusan et al. 1996). In fact, a decrease in triglycerides is often seen with DHEA (Lasco, Frisina et al. 2001; Chang, Lan et al. 2002; Dhatariya, Bigelow et al. 2005). Increased HDL and decreased LDL cholesterol have also been reported (Lasco, Frisina et al. 2001) while a decrease in total cholesterol only has been reported (Libe, Barbetta et al. 2004; Williams, Dawood et al. 2004). DHEA administration in postmenopausal women has also been reported to decrease serum Apolipoprotein A and increase HDL cholesterol (Casson, Santoro et al. 1998; Morales, Haubrich et al. 1998). DHEA has been found to decrease serum Lp(A) (Barnhart, Freeman et al. 1999), an effect which should be beneficial for CVD (Lobo 1991).

The decrease in triglycerides and HDL cholesterol levels under the influence of androgens has been reported to result from increased hepatic lipase activity which results in increased clearance of HDL (Haffner, Kushwaha et al. 1983; Hazzard, Haffner et al. 1984; Kantor, Bianchini et al. 1985). The increased reverse cholesterol transport (removal of cholesterol from peripheral tissues via increased HDL clearance) seems responsible for the decreased HDL and triglyceride levels rather than decreased HDL production (Wu and von Eckardstein 2003). The relatively small (when present) inhibitory effect of DHEA on total cholesterol, HDL cholesterol and sometimes LDL cholesterol could also involve the effects of DHEA-derived androgens on hepatic lipase activity, thus impairing hepatic cholesterol formation (Tan, Shiu et al. 1998).

Figure 10:
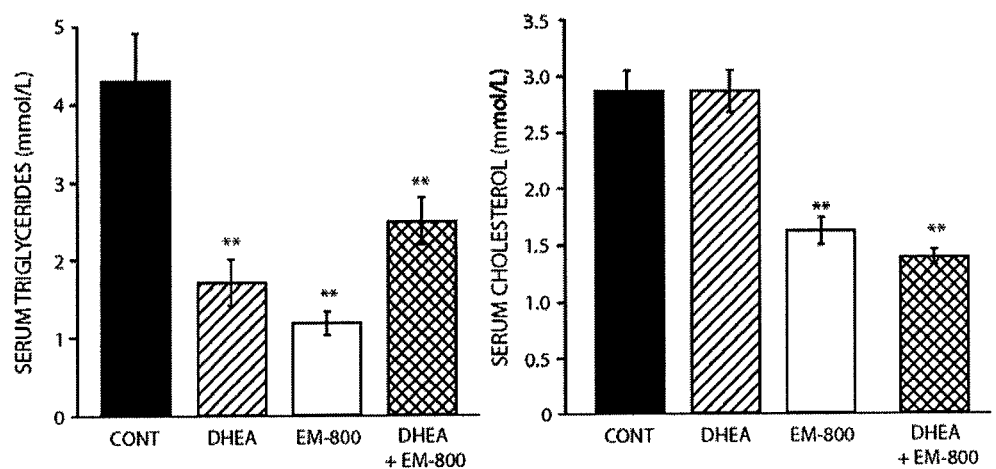
FIG. 10 shows the effect of treatment with DHEA (10 mg, percutaneously, once daily) or EM-800 (prodrug of acolbifene, free salt) (75 µg, orally, once daily) alone or in combination for 9 months on serum triglycerides (A) and cholesterol (B) levels in the rat. Data are expressed as the means±SEM. **: $p<0.01$ experimental versus respective control.
Figure 11:
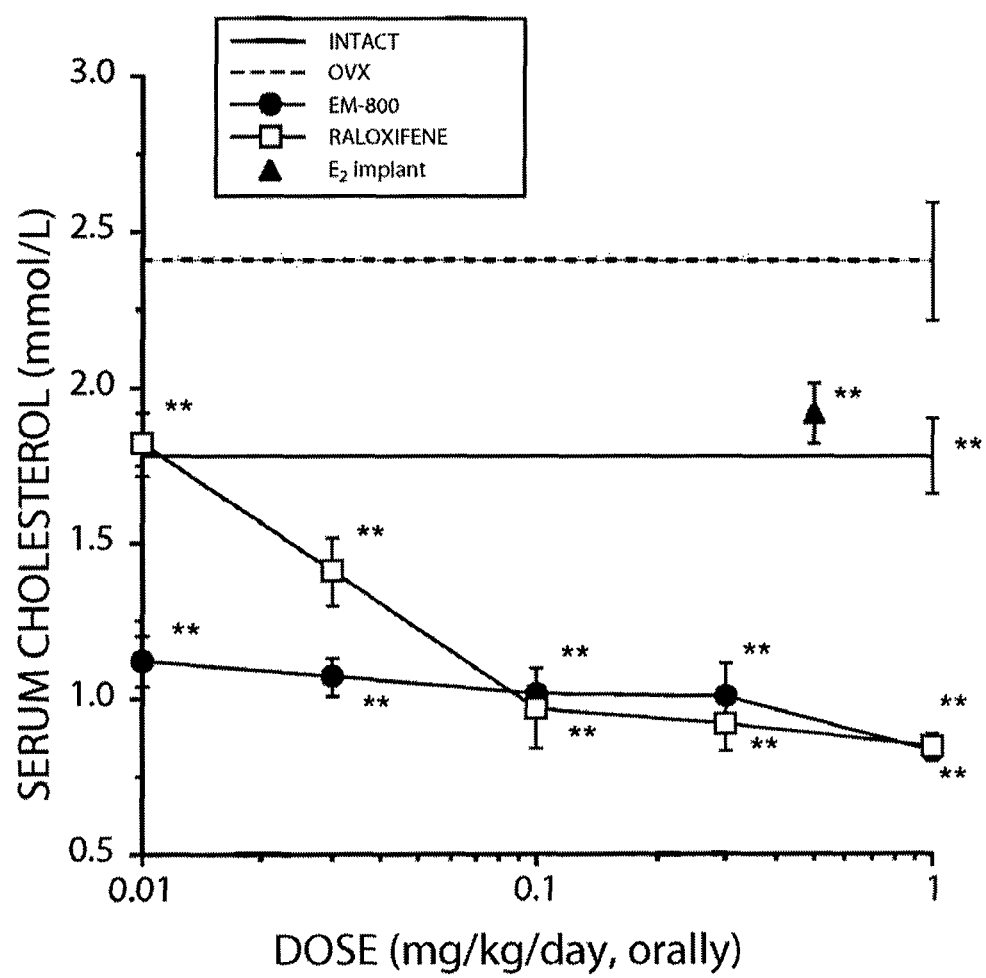
FIG. 11 shows the effect of 37-week treatment with increasing doses (0.01, 0.03, 0.1, 0.3, and 1 mg/kg) of EM-800 (prodrug of acolbifene, free salt) or raloxifene administered on total serum cholesterol levels in the ovariectomized rat. Comparison is made with intact rats and ovariectomized animals bearing an implant of 17β-estradiol ($E_2$); **$p<0.01$, experimental versus OVX control rats.

The consensus is that DHEA has only small and no clinically significant effects on lipids (Arlt, Justl et al. 1998; Morales, Haubrich et al. 1998; Gebre-Medhin, Husebye et al. 2000; Lasco, Frisina et al. 2001; Poretsky, Brillon et al. 2006; Gurnell, Hunt et al. 2008; Lovas and Husebye 2008). Our preclinical studies, however, shown inhibitory effect on serum triglycerides and no effect on cholesterol (FIG. 10) while EM-800 (a prodrug of acolbifene, free salt) decreases both serum triglycerides (FIG. 10) and cholesterol (FIGS. 10 and 11).

Benefits of DHEA: Combination of Estrogen-Like and Androgenic Effects

Figure 13:
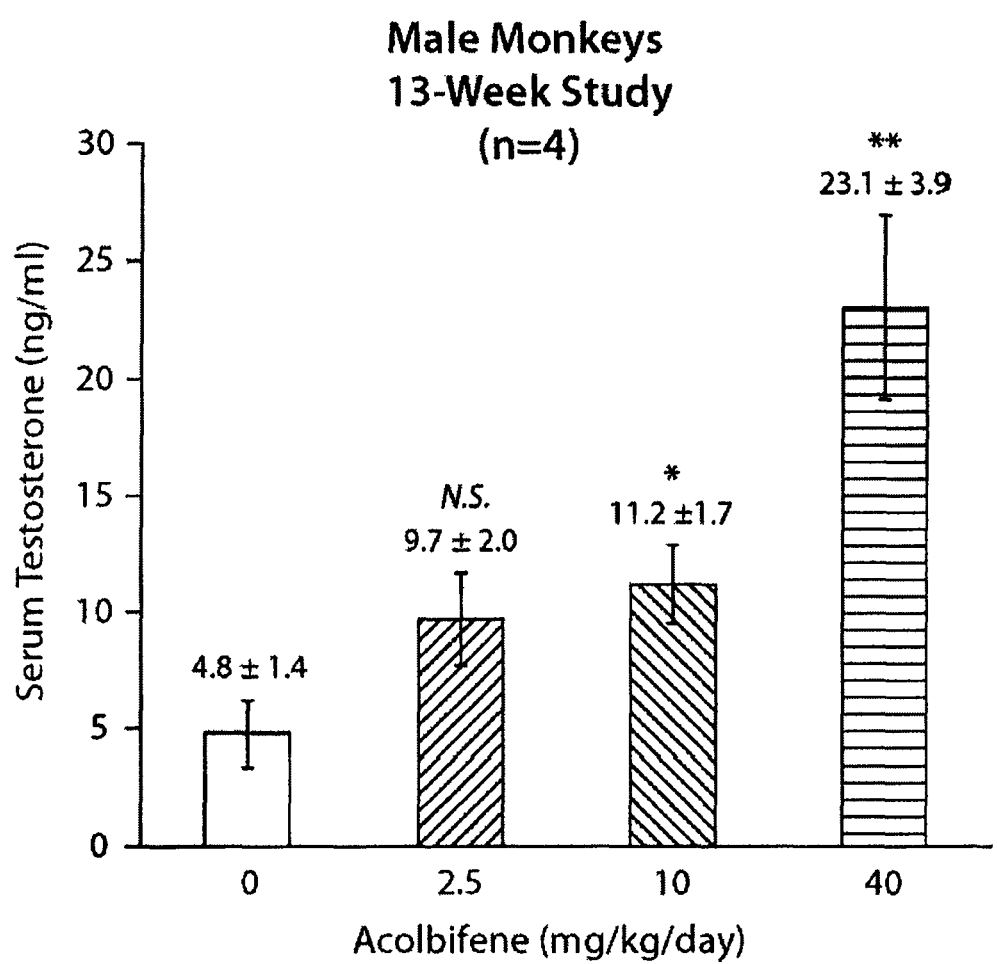
FIG. 13: Male cynomolgus monkeys were dosed orally with 2.5, 10 or 40 mg acolbifene/day for 13 weeks. Control monkeys received vehicle alone (0.4% methylcellulose). End of study serum testosterone concentrations were determined using a validated gas chromatography mass spectrometric assay. Results are expressed as the mean±SEM of 4 monkeys per group. P values (versus control) were calculated using a two-sided t test assuming equality of variances.
Figure 14:
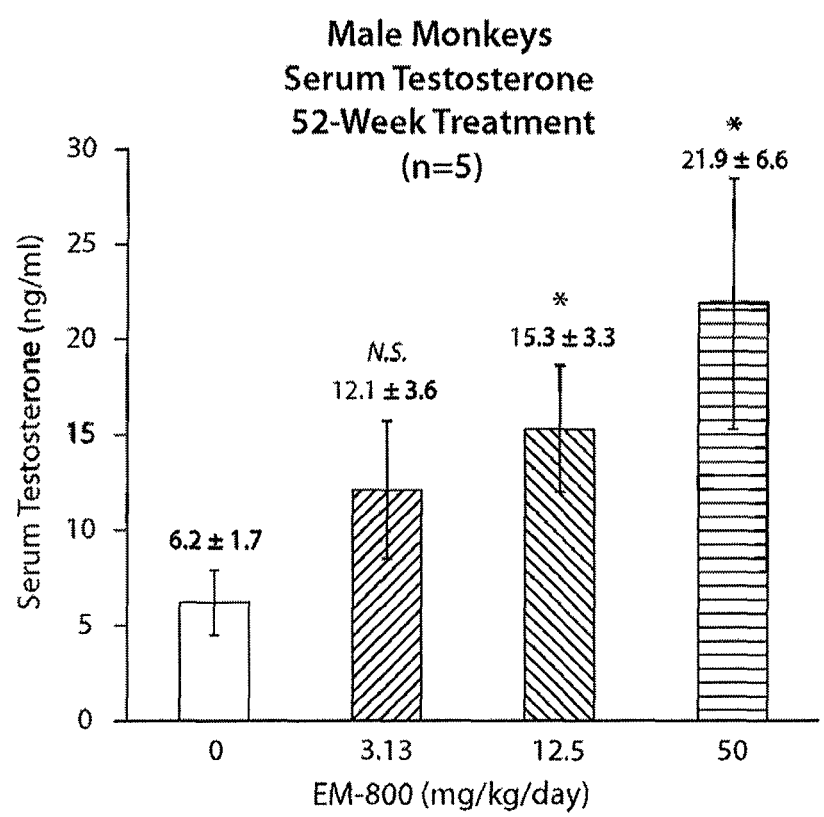
FIG. 14: Male cynomolgus monkeys were dosed orally with 3.13, 12.5 or 50 mg EM-800 (prodrug of acolbifene, free salt)/day for 52 weeks. Control monkeys received vehicle alone (0.4% methylcellulose). End of study serum testosterone concentrations were determined using a validated gas chromatography mass spectrometric assay. Results are expressed as the mean±SEM of 5 (EM-800 study) monkeys per group. P values (versus control) were calculated using a two-sided t test assuming equality of variances.

The present invention is based upon the recent progress achieved in our understanding of sex steroid physiology in men and women and the recognition that women, at menopause, are not only deprived from estrogen due to the arrest of estrogen secretion by the ovaries, but have already been submitted for a few years to a decreasing exposure to androgens. In fact, normal women produce an amount of androgens equivalent to approximately 50% of the androgens secreted in men (Labrie, Bélanger et al. 1997a). The pool of androgens in men and women decreases progressively from the age of 30 years in parallel with the decrease in the serum concentration of DHEA and DHEA-S (Labrie, Bélanger et al. 1997b). The addition of a SERM like acolbifene is to increase the serum levels of testosterone (FIG. 12) as well as the positive effect on bone loss protection as well as on other benefits of SERM administration. In FIG. 12, a schematic representation of the effects of DHEA and acolbifene is presented by blocking the negative feedback effect of estrogens on GnRH/LH secretion, as further illustrated in FIGS. 13 and 14 obtained in the cynomolgus male monkey, increased serum testosterone levels are observed.

That acolbifene increased LH secretion in the human is indicated by the increase in serum $E_2$ levels from 222 to 2030 μg/mL at 6 months of daily oral administration of 20 mg acolbifene in a premenopausal women with advanced breast cancer.

Beneficial Effects of Acolbifene

Figure 15:
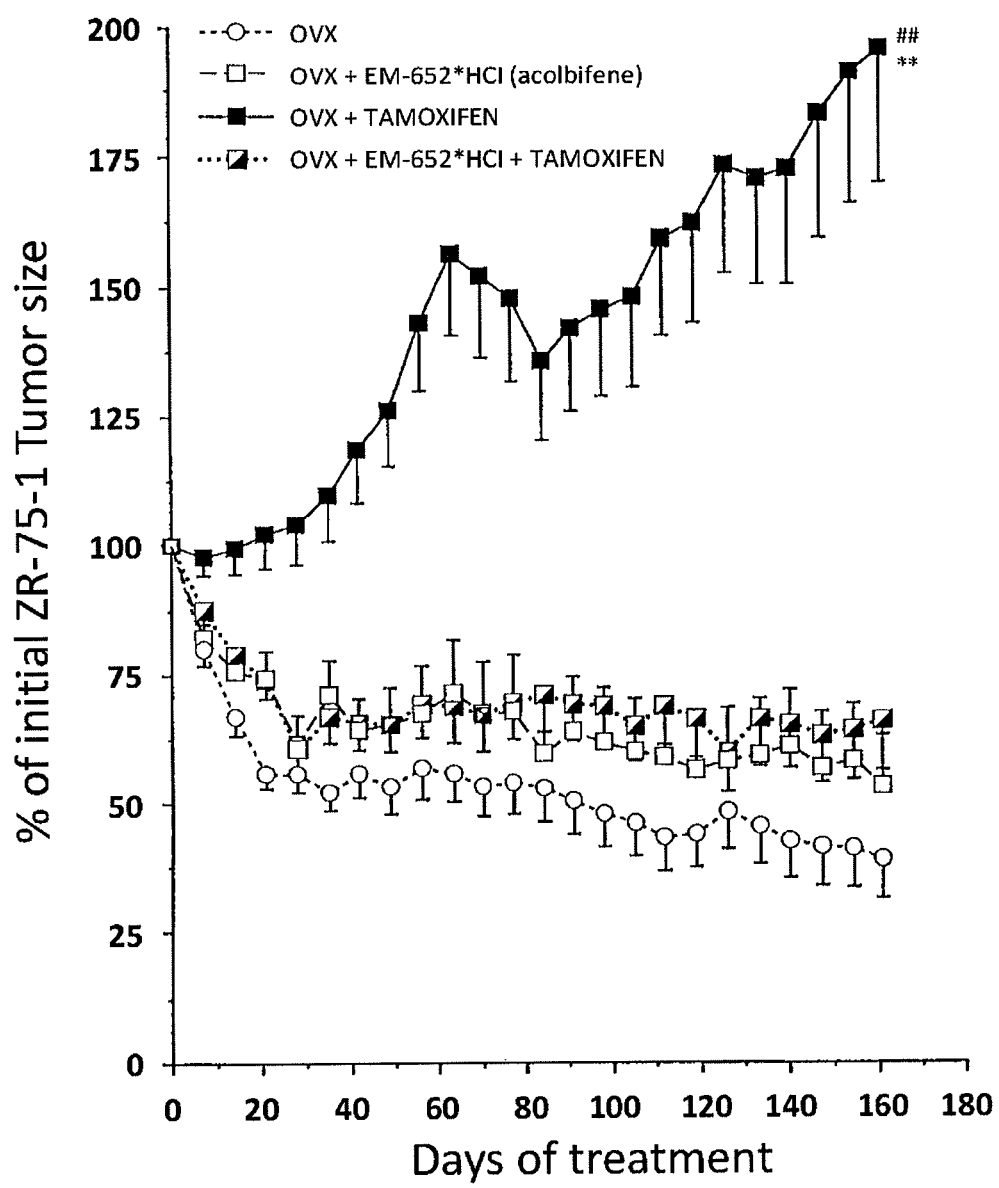
FIG. 15 shows the effects of antiestrogens on ZR-75-1 tumor growth. Effect of treatment with the antiestrogens tamoxifen, EM-652.HCl (acolbifene) and the combination of tamoxifen and EM-652.HCl for 161 days, on the growth of human ZR-75-1 breast tumors in ovariectomized nude mice. Tumor size is expressed as the percentage of initial tumor area (Day 1=100%). Data is expressed as means±SEM (n=18-30 tumors/group); ##$p<0.01$ vs EM-652.HCl (acolbifene); **$p<0.01$ vs OVX. Antiestrogens were administered orally once daily at the dose of 200 µg/mouse in absence of estrogen stimulation.

It can be seen in FIG. 15 that the approximately 100% stimulatory effect of tamoxifen on tumor growth was completely blocked by simultaneous treatment with EM-652.HCl (acolbifene) EM-652.HCl in accordance with its pure antiestrogenic activity did not exert any stimulatory effect on the growth of the human breast cancer ZR-75-1 xenografts in nude mice.

We have also noted a correlation between the beneficial effect of SERMs have on serum cholesterol and beneficial estrogenic or estrogen-like effects on bone. SERMs have also a beneficial effect on hypertension, insulin resistance, diabetes, and obesity (especially abdominal obesity). Without intending to be bound by theory, it is believed that SERMs, many of which preferably have two aromatic rings linked by one to two carbon atoms, are expected to interact with the estrogen receptor by virtue of the foregoing portion of the molecule that is best recognized by the receptor. Preferred SERMs have side chains which may selectively cause antagonistic properties in breast and usually uterine tissues without having significant antagonistic properties in other tissues. Thus, the SERMs may desirably functions as antiestrogens in the breast while surprisingly and desirably functioning as estrogens (or providing estrogen-like activity) in bone and in the blood (where concentrations of lipid and cholesterol are favorably affected). The favorable effect on cholesterol and lipids translates to a favorable effect against atherosclerosis which is known to be adversely, affected by improper levels of cholesterol and lipids (FIGS. 10 and 11).

Cardiovascular symptoms, Alzheimer's disease, loss of cognitive functions and insomnia involve certainly estrogen receptors situated in the nervous central system. Probably, decreased levels of estrogens (or androgens) in the brain, can explain at least in part, these conditions. Exogenous estrogens and particularly those (i.e. estradiol) formed by the administration of sex steroid precursors can pass through the brain barrier and bind to the estrogen receptor to restore the normal estrogenic action. On the other hand, SERMs of the invention, and more particularly those of acolbifene family, cannot pass through the brain barrier as shown in example 8. Thus, they cannot antagonise the positive effect of estrogens in brain but they antagonise the negative effects of estrogens in the breast, rending this combination (SERM+ sex steroid precursor) particularly attractive for the treatment or reduction of the risk of acquiring the above-mentioned conditions.

As mentioned earlier, a role for androgens has also been suggested for all these symptoms. In fact, DHEA can provide both estrogens and androgens in the brain according to physiological needs.

Overall Additive Benefits of Combining a Sex Steroid Precursor and a SERM or an Antiestrogen No adverse effect of EM-652 (acolbifene) has been seen on any parameter while it should exert marked beneficial effects for the prevention and treatment of gynecomastia, breast cancer and osteoporosis.

Preferred SERMs or antiestrogens discussed herein relate: (1) to all diseases stated to be susceptible to the invention; (2) to both therapeutic and prophylactic applications; and (3) to preferred pharmaceutical compositions and kits.

A patient in need of treatment or of reducing the risk of onset of a given disease is one who has either been diagnosed with such disease or one who is susceptible of acquiring such disease.

Except where otherwise stated, the preferred dosage of the active compounds (concentrations and modes of administration) of the invention is identical for both therapeutic and prophylactic purposes. The dosage for each active component discussed herein is the same regardless of the disease being treated (or of the disease whose likelihood of onset is being reduced).

Except when otherwise noted or where apparent from context, dosages herein refer to weight of active compounds unaffected by pharmaceutical excipients, diluents, carriers or other ingredients, although such additional ingredients are desirably included, as shown in the examples herein. Any dosage form (capsule, pill, tablet, injection or the like) commonly used in the pharmaceutical industry is appropriate for use herein, and the terms "excipient", "diluent", or "carrier" include such nonactive ingredients as are typically included, together with active ingredients in such dosage forms in the industry. For example, typical capsules, pills, enteric coatings, solid or liquid diluents or excipients, flavorants, preservatives, or the like may be included.

All of the active ingredients used in any of the therapies discussed herein may be formulated in pharmaceutical compositions which also include one or more of the other active ingredients. Alternatively, they may each be administered separately but sufficiently simultaneous in time so that a patient eventually has elevated blood levels or otherwise enjoys the benefits of each of the active ingredients (or strategies) simultaneously. In some preferred embodiments of the invention, for example, one or more active ingredients are to be formulated in a single pharmaceutical composition. In other embodiments of the invention, a kit is provided which includes at least two separate containers wherein the contents of at least one container differs, in whole or in part, from the contents of at least one other container with respect to active ingredients contained therein.

Combination therapies discussed herein also include use of one active ingredient (of the combination) in the manufacture of a medicament for the treatment (or risk reduction) of the disease in question where the treatment or prevention further includes another active ingredient of the combination in accordance with the invention. For example in one embodiment, the invention provides the use of a SERM in the preparation of a medicament for use, in combination with a sex steroid precursor in vivo, in the treatment of any of the diseases for which the present combination therapy is believed effective.

The limitations of bone mineral density (BMD) measurements are well known. As an example, BMD measurements showed no change in rats treated with the steroidal antiestrogen ICI 182780 (Wakeling 1993) while inhibitory changes were seen by histomorphometry (Gallagher, Chambers et al. 1993). Similar differences were reported with tamoxifen (Jordan, Phelps et al. 1987; Sibonga, Evans et al. 1996).

It should be indicated that reduced bone mineral density is not the only abnormality associated with reduced bone strength. It is thus important to analyze the changes in biochemical parameters of bone metabolism induced by various compounds and treatments in order to gain a better knowledge of their action (Table 2).

It is particularly important to indicate that the combination of DHEA and acolbifene exerted unexpected beneficial effects on important biochemical parameters of bone metabolism. In fact, DHEA alone did not affect the urinary hydroxyproline/creatinine ratio, a marker of bone resorption. Moreover, no effect of DHEA could be detected on daily urinary calcium or phosphorus excretion (Luo, Sourla et al. 1997). EM-800 (prodrug of acolbifene free salt) decreased the urinary hydroxyproline/creatinine ratio by 48% while, similarly to DHEA, no effect of EM 800 (prodrug of acolbifene, free salt) was seen on urinary calcium or phosphorus excretion. EM-800, moreover, had no effect on serum alkaline phosphatase activity, a marker of bone formation while DHEA increased the value of the parameter by about 75% (Luo, Sourla et al. 1997).

One of the unexpected effects of the combination of DHEA and EM-800 relates to the urinary hydroxyproline/creatinine ratio, a marker of bone resorption, which was reduced by 69% when both DHEA and EM-800 were combined, this value being statistically different (p<0.01) from the 48% inhibition achieved by EM-800 alone while DHEA alone did not show any effect. Thus, the addition of DHEA to EM-800 increases by 50% the inhibitory effect of EM-800 on bone reabsorption. Most importantly, another unexpected effect of the addition of DHEA to EM-800 (prodrug of acolbifene, free salt) was the approximately 84% decrease in urinary calcium (from 23.17±1.55 to 3.71±0.75 µmol/24 h/100 g (p<0.01) and the 55% decrease in urinary phosphorus (from 132.7±6.08 to 59.06±4.76 µmol/24 h/100 g (p<0.01) respectively (Luo, Sourla et al. 1997).

Importantly, the combination of acolbifene and DHEA in ovariectomized rats treated for 12 months had beneficial effects on bone morphometry. Trabecular bone volume is particularly important for bone strength and to prevent bone fractures (FIG. 7). Thus, in the above-mentioned study, trabecular bone volume of the tibia increased from 4.1±0.7% in ovariectomized rats to 11.9±0.6% (p<0.01) with DHEA alone while the addition of EM-800 to DHEA further increased trabecular bone volume to 14.7±1.4%, a value similar to that found in intact controls (FIG. 7).

From a value of 0.57±0.08 per mm in ovariectomized rats, treatment with DHEA resulted in a 137% increase in trabecular bone number compared to ovariectomized controls (FIG. 8). The stimulatory effect of DHEA thus reached 1.27±0.1 per mm while simultaneous treatment with EM-800 and DHEA resulted in an additional 28% increase in trabecular bone number (p<0.01) compared to that achieved by DHEA alone (FIG. 8). Similarly, the addition of EM-800 to DHEA treatment, resulted in an additional 15% (p<0.05) decrease in trabecular bone separation, compared to that achieved with DHEA alone, thus leading to values not different from those seen in intact controls.

As complement to the numerical data presented in FIGS. 7 and 8, FIG. 9 illustrates the increase in trabecular bone volume in the proximal tibia metaphysis induced by DHEA in ovariectomized treated animals (C) compared to ovariectomized controls (B), as well as the partial inhibition of the stimulatory effect of DHEA after the addition of Flutamide to DHEA treatment (D). On the other hand, administration of DHEA in combination with EM-800 resulted in a complete prevention of the ovariectomy-induced osteopenia (E), the trabecular bone volume being comparable to that seen in intact controls (A).

TABLE 3

Effect of 12-month treatment with dehydroepiandrosterone (DHEA) administered alone or in combination with Flutamide (FLU) or EM-800 on bone markers and serum lipids.

| Group | Alkaline phosphatase IU/L | OH-proline/creatinine µmol/mmol | Cholesterol mmol/L | Triglycerides mmol/L |
|---|---|---|---|---|
| Intact Control | 30 ± 3** | 15.4 ± 1.3 | 2.28 ± 0.12 | 1.4 ± 0.2 |
| OVX Control | 51 ± 4 | 11.7± 1.2 | 2.29 ± 0.16 | 1.1 ± 0.1 |
| OVX + DHEA | 201 ± 25** | 7.3 ± 1.0* | 1.78 ± 0.16* | 0.8 ± 0.1 |
| OVX + DHEA + FLU | 103 ± 10** | 14.5 ± 1.2 | 2.27 ± 0.15 | 0.8 ± 0.1 |
| OVX + DHEA + EM-800 | 202 ± 17** | 6.4 ± 1.0** | 0.63 ± 0.09** | 1.0 ± 0.2 |

*p < 0.05;
**p < 0.01 versus OVX Control

The importance of the androgenic component of the stimulatory effect of DHEA on bone histomorphometry is also supported by the effect of DHEA on markers of bone formation and resorption. The concentration of serum alkaline phosphatase, a marker of bone formation (Lauffenburger, Olah et al. 1977; Meunier, Salson et al. 1987) was increased from 51±4 IU/L in OVX controls to 201±25 IU/L in DHEA-treated animals, suggesting a stimulatory effect of DHEA on bone formation (Table 3). FLU reversed by 65% the stimulatory effect of DHEA on this parameter while EM-800 had no significant effect. On the other hand, since hydroxyproline released during collagen degradation is not reutilized in collagen synthesis, it is a useful marker of collagen metabolism or osteoclastic bone resorption. In the present study, the urinary hydroxyproline/creatinine ratio decreased from 11.7±1.2 µmol/mmol in OVX controls to 7.3±1.0 µmol/mmol (p<0.05) in DHEA-treated rats (Table 3). The administration of FLU completely prevented the inhibitory effect of DHEA on this parameter while EM-800 had no statistically significant influence on the effect of DHEA.

Moreover, serum cholesterol was reduced by 22% from 2.29±0.16 to 1.78±0.16 mmol/l (p<0.05) by DHEA treatment, an effect neutralized by concomitant treatment with the pure antiandrogen FLU. The addition of the pure antiestrogen EM-800, on the other hand, decreased total serum cholesterol further to 0.63±0.09 mmol/l (p<0.01), thus reaching a 65% inhibitory effect. No statistically significant change was observed in serum triglyceride levels with any of the treatments used (Table 3).

It is also of interest to note that the potent inhibitory effect of EM-800 (prodrug of acolbifene, free salt) on serum cholesterol is not prevented by simultaneous treatment with DHEA (Luo, Sourla et al. 1997).

Cancellous bone strength and subsequent resistance to fracture do not only depend upon the total amount of cancellous bone but also on the trabecular microstructure, as

TABLE 2

| GROUP | URINE | | | SERUM |
| | CALCIUM (µmol/24 h/100 g) | PHOSPHORUS (µmol/24 h/100 g) | HP/Cr (µmol/mmol) | tALP (IU/L) |
|---|---|---|---|---|
| CONTROL | 23.17 ± 1.55 | 132.72 ± 6.08 | 13.04 ± 2.19 | 114.25 ± 14.04 |
| DHEA (10 mg) | 25.87 ± 3.54 | 151.41 ± 14.57 | 14.02 ± 1.59 | 198.38 ± 30.76* |
| EM-800 (75 µg) | 17.44 ± 4.5 | 102.03 ± 25.13 | 6.81 ± 0.84** | 114.11 ± 11.26 |
| DHEA + EM-800 | 3.71 ± 0.75 | 59.06 ± 4.76 | 4.06 ± 0.28 | 204.38 ± 14.20 | determined by the number, size, and distribution of the trabeculae. The loss of ovarian function in postmenopausal women is accompanied by a significant decrease in total trabecular bone volume (Melsen, Melsen et al. 1978; Kleerekoper, Villanueva et al. 1985), mainly related to a decrease in the number and, to a lesser degree, in the width of trabeculae (Weinstein and Hutson 1987).

In order to facilitate the combination therapy aspect of the invention, for any indication discussed herein, the invention contemplates pharmaceutical compositions which include the SERM and the sex steroid precursor in a single composition for simultaneous administration. The composition may be suitable for administration in any traditional manner including but not limited to oral administration, subcutaneous injection, intramuscular injection or percutaneous administration. In other embodiments, a kit is provided wherein the kit includes one or more SERM and sex steroid precursor in separate or in one container. The kit may include appropriate materials for oral administration, e.g. tablets, capsules, syrups and the like and for transdermal administration, e.g., ointments, lotions, gels, creams, sustained release patches and the like.

Applicants believe that administration of SERMs or antiestrogens and sex steroid precursors has utility in the treatment and/or reduction of the incidence of any of the symptoms mentioned above. The active ingredients of the invention (whether SERM, antiestrogen or precursor or otherwise) may be formulated and administered in a variety of ways. When administered together in accordance with the invention, the active ingredients may be administered simultaneously or separately.

Active ingredient for transdermal or transmucosal is preferably from 0.01% to 5%, DHEA or 5-diol.

Figure 16:
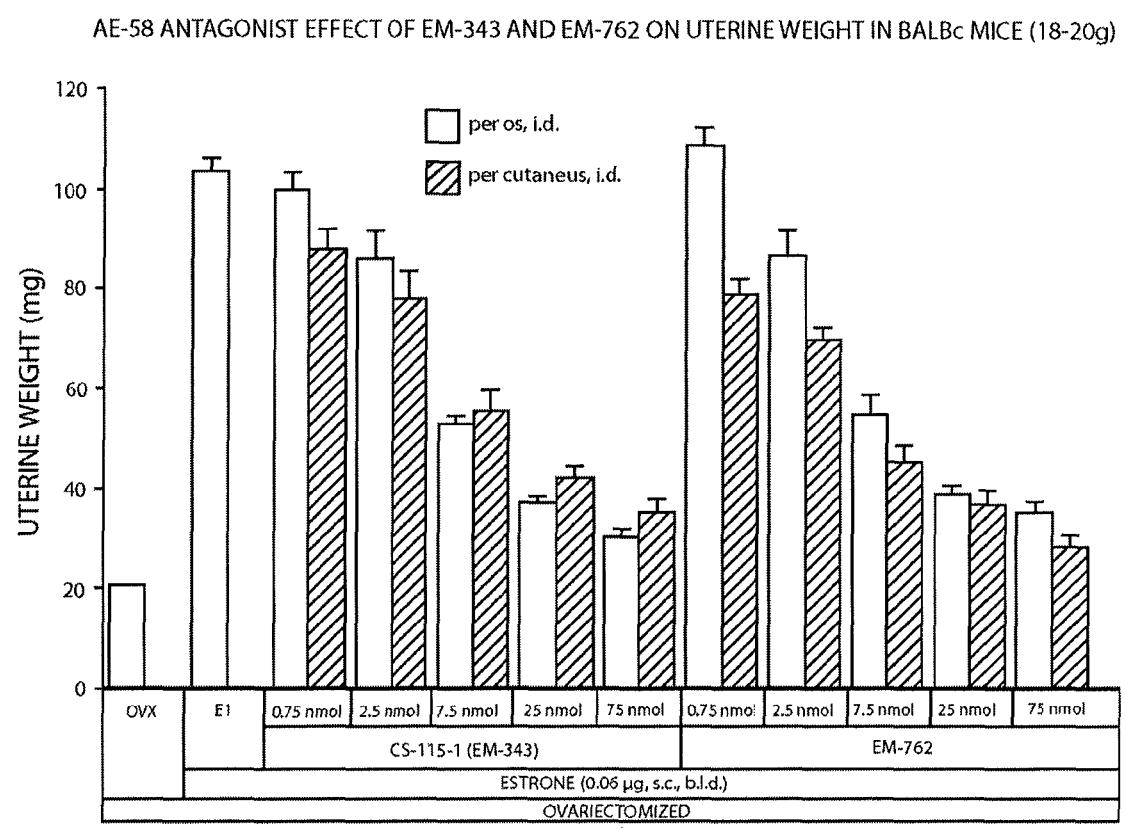
FIG. 16 Effect on uterine weight of increasing daily doses of the antiestrogens CS-115-1 (EM-343) and EM-762 administered orally or percutaneously by application on the skin for 9 days to ovariectomized mice simultaneously treated by twice daily subcutaneous injection of estrone.

That the SERM can be administered percutaneously is indicated by the comparable efficacy of acolbifene analogs to antagonize the stimulatory effect of estradiol on uterine weight whether acolbifene analogs are administered orally or percutaneously in mice (FIG. 16).

When formulated as an ointment, lotion, gel, cream, or suppository or the like, the active compound is admixed with a suitable carrier which is compatible with human skin or mucosa and which enhances transdermal or transmucosal penetration of the compound through the skin or mucosa. Suitable carriers are known in the art and include but are not limited to Klucel HF and Glaxal base. Some are commercially available, e.g., Glaxal base available from Glaxal Canada Limited Company. Other suitable vehicles can be found in Koller and Buri, S.T.P. Pharma (Koller and Buri 1987). The carrier is preferably one in which the active ingredient(s) is (are) soluble at ambient temperature at the concentration of active ingredient that is used. The carrier should have sufficient viscosity to maintain the inhibitor on a localized area of skin or mucosa to which the composition has been applied, without running or evaporating for a time period sufficient to permit substantial penetration of the precursor through the localized area of skin or mucosa and into the bloodstream where it will cause a desirable clinical effect. The carrier is typically a mixture of several components, e.g. pharmaceutically acceptable solvents and a thickening agent. A mixture of organic and inorganic solvents can aid hydrophylic and lipophilic solubility, e.g. water and an alcohol such as ethanol.

When formulated as an ovule or a rectal suppository or the like, the active compound is admixed with a suitable carrier which is compatible with human rectal mucosa. Preferred carriers are hard fats (mixture of glycerides of saturated fatty acids), particularly Witepsol, and specially Witepsol H-15 base (available from Medisca, Montreal, Canada). Any other lipophilic base such as Fattibase, Wecobee, cocoa butter, *theobroma* oil or other combinations of Witepsol bases could used.

Preferred sex steroid precursors are dehydroepiandrosterone (DHEA) (available, for example, from Proquina, Orizaba, Veracruz, Mexico).

The carrier may also include various additives commonly used in ointments, lotions and suppositories and well known in the cosmetic and medical arts. For example, fragrances, antioxidants, perfumes, gelling agents, thickening agents such as carboxymethylcellulose, surfactants, stabilizers, emollients, coloring agents and other similar agents may be present.

Treatment in accordance with the invention is suitable for indefinite continuation. The SERM, or antiestrogenic compound and the sex steroid precursor can also be administered, by the oral route, and may be formulated with conventional pharmaceutical excipients, e.g. spray dried lactose, microcrystalline cellulose, and magnesium stearate into tablets or capsules for oral administration.

The active substances can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol. Of course, taste-improving substances can be added in the case of oral administration forms.

As further forms, one can use plug capsules, e.g. of hard gelatin, as well as closed soft-gelatin capsules comprising a softener or plasticizer, e.g. glycerin. The plug capsules contain the active substance preferably in the form of granulate, e.g. in mixture with fillers, such as lactose, saccharose, mannitol, starches, such as potato starch or amylopectin, cellulose derivatives or highly dispersed silicic acids. In solf-gelatin capsules, the active substance is preferably dissolved or suspended in suitable liquids, such as vegetable oils or liquid polyethylene glycols.

The lotion, ointment, gel or cream should be thoroughly rubbed into the skin so that no excess is plainly visible, and the skin should not be washed in that region until most of the transdermal penetration has occurred preferably at least 4 hours and, more preferably, at least 6 hours.

A transdermal patch may be used to deliver precursor in accordance with known techniques. It is typically applied for a much longer period, e.g., 1 to 4 days, but typically contacts active ingredient to a smaller surface area, allowing a slow and constant delivery of active ingredient.

A number of transdermal drug delivery systems that have been developed, and are in use, are suitable for delivering the active ingredient of the present invention. The rate of release is typically controlled by a matrix diffusion, or by passage of the active ingredient through a controlling membrane.

Mechanical aspects of transdermal devices are well known in the rat, and are explained, for example, in U.S. Pat. Nos. 5,162,037, 5,154,922, 5,135,480, 4,666,441, 4,624,665, 3,742,951, 3,797,444, 4,568,343, 5,064,654, 5,071,644, 5,071,657, the disclosures of which are incorporated herein by reference. Additional background is provided by European Patent 0279982 and British Patent Application 2185187.

The device may be any of the general types known in the art including adhesive matrix and reservoir-type transdermal delivery devices. The device may include drug-containing matrixes incorporating fibers which absorb the active ingredient and/or carrier. In a reservoir-type device, the reservoir may be defined by a polymer membrane impermeable to the carrier and to the active ingredient.

In a transdermal device, the device itself maintains active ingredient in contact with the desired localized skin surface. In such a device, the viscosity of the carrier for active ingredient is of less concern than with a cream or gel. A solvent system for a transdermal device may include, for example, oleic acid, linear alcohol lactate and dipropylene glycol, or other solvent systems known in the art. The active ingredient may be dissolved or suspended in the carrier.

For attachment to the skin, a transdermal patch may be mounted on a surgical adhesive tape having a hole punched in the middle. The adhesive is preferably covered by a release liner to protect it prior to use. Typical material suitable for release includes polyethylene and polyethylene-coated paper, and preferably silicone-coated for ease of removal. For applying the device, the release liner is simply peeled away and the adhesive attached to the patient's skin. In U.S. Pat. No. 5,135,480, the disclosure of which is incorporated by reference, describe an alternative device having a non-adhesive means for securing the device to the skin.

It is necessary only that SERM, antiestrogen and sex steroid precursor be administered in a manner and at a dosage sufficient to allow blood serum concentration of each to obtain desired levels. In accordance with the combination therapy of the invention, concentration of the SERM is maintained within desired parameters at the same time that sex steroid precursor concentration is maintained within desired parameters One preferred sex steroid precursor is DHEA, although DHEA-S and analogs discussed below are also especially effective for the reasons stated below.

A selective estrogen receptor modulator of the invention has a molecular formula with the following features: a) two aromatic rings spaced by 1 to 2 intervening carbon atoms, both aromatic rings being either unsubstituted or substituted by a hydroxyl group or a group converted in vivo to hydroxyl; and b) a side chain possessing an aromatic ring and a tertiary amine function or salt thereof.

One preferred SERM of the invention is acolbifene:

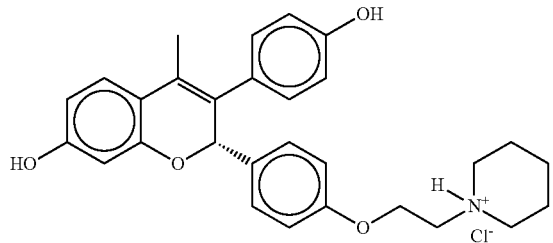

Acolbifene (also called EM-652.HCl; EM-1538) is the hydrochloride salt of the potent antiestrogen EM-652. It is disclosed in U.S. Pat. No. 6,710,059 B1. Another preferred SERM is lasofoxifene (Oporia; CP-336,156; (−)-cis-(5R, 6S)-6-phenyl-5-[4-(2-pyrrolidin-1-ylethoxy)phenyl]-5,6,7, 8-tetrahydronaphthalen-2-ol, D-(−)-tartrate salt) (available from Pfizer Inc., USA).

Another preferred SERM is bazedoxifene (TSE 424; WAY-TSE 424; WAY 140424; 1-[[4-[2-(hexahydro-1H-azepin-1-yl)ethoxy]phenyl]methyl]-2-(4-hydroxy phenyl)-3-methyl-1H-indol-5-ol, acetate) developed by Wyeth Ayers (USA) and disclosed in JP10036347 (American home products corporation) and approved in USA for the prevention of postmenopausal osteoporosis and non-steroidal estrogen derivatives described in WO 97/32837. Other preferred SERMs of the invention include tamoxifen ((Z)-2-[4-(1,2-diphenyl-1-butenyl) phenoxy]-N,N-dimethylethanamine) (available from Zeneca, UK), toremifene ((Z)-2-[4-(4-Chloro-1,2-diphenyl-1-butenyl)phenoxy]-N,N-dimethyl-ethanamine) available from Orion, Finland, under the trademark Fareston or Schering-Plough), droloxifene ((E)-3-[1-[4-[2-(Dimethylamino) ethoxy]phenyl]-2-phenyl-1-butenyl] phenol) and, from Eli Lilly and Co., USA: raloxifene ([2-(4-hydroxyphenyl)-6-hydroxybenzo[b]thien-3-yl][4-[2-(1-piperidinyl) ethoxy]phenyl]-methanone hydrochloride), LY 335124, LY 326315, LY 335563 (6-hydroxy-3-[4-[2-(1-piperidinyl)ethoxy]phenoxyl]-2-(4-hydroxyphenyl)benzo [b]thiopene hydrochloride) and arzoxifene (LY 353381, 6-hydroxy-3-[4-[2-(1-piperidinyl)ethoxy]phenoxyl]-2-(4-methoxyphenyl)benzo[b]thiophene hydrochloride). Other preferred SERMs are idoxifene ((E)-1-[2-[4-[1-(4-Iodophenyl)-2-phenyl-1-butenyl]phenoxy]ethyl]pyrrolidine) (SmithKline Beecham, USA), levormeloxifene (3,4-trans-2,2-dimethyl-3-phenyl-4-[4-(2-(pyrrolidin-1-yl)ethoxy)phenyl]-7-methoxychroman) (Novo Nordisk, A/S, Denmark) which is disclosed in Shalmi et al. WO 97/25034, WO 97/25035, WO 97/25037, WO 97/25038; and Korsgaard et al. WO 97/25036), GW5638 (described by Willson et al., 1997) and indole derivatives (disclosed by Miller et al., EP 0802183A1) Are also included, Iproxifen (TAT 59; (E)-4-[1-[4-[2-(dimethylamino)ethoxy]phenyl]-2-[4-(1-methylethyl)phenyl]-1-butenyl]phenol dihydrogen phosphate) from Taiho (Japan), ospemifene (FC 1271; ((Z)-2-[4-(4-chloro-1,2-diphenyl-1-butenyl)phenoxyl]ethanol) from available from Orion-Farmos Pharmaceutica, Finland, SERM 3471, HMR 3339 and HMR 3656 from Sanofi-Aventis (France), pipendoxifene (ERA 923) developed by Wyeth-Ayers, nonsteroidal estrogen derivatives described in WO 97/3283, fispemifene developed by QuatRx (USA) and CC 8490 developed by Celgene in USA.

Any SERM used as required for efficacy, as recommended by the manufacturer, can be used. Appropriate dosages are known in the art. Any other non steroidal antiestrogen commercially available can be used according to the invention. Any compound having activity similar to SERMs (example: raloxifene can be used).

SERMs administered in accordance with the invention are preferably administered in a dosage range between 0.01 to 5 mg/kg of body weight per day (preferably 0.05 to 1.0 mg/kg), with 5 mg per day, especially 10 mg per day, in two equally divided doses being preferred for a person of average body weight when orally administered, or in a dosage range between 0.003 to 3.0 mg/kg of body weight per day (preferably 0.015 to 0.3 mg/mL), with 1.5 mg per day, especially 3.0 mg per day, in two equally divided doses being preferred for a person of average body weight when parentally administered (i.e. intramuscular, subcutaneous or percutaneous administration). Preferably the SERMs are administered together with a pharmaceutically acceptable diluent or carrier as described below.

One preferred antiestrogen of the invention is fulvestrant (Faslodex; ICI 182 780; 7α-[9-(4,4,5,5,5-pentafluoro-pentylsulphinyl)nonyl]oestra-1,3,5(10)-triene-3,17β-diol) which is intramuscularly administered with the dosage of 250 mg per month available from AstraZeneca Canada Inc., Mississauga, Ontario, Canada. Other preferred antiestrogen is SH 646 from Schering AG, Germany With respect to all of the dosages recommended herein, the attending clinician should monitor individual patient response and adjust dosage accordingly.

EXAMPLES

Example 1

Example of Synthesis of the Preferred Compound of the Invention

Synthesis of acolbifene ((S)-(+)-7-hydroxy-3-(4'-hydroxyphenyl)-4-methyl-2-(4"-(2'"-piperidinoethoxy)phenyl)-2H-1-benzopyran hydrochloride, EM-01538, (EM-652.HCl)).

Scheme 1
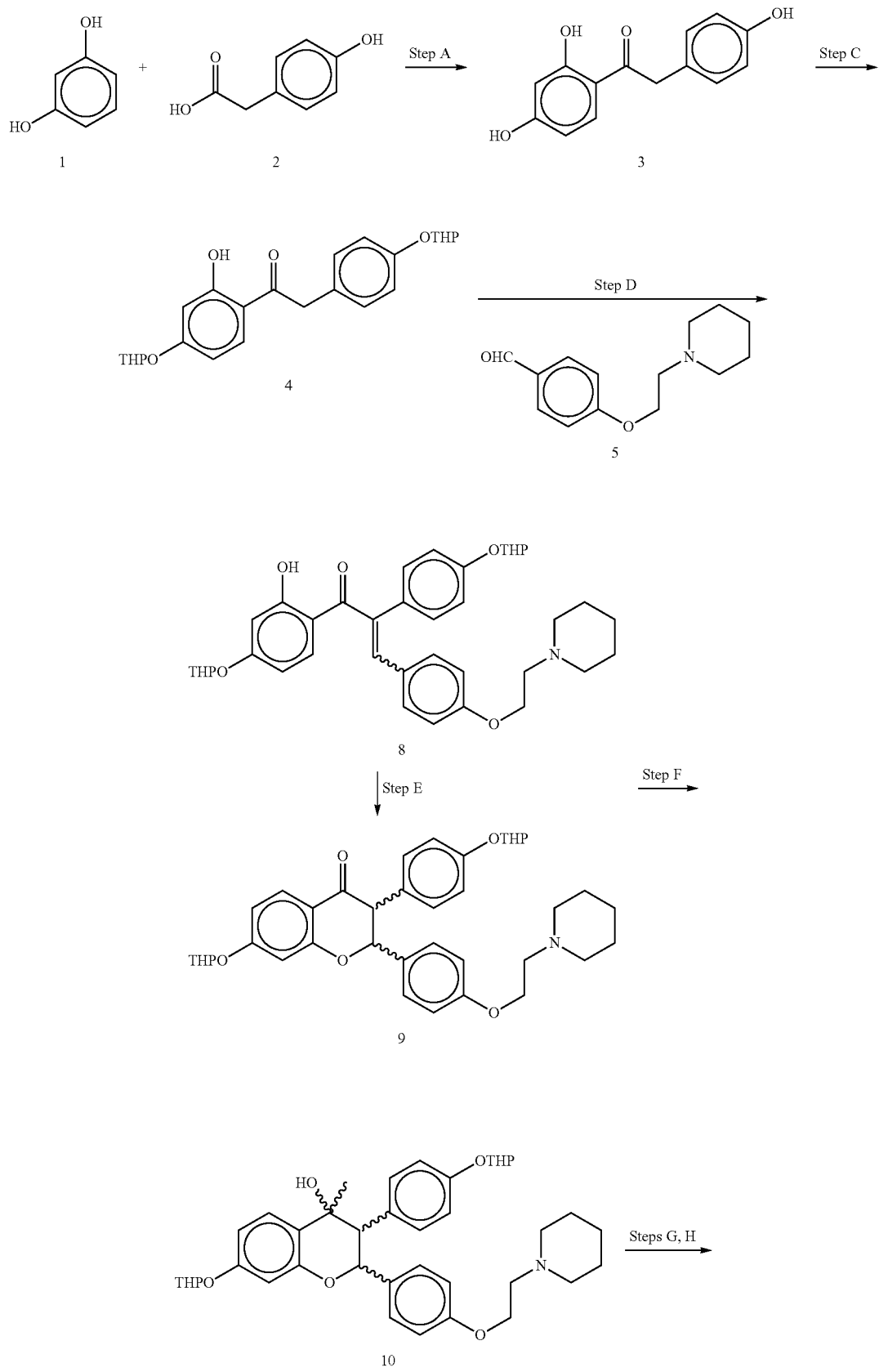

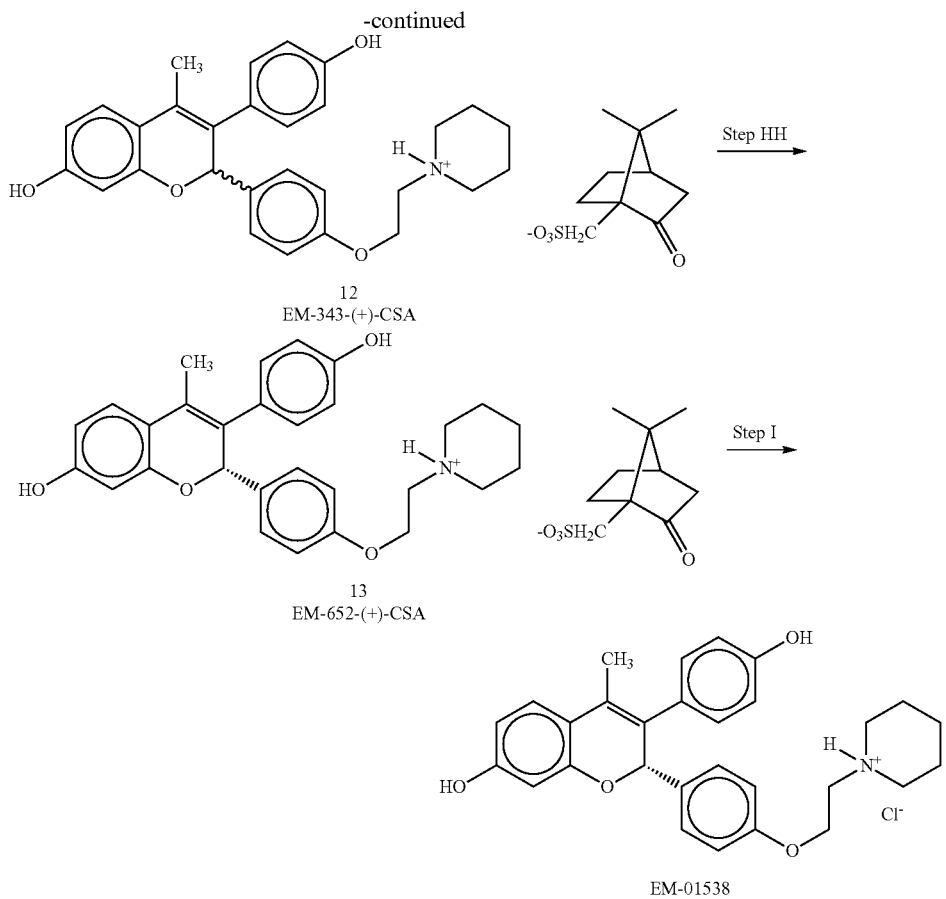

12
EM-343-(+)-CSA

13
EM-652-(+)-CSA

EM-01538

Step A: BF$_3$.Et$_2$O, toluene; 100° C.; 1 hour.
Step C: 3,4-dihydropyran, p-toluenesulfonic acid monohydrate, ethyl acetate; 25° C. under nitrogen, 16 hours, and then crystallization in isopropanol.
Steps D, E, and F:
(1) piperidine, toluene, Dean & Stark apparatus, reflux under nitrogen;
(2) 1,8-diazabicyclo[5,4,0]undec-7-ene, DMF, reflux 3 hours;
(3) CH$_3$MgCl, THF, −20 to 0° C. and then room temperature for 24 hours;
Steps G, H: (1S)-(+)-10-camphorsulfonic acid, acetone, water, toluene, room temperature, 48 hours.
Step HH: 95% ethanol, 70° C., then room temperature 3 days.
Step HHR: Recycling of mother liquor and wash of step HH (S)-10-camphorsulfonic acid, reflux; 36 hours, then room temperature for 16 hours.
Step I:
(1) DMF aq., Na$_2$CO$_3$, ethyl acetate;
(2) Ethanol, dilute HCl;
(3) Water.

Synthesis of 2-tetrahydropyranyloxy-4-hydroxy-2'-(4"-tetrahydropyranyloxy phenyl) acetophenone (4)

A suspension of 2,4-dihydroxy-2'-(4"-hydroxyphenyl)acetophenone 3 (97.6 g, 0.4 mole) (available from Chemsyn Science Laboratories, Lenexa, Kans.) in 3,4-dihydropyran (218 mL, 3.39 mole) and ethyl acetate (520 mL) was treated with p-toluenesulfonic acid monohydrate (0.03 g, 0.158 mmole) at about 25° C. The reaction mixture was stirred under nitrogen with no external heating for about 16 hours. The mixture was then washed with a solution of sodium bicarbonate (1 g) and sodium chloride (5 g) in water (100 mL). The phases were separated and the organic phase was washed with brine (20 mL). Each wash was back extracted with 50 mL ethyl acetate. All the organic phases were combined and filtered through sodium sulfate. Solvent (about 600 mL) was removed by distillation at atmospheric pressure and isopropanol (250 mL) was added. Additional solvent (about 300 mL) was distilled at atmospheric pressure and isopropanol (250 mL) was added. Additional solvent (about 275 mL) was distilled at atmospheric pressure and isopropanol (250 mL) was added. The solution was cooled at about 25° C. with stirring and after about 12 hours, the crystalline solid was filtered, washed with isopropanol and dried (116.5 g, 70%).

Synthesis of 4-hydroxy-4-methyl-2-(4'-[2"-piperidino]-ethoxy)phenyl-3-(4'''-tetrahydropyranyloxy) phenyl-7-tetrahydropyranyloxy-chromane (10)

A solution of 2-tetrahydropyranyloxy-4-hydroxy-2'-(4"-tetrahydropyranyloxy phenyl)acetophenone 4 (1 kg, 2.42 mole), 4-[2-(1-piperidino)ethoxy]benzaldehyde 5 (594 g, 2.55 mole) (available from Chemsyn Science Laboratories, Lenexa, Kans.) and piperidine (82.4 g, 0.97 mole) (available from Aldrich Chemical Company Inc., Milwaukee, Wis.) in toluene (8 L) was refluxed under nitrogen with a Dean &

Stark apparatus until one equivalent of water (44 mL) was collected. Toluene (6.5 L) was removed from the solution by distillation at atmospheric pressure. Dimethylformamide (6.5 L) and 1,8-diazabicyclo[5,4,0]undec-7-ene (110.5 g, 0.726 mole) were added. The solution was agitated for about 8 hours at room temperature to isomerize the chalcone 8 to chromanone 9 and then added to a mixture of water and ice (8 L) and toluene (4 L). The phases were separated and the toluene layer washed with water (5 L). The combined aqueous washes were extracted with toluene (3×4 L). The combined toluene extracts were finally washed with brine (3×4 L) concentrated at atmospheric pressure to 5.5 L and then cooled to −10° C. With continued external cooling and stirring under nitrogen, a 3M solution of methylmagnesium chloride in THF (2.5 L, 7.5 mole) (available from Aldrich Chemical Company Inc., Milwaukee, Wis.) was added, maintaining the temperature below 0° C. After all the Grignard reagent was added, the external cooling was removed and the mixture allowed warm to room temperature. The mixture was stirred at this temperature for about 24 hours. The mixture was again cooled to about −20° C. and with continued external cooling and stirring, saturated ammonium chloride solution (200 mL) was added slowly, maintaining the temperature below 20° C. The mixture was stirred for 2 hours and then added the saturated ammonium chloride solution (2 L) and toluene (4 L) and agitated for five minutes. The phases were separated and the aqueous layer extracted with toluene (2×4 L). The combined toluene extracts were washed with dilute hydrochloric acid until the solution became homogenous and then with brine (3×4 L). The toluene solution was finally concentrated at atmospheric pressure to 2 L. This solution was used directly in the next step.

Synthesis of (2R,S)-7-hydroxy-3-(4'-hydroxyphenyl)-4-methyl-2-(4"-[2'''-piperidino]ethoxy)phenyl)-2H-1-benzopyran (1S)-10-camphorsulphonic acid salt (±12)

To the toluene solution of 4-hydroxy-4-methyl-2-(4'-[−2"-piperidino]-ethoxy)-phenyl-3-(4'''-tetrahydropyranyloxy)phenyl-7-tetrahydropyranyloxy chromane (10) was added acetone (6 L), water (0.3 L) and (S)-10-camphorsulphonic acid (561 g, 2.42 mole) (available from Aldrich Chemical Company Inc. Milwaukee Wis.). The mixture was agitated under nitrogen for 48 hours after which time the solid (2R,S)-7-hydroxy-3-(4'-hydroxyphenyl)-4-methyl-2-(4"-[2'''-piperidino]ethoxy)phenyl)-2H-1-benzopyran (1S)-10-camphor sulphonic acid salt (12) was filtered, washed with acetone and dried (883 g). This material was used in the next (HH) step without further purification.

Synthesis of (2S)-7-hydroxy-3-(4'-hydroxyphenyl)-4-methyl-2-(4"-[2'''-piperidino]ethoxy)phenyl)-2H-1-benzopyran (1S)-10-camphorsulphonic acid salt (13, (+)-EM-652(1S)-CSA salt)

A suspension of (2R,S)-7-hydroxy-3-(4'-hydroxyphenyl)-4-methyl-2-(4"-[2'''-piperidino]ethoxy)phenyl)-2H-benzopyran (1S)-10-camphorsulphonic acid salt±12 (759 g) in 95% ethanol was heated with stirring to about 70° C. until the solid had dissolved. The solution was allowed to cool to room temperature with stirring then seeded with a few crystals of (2S)-7-hydroxy-3-(4'-hydroxyphenyl)-4-methyl-2-(4"-[2'''-piperidino]ethoxy)phenyl)-2H-1-benzopyran (1S)-10-camphorsulphonic acid salt 13. The solution was stirred at room temperature for about three days in total. The crystals were filtered, washed with 95% ethanol and dried (291 g, 76%). The de of the product was 94.2% and the purity 98.8%.

Synthesis of acolbifene ((S)-(+)-7-hydroxy-3-(4'-hydroxyphenyl)-4-methyl-2-(4"-(2'''-piperidinoethoxy)phenyl)-2H-1-benzopyran hydrochloride, EM-01538, (EM-652.HCl))

A suspension of compound 13 (EM-652-(+)-CSA salt, 500 mg, 0.726 mmol) in dimethylformamide (11 µL, 0.15 mmol) was treated with an 0.5 M aqueous sodium carbonate solution (7.0 mL, 3.6 mmol), and stirred for 15 min. The suspension was treated with ethyl acetate (7.0 mL) and stirred during 4 h. The organic phase was then washed with an aqueous saturated sodium carbonate solution (2×5 mL) and brine (1×5 mL) dried over magnesium sulfate, and concentrated. A solution of the resulting pink foam (EM-652) in ethanol (2 mL) was treated with 2 N hydrochloric acid (400 µL, 0.80 mmol), stirred for 1 h, treated with distilled water (5 mL), and stirred during 30 min. The resulting suspension was filtered, washed with distilled water (5 mL), dried in air and under high vacuum (65° C.) to give a creamy powder (276 mg, 77%): Fine off-white powder; Scanning calorimetry: Melting peak onset at 219° C., $\Delta H$=83 J/g; $[\alpha]^{24}_D$=154° in methanol 10 mg/mL; $^1$H NMR (300 MHz, CD$_3$OD) δ(ppm) 1.6 (broad, 2H, H-4'''), 1.85 (broad, 4H, H-3'''' and 5''''), 2.03 (s, 3H, CH$_3$), 3.0 and 3.45 (broad, 4H, H-2'''' and 6''''), 3.47 (t, J=4.9 Hz, 2H, H-3'''), 4.26 (t, J=4.9 Hz, 2H, H-2'''), 5.82 (s, 1H, H-2), 6.10 (d, J=2.3 Hz, 1H, H-8), 6.35 (dd, J=8.4, 2.43 Hz, 1H, H-6), 6.70 (d, J=8.6 Hz, 2H, H-3', and H-5'), 6.83 (d, J=8.7 Hz, 2H, H-3" and H-5"), 7.01 (d, J=8.5 Hz, 2H, H-2' and H-6'), 7.12 (d, J=8.4 Hz, 1H, H-5), 7.24 (d, J=8.6 Hz, 2H, H-2" and H-6"); $^{13}$C RMN (CD$_3$OD, 75 MHz) δ ppm 14.84, 22.50, 23.99, 54.78, 57.03, 62.97, 81.22, 104.38, 109.11, 115.35, 116.01, 118.68, 125.78, 126.33, 130.26, 130.72, 131.29, 131.59, 134.26, 154.42, 157.56, 158.96, 159.33. Elemental Composition: C, H, N, Cl: Theory; 70.51, 6.53, 2.84, 7.18, %. Found: 70.31, 6.75, 2.65, 6.89%.

Example 2

Materials and Methods

Animals

Female BALB/c mice (BALB/cAnNCrlBR) weighing 18-20 g were obtained from Charles-River, Inc. (St-Constant, Quebec, Canada) and housed 5 per cage in a temperature (23±1° C.)- and light (12 h light/day, lights on at 7:15)-controlled environment. The mice were fed rodent chow and tap water ad libitum. The animals were ovariectomized (OVX) under Isoflurane anesthesia via bilateral flank incisions and randomly assigned to groups of 10 animals. Ten mice were kept intact as controls.

Treatments

In the first experiment, the tested compounds (FIGS. 17 and 18), namely EM-652.HCl (acolbifene), lasofoxifene (as free base; active and inactive enantiomers) and raloxifene, were administered orally by gavage once daily at doses of 1, 3 or 10 µg/animal for 9 days, starting 2 days after ovariectomy. In the second experiment (Table 4), TSE 424 was administered orally by gavage once daily at doses of 1, 3, 10 or 30 µg/animal for 9 days, starting 2 days after ovariectomy. In both experiments, to evaluate the antiestrogenic activity, treatment with estrone ($E_1$, 0.06 µg, s.c. injection, twice daily) was started 5 days post-ovariectomy and was administered for a 6 day-period. Compounds were dissolved in ethanol (4% final concentration) and administered in 0.4% methylcellulose. Mice in the intact and OVX control groups received the vehicle alone (4% ETOH-0.4% methylcellulose) during the 9-day period. The animals were killed by exsanguination at the abdominal aorta on the 11$^{th}$ morning following ovariectomy. The uteri and vagina were rapidly dissected, weighed, and kept in 10% buffered formalin for further histologic examination.

Article 1: Results

Figure 17:
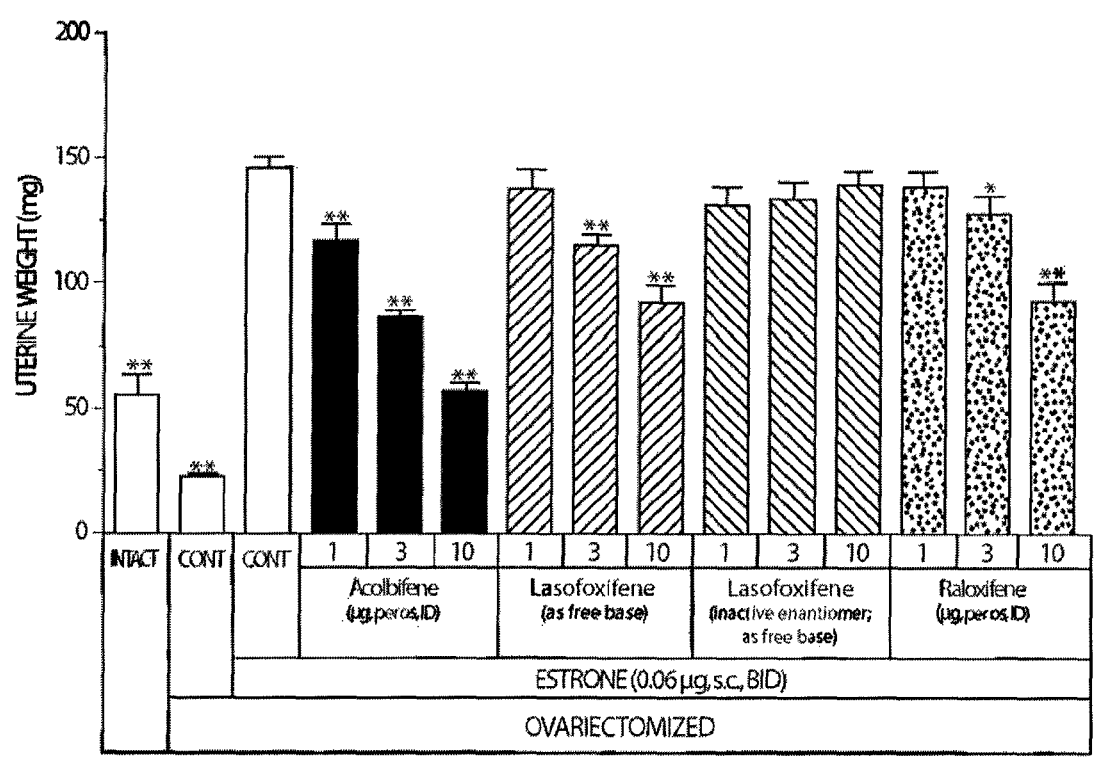
FIG. 17 shows the effect on uterine weight of increasing concentrations of EM-652.HCl (acolbifene), lasofoxifene (free base; active and inactive enantiomers) and raloxifene administered orally for 9 days to ovariectomized mice simultaneously treated with estrone. *$p<0.05$, **$p<0.01$ versus $E_1$-treated control.
Figure 18:
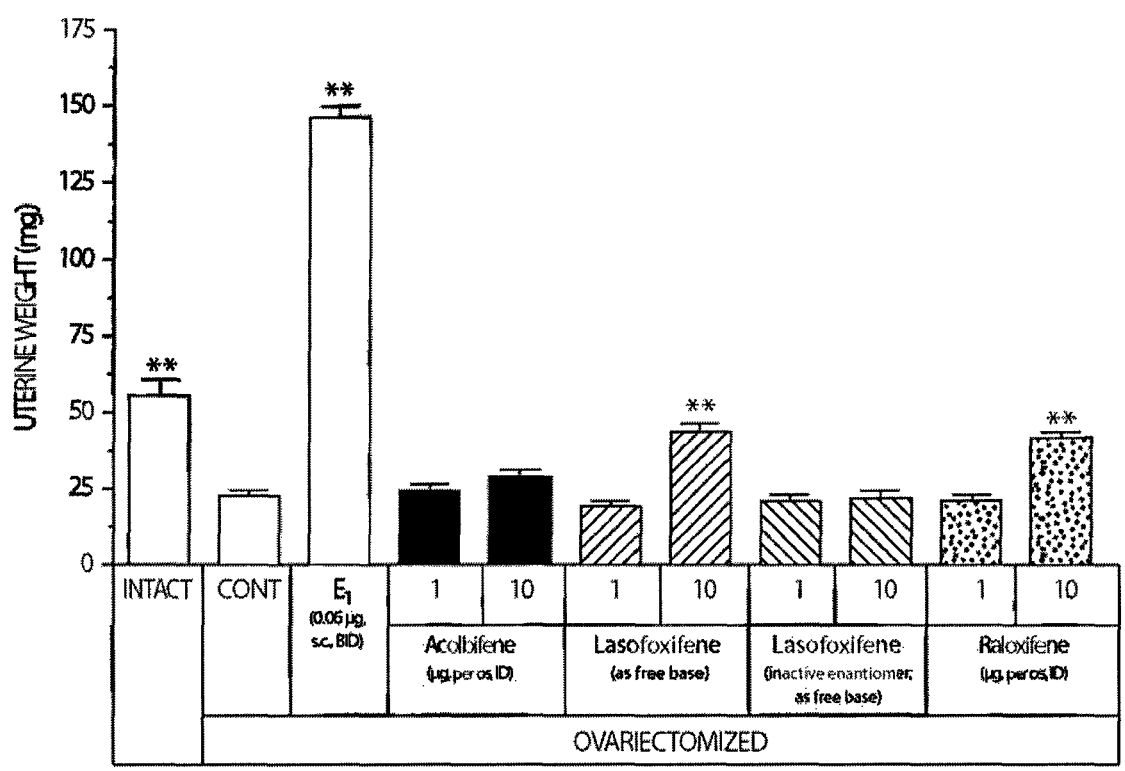
FIG. 18 shows the effect on uterine weight of 1 µg and 10 µg of EM-652.HCl (acolbifene), lasofoxifene (free base; active and inactive enantiomers) and raloxifene administered orally for 9 days to ovariectomized mice. **$p<0.01$ versus OVX control.

Experiment 1:

As illustrated in FIG. 17, EM-652.HCl (acolbifene) administered at the daily oral doses of 1 µg, 3 µg, and 10 µg caused respective 24%, 48%, and 72% inhibitions of estrone-stimulated uterine weight ($p<0.01$ for all doses versus control) while raloxifene administered at the same doses caused respective 6% (NS), 14% ($p<0.01$) and 43% ($p<0.01$) inhibitions of this parameter. Lasofoxifene (as free base), on the other hand, had no inhibitory effect at the lowest dose used while it caused respective 25% ($p<0.01$) and 44% ($p<0.01$) inhibitions of estrone-stimulated uterine weight at the daily doses of 3 µg and 10 µg. The inactive enantiomer of lasofoxifene exerted no inhibitory effect on this parameter at any dose used.

When compounds were administered alone (in the absence of estrone) to ovariectomized mice at the daily oral doses of 1 µg and 10 µg, EM-652.HCl had no significant stimulatory effect on uterine weight at both doses used, while treatment with 10 µg of lasofoxifene and raloxifene caused respective 93% ($p<0.01$) and 85% ($p<0.01$) stimulations of uterine weight (FIG. 18), thus indicating an estrogenic effect of these latter compounds on this parameter. Similarly, EM-652.HCl exerted no significant stimulatory effect on vaginal weight (FIG. 18) while administration of 10 µg of lasofoxifene and raloxifene caused respective 73% ($p<0.01$) and 56% ($p<0.01$) stimulations of vaginal weight. On the other hand, the inactive enantiomer of lasofoxifene had no stimulatory effect on uterine and vaginal weight.

Experiment 2:

As shown in Table 4, TSE 424 administered at the daily oral doses of 1 µg, 3 µg, 10 µg or 30 µg caused respective 12% (NS), 47%, 74%, and 94% inhibitions of estrone-stimulated uterine weight ($p<0.01$ for the three highest doses versus $E_1$-control). When the compound was administered alone (in the absence of estrone) to ovariectomized mice at the daily oral doses of 3 µg and 30 µg, TSE 424 had no significant stimulatory effect on uterine weight at both doses used (Table 4).

TABLE 4

Effect on uterine weight of increasing concentrations of TSE 424 administered orally for 9 days to ovariectomized mice simultaneously treated or not with estrone. **$p < 0.01$ versus $E_1$-treated control.

| TREATMENT | UTERINE WEIGHT (mg) |
|---|---|
| INTACT | 54.6 ± 12.5** |
| OVX | 15.6 ± 1.3** |
| OVX + $E_1$ | 118.3 ± 6.0 |
| OVX + $E_1$ + TSE 424 1 µg | 105.5 ± 6.1 |
| OVX + $E_1$ + TSE 424 3 µg | 69.7 ± 4.4** |
| OVX + $E_1$ + TSE 424 10 µg | 42.1 ± 2.7** |
| OVX + $E_1$ + TSE 424 30 µg | 21.7 ± 1.7** |
| OVX + TSE 424 3 µg | 18.3 ± 1.2 |
| OVX + TSE 424 30 µg | 17.7 ± 1.6 |

Example 3

Preventive Effects on Bone Loss, Serum Lipids and Total Body Fat

Animals and Treatment

Ten to twelve week-old female Sprague-Dawley rats (Crl:CD(SD)Br) (Charles River Laboratory, St-Constant, Canada) weighing approximately 220-270 g at start of treatment were used. The animals were acclimatized to the environmental conditions (temperature: 22±3° C.; humidity: 50±20%; 12-h light-12-h dark cycles, lights on at 07:15 h) for at least 1 week before starting the experiments. The animals were housed individually and were allowed free access to tap water and a pelleted certified rodent feed (Lab Diet 5002, Ralston Purina, St-Louis, Mo.). Experiments were conducted in an animal facility approved by the Canadian Council on Animal Care (CCAC) and the Association for Assessment and Accreditation of Laboratory Animal Care (AAALAC) in accordance with the CCAC Guide for Care and Use of Experimental Animals.

In a first experiment, one hundred fifty-four rats were randomly distributed between 11 groups of 14 animals each as follows: 1) Intact control; 2) OVX control; 3) OVX+$E_2$ (1 mg/kg); 4) OVX+EM-652.HCl (2.5 mg/kg); 5) OVX+$E_2$+EM-652.HCl; 6) OVX+dehydroepiandrosterone (DHEA; 80 mg/kg); 7) OVX+DHEA+EM-652.HCl; 8) OVX+DHEA+$E_2$; 9) OVX+DHEA+$E_2$+EM-652.HCl; 10) OVX+GW 5638; 11) OVX+$E_2$+GW 5638. On Day 1 of the study, the animals of the appropriate groups were bilaterally ovariectomized (OVX) under isoflurane anesthesia. The DHEA was applied topically on the dorsal skin as a solution in 50% ethanol-50% propylene glycol while the other tested compounds were administered as suspension in 0.4% methylcellulose by oral gavage. Treatments were initiated on Day 2 of the study and were performed once daily during 3 months.

In the second experiment, one hundred thirty-two rats were randomly distributed between 9 groups of 14 or 15 animals each as follows: 1) Intact control; 2) OVX control; 3) OVX+Premarin (0.25 mg/kg); 4) OVX+EM-652.HCl (2.5 mg/kg); 5) OVX+Premarin+EM-652.HCl; 6) OVX+TSE 424 (2.5 mg/kg); 7) OVX+Premarin+TSE 424; 8) OVX+lasofoxifene (tartrate salt; racemate; 2.5 mg/kg); 9) OVX+Premarin+lasofoxifene. On Day 1 of the study, the animals of the appropriate groups were bilaterally OVX under isoflurane anesthesia. Tested compounds were administered as suspension in 0.4% methylcellulose by oral gavage. Treatments were initiated on Day 2 of the study and were performed once daily during 26 weeks. In both experiments, animals not receiving a test article were treated with the appropriate vehicle alone during the same period.

Bone Mineral Density Measurements

After 3 months (experiment 1) or 26 weeks (experiment 2) of treatment, individual rats under Isoflurane anesthesia had their whole body skeleton and lumbar spine scanned using dual energy x-ray absorptiometry (DEXA; QDR 4500A, Hologic, Waltham, Mass.) and a Regional High Resolution Scan software. The bone mineral density (BMD) of the lumbar spine (vertebrae L2 to L4) and the total body composition (fat percentage) were determined.

Serum Assays

After 3 months (experiment 1) or 26 weeks (experiment 2) of treatment, blood samples were collected at the jugular vein from overnight fasted animals (under Isoflurane anesthesia). Samples were processed for serum preparation and frozen at −80° C. until assay. Serum cholesterol levels and alkaline phospatase activity (ALP) were determined using the Boehringer Mannheim Diagnostic Hitachi 911 Analyzer (Boehringer Mannheim Diagnostic Laboratory Systems).

Statistical Analyses

Data are expressed as means±SEM. Statistical significance was determined according to the multiple-range test of Duncan-Kramer (Kramer 1956).

Results

As shown in Table 5, 3 months after ovariectomy, BMD of the lumbar spine was 10% lower in OVX control animals than in intact controls ($p<0.01$). At the doses used, the administration of estradiol and EM-652.HCl alone prevented lumbar spine BMD loss by 98% ($p<0.01$) and 65% ($p<0.05$), respectively, while the combined treatment with $E_2$ and EM-652.HCl prevented the OVX-induced decrease in lumbar spine BMD by 61% ($p<0.05$). On the other hand, while the administration of DHEA alone prevented lumbar spine BMD by 43% ($p<0.05$), the combined treatment with DHEA+$E_2$+EM-652.HCl prevented the OVX-induced decrease in lumbar spine BMD by 91% and led to BMD value not different from intact controls.

In Table 6, 26 weeks after ovariectomy, BMD of the lumbar spine was 18% lowered compared to intact controls ($p<0.01$). The administration of Premarin, EM-652.HCl, TSE 424 and lasofoxifene alone prevented lumbar spine BMD by 54%, 62%, 49% and 61%, respectively (all $p<0.01$ versus OVX controls). The addition of Premarin to EM-652.HCl, TSE 424 or lasofoxifene led to lumbar spine BMD values not significantly different from those obtained with the administration of each SERM alone (Table 6). Similarly, the addition of DHEA to $E_2$ or to EM-652.HCl completely prevented the OVX-induced decrease in lumbar spine BMD (Table 5). The positive effect of DHEA on BMD is also supported by its effect on serum alkaline phosphatase activity (ALP), a marker of bone formation and turnover. ALP activity was increased from 73±6 IU/L in OVX control animals to 224±18 IU/L, 290±27 IU/L, 123±8 IU/L and 261±20 IU/L (all $p<0.01$) in DHEA-, DHEA+EM-652.HCl-, DHEA+$E_2$- and DHEA+$E_2$+EM-652.HCl-treated animals, respectively, thus suggesting a stimulatory effect of DHEA on bone formation (Table 7).

In addition to the preventive effects on bone loss, the administration of EM-652.HCl, TSE 424, lasofoxifene, GW 5638, DHEA and $E_2$ exerts some beneficial effects on total body fat percentage and serum lipids. After three months of ovariectomy, total body fat was increase by 22% ($p<0.05$; Table 7). The administration of EM-652.HCl completely prevented the OVX-induced fat percentage increase while the addition of DHEA and/or $E_2$ to the SERM led to fat percentage values below those observed in intact control animals. After 26 weeks of ovariectomy, the 40% fat increase induced by estrogen deficiency was reversed by 74%, 78%, 75% and 114% following the administration of Premarin, EM-652.HCl, TSE 424 or lasofoxifene, respectively, while the addition of Premarin to each SERM completely prevented the OVX-induced fat percentage increase (Table 8).

As shown in Table 7, three months after ovariectomy, a 22% increase in serum cholesterol levels was observed in OVX control rats compared to intact controls ($p<0.01$). In fact, serum cholesterol was increased from 2.01±0.11 mmol/L in intact animals to 2.46 V 0.08 mmol/L in OVX controls. The administration of $E_2$ or DHEA alone decrease serum cholesterol levels to 1.37±0.18 mmol/L and 1.59±0.10 mmol/L, respectively, while the administration of EM-652.HCl alone or in combination with $E_2$ and/or DHEA led to cholesterol levels significantly lower (between 0.65 to 0.96 mmol/L) than those found in intact animals (2.01±0.11 mmol/L). Similarly, the administration of GW 5638, TSE 424 and lasofoxifene alone or in combination with $E_2$ or Premarin completely prevented the OVX-induced increase on serum cholesterol levels and led to values lower than those found in intact animals (Tables 7 and 8).

TABLE 5

EFFECT ON PREVENTION OF BONE LOSS FOLLOWING 3 MONTH-TREATMENT WITH ESTRADIOL, EM-652.HCl, GW 5638 OR DHEA, ADMINISTERED ALONE OR IN COMBINATION, TO OVARIECTOMIZED FEMALE RATS

| ARTICLE II. ARTICLE IV. TREATMENT | ARTICLE III. LUMBAR SPINE | |
|---|---|---|
| | BMD (g/cm$^2$) | Prevention of Bone Loss (%) |
| 1) Intact | 0.2461 ± 0.0049** | 100 |
| OVX | 0.2214 ± 0.0044 | — |
| OVX + $E_2$ | 0.2457 ± 0.0049** | 98 |
| OVX + EM-652.HCl | 0.2374 ± 0.0027* | 65 |
| OVX + EM-652.HCl + $E_2$ | 0.2364 ± 0.0037* | 61 |
| Section 1.02 OVX + DHEA | 0.2321 ± 0.0034 | 43 |
| Section 1.03 OVX + DHEA + EM 652.HCl | 0.2458 ± 0.0037** | 99 |
| Section 1.04 OVX + DHEA + $E_2$ | 0.2496 ± 0.0029** | 114 |
| Section 1.05 OVX + DHEA + $E_2$ + EM-652.HCl | 0.2439 ± 0.0043** | 91 |
| Section 1.06 OVX + GW 5638 | 0.2299 ± 0.0060 | 34 |
| Section 1.07 OVX + GW 5638 + $E_2$ | 0.2344 ± 0.0054 | 53 |

*, $p < 0.05$;
**, $p < 0.01$, experimental versus OVX control rats.

TABLE 6

EFFECT ON PREVENTION OF BONE LOSS FOLLOWING 26 WEEK-TREATMENT WITH PREMARIN, EM-652.HCl, TSE 424 OR LASOFOXIFENE, ADMINISTERED ALONE OR IN COMBINATION WITH PREMARIN, TO OVARIECTOMIZED FEMALE RATS

| ARTICLE V. ARTICLE VII. TREATMENT | ARTICLE VI. LUMBAR SPINE | |
|---|---|---|
| | BMD (g/cm2) | Prevention of Bone Loss (%) |
| 1) Intact | 0.2482 ± 0.0067** | 100 |
| OVX | 0.2035 ± 0.0035 | — |
| OVX + Premarin | 0.2277 ± 0.0028** | 54 |
| OVX + EM-652.HCl | 0.2311 ± 0.0040** | 62 |
| OVX + Premarin + EM-652.HCl | 0.2319 ± 0.0057** | 64 |
| Section 1.08 OVX + TSE 424 | 0.2252 ± 0.0058** | 49 |
| Section 1.09 OVX + Premarin + TSE 424 | 0.2223 ± 0.0046** | 42 |
| Section 1.10 OVX + lasofoxifene | 0.2307 ± 0.0040** | 61 |
| Section 1.11 OVX + Premarin + lasofoxifene | 0.2357 ± 0.0035** | 72 |

**, $p < 0.01$, experimental versus OVX control rats.

TABLE 7

EFFECT ON TOTAL BODY FAT PERCENTAGE, SERUM
CHOLESTEROL LEVELS AND ALKALINE PHOSPHATASE
ACTIVITY FOLLOWING 3 MONTH-TREATMENT WITH
ESTRADIOL, EM-652.HCl, GW 5638 OR DHEA,
ADMINISTERED ALONE OR IN COMBINATION, TO
OVARIECTOMIZED FEMALE RATS

| ARTICLE VIII<br>ARTICLE XII<br>TREATMENT | ARTICLE IX TOTAL FAT (%) | ARTICLE X CHOLES-TEROL (mmol/L) | ARTICLE XI ALP (IU/L) |
|---|---|---|---|
| 1) Intact | 24.0 ± 1.5* | 2.01 ± 0.11** | 39 ± 2** |
| OVX | 29.2 ± 1.5 | 2.46 ± 0.08 | 73 ± 6 |
| OVX + $E_2$ | 19.5 ± 2.5** | 1.37 ± 0.18** | 59 ± 4 |
| OVX + EM-652.HCl | 23.2 ± 1.4** | 0.87 ± 0.04** | 91 ± 6* |
| OVX + EM-652.HCl + $E_2$ | 20.4 ± 1.4** | 0.96 ± 0.07** | 92 ± 5* |
| Section 1.12 OVX + DHEA | 17.3 ± 1.5** | 1.59 ± 0.10** | 224 ± 18** |
| Section 1.13 OVX + DHEA + EM-652.HCl | 18.0 ± 1.1** | 0.65 ± 0.06** | 290 ± 27** |
| Section 1.14 OVX + DHEA + $E_2$ | 15.8 ± 1.3** | 1.08 ± 0.08** | 123 ± 8** |
| Section 1.15 OVX + DHEA + $E_2$ + EM-652.HCl | 19.2 ± 1.6** | 0.71 ± 0.08** | 261 ± 20** |
| Section 1.16 OVX + GW 5638 | 21.9 ± 1.4** | 1.14 ± 0.08** | 72 ± 6 |
| Section 1.17 OVX + GW 5638 + $E_2$ | 23.2 ± 1.2** | 0.91 ± 0.07** | 80 ± 6 |

*, $p < 0.05$;
**, $p < 0.01$, experimental versus OVX control rats.

TABLE 8

EFFECT ON TOTAL BODY FAT PERCENTAGE, SERUM
CHOLESTEROL LEVELS AND ALKALINE PHOSPHATASE
ACTIVITY FOLLOWING 26 WEEK-TREATMENT WITH
PREMARIN, EM-652.HCl, TSE 424 OR LASOFOXIFENE,
ADMINISTERED ALONE OR IN COMBINATION WITH
PREMARIN, TO OVARIECTOMIZED FEMALE RATS

| ARTICLE XIII<br>ARTICLE XVII<br>TREATMENT | ARTICLE XIV TOTAL FAT (%) | ARTICLE XV CHOLES-TEROL (mmol/L) | ARTICLE XVI ALP (IU) |
|---|---|---|---|
| 1) Intact | 25.5 ± 1.8** | 2.11 ± 0.11** | 33 ± 2* |
| OVX | 35.7 ± 1.6 | 2.51 ± 0.09 | 60 ± 6 |
| OVX + Premarin | 28.2 ± 1.8** | 1.22 ± 0.07** | 49 ± 3 |
| OVX + EM-652.HCl | 27.7 ± 1.4** | 0.98 ± 0.06** | 78 ± 4 |
| OVX + EM-652.HCl + Premarin | 25.7 ± 2.2** | 1.10 ± 0.07** | 81 ± 6 |
| Section 1.18 OVX + TSE 424 | 28.0 ± 1.8** | 1.15 ± 0.05** | 85 ± 6 |
| Section 1.19 OVX + TSE 424 + Premarin | 25.7 ± 1.7** | 1.26 ± 0.14** | 98 ± 22** |
| Section 1.20 OVX + lasofoxifene | 24.1 ± 1.3** | 0.60 ± 0.02** | 116 ± 9** |
| Section 1.21 OVX + lasofoxifene + Premarin | 23.8 ± 1.9** | 0.81 ± 0.12** | 107 ± 6** |

*, $p < 0.05$;
**, $p < 0.01$, experimental versus OVX control rats.

Example 4

Preventive Effects on Bone Loss Following Treatment with the SERMs Em-652.HCl (Acolbifene), TSE-424 and ERA-923, Administered Alone and in Combination with DHEA to Ovariectomized Female Rats Animals and Treatment Ten to twelve week-old female Sprague-Dawley rats (Crl:CD(SD)Br) (Charles River Laboratory, St-Constant, Canada) weighing approximately 220-270 g at start of treatment were used. The animals were acclimatized to the environmental conditions (temperature: 22±3° C.; humidity: 50±20%; 12-h light-12-h dark cycles, lights on at 07:15 h) for at least 1 week before starting the experiments. The animals were housed individually and were allowed free access to tap water and a pelleted certified rodent feed (Lab Diet 5002, Ralston Purina, St-Louis, Mo.). Experiments were conducted in an animal facility approved by the Canadian Council on Animal Care (CCAC) and the Association for Assessment and Accreditation of Laboratory Animal Care (AAALAC) in accordance with the CCAC Guide for Care and Use of Experimental Animals.

One hundred twenty-six rats were randomly distributed between 9 groups of 14 animals each as follows: 1) Intact control; 2) OVX control; 3) OVX+EM-652.HCl (2.5 mg/kg); 4) OVX+TSE-424 (EM-4803, 2.5 mg/kg); 5) OVX+ERA-923 (EM-3527, 2.5 mg/kg); 6) OVX+dehydroepiandrosterone (DHEA; 80 mg/kg); 7) OVX+DHEA+EM-652.HCl; 8) OVX+DHEA+TSE-424; 9) OVX+DHEA+ERA-923. On Day 1 of the study, the animals of the appropriate groups were bilaterally ovariectomized (OVX) under isoflurane anesthesia. The DHEA was applied topically on the dorsal skin as a solution in 50% ethanol-50% propylene glycol while the tested SERMs were administered as suspension in 0.4% methylcellulose by oral gavage. Treatments were initiated on Day 2 of the study and were performed once daily during 5 weeks.

Bone Mineral Density Measurements

After 5 weeks of treatment, individual rats under Isoflurane anesthesia had their lumbar spine, femur and tibia scanned using dual energy x-ray absorptiometry (DEXA; QDR 4500A, Hologic, Waltham, Mass.) and a Regional High Resolution Scan software. The bone mineral density (BMD) of the lumbar spine (vertebrae L2 to L4), distal femoral metaphysis (DFM) and proximal tibial metaphysis (PTM) were determined.

Statistical Analyses

Data are expressed as means±SEM. Statistical significance was determined according to the multiple-range test of Duncan-Kramer {Kramer, 1956 #37421.

Results

As shown in Table 9, after 5 weeks of ovariectomy, BMD of the lumbar spine was 9% lower in Ovx control animals than in intact controls. At the dose used the administration of the SERMs: EM-652.HCl, TSE-424 or ERA-923 alone prevented lumbar spine BMD loss by 86%, 53% and 78%, respectively. On the other hand, the administration of DHEA alone prevented lumbar spine BMD loss by 44%, while the combined treatment with DHEA+EM-652.HCl, DHEA+TSE-424 or DHEA+ERA-923 prevented the OVX-induced decrease in lumbar spine BMD by 94%, 105% and 105%, respectively.

Bone mineral density of the distal femoral metaphysis (DFM) was decreased by 10% after 5 weeks of ovariectomy (Table 9). The administration of the SERMs: EM-652.HCl, TSE-424 or ERA-923 alone prevented DFM BMD loss by 95%, 70% and 83%, respectively. On the other hand, administration of DHEA alone prevented DFM BMD loss by 71%, while the combined treatment with DHEA+EM-652.HCl, DHEA+TSE-424 or DHEA+ERA-923 completely prevented the OVX-induced decrease in DFM BMD and led to DFM BMD values higher than those observed in intact control animals. Similar results were obtained on proximal tibial metaphysis BMD (Table 9).

TABLE 9

EFFECT ON PREVENTION OF BONE LOSS FOLLOWING 5 WEEK-TREATMENT WITH THE SERMs
EM-652.HCI, TSE-424 AND ERA-923, ADMINISTERED ALONE OR IN COMBINATION WITH DHEA, TO
OVARIECTOMIZED FEMALE RATS

| TREATMENT | LUMBAR SPINE (L2-L4) | | DISTAL FEMORAL METAPHYSIS (DFM) | | PROXIMAL TIBIAL METAPHYSIS (PFM) | |
|---|---|---|---|---|---|---|
| | BMD (g/cm$^2$) | Prevention of Bone Loss (%) | BMD (g/cm$^2$) | Prevention of Bone Loss (%) | BMD (g/cm$^2$) | Prevention of Bone Loss (%) |
| Intact | 0.2261 ± 0.0046 | 100 | 0.3024 ± 0.0040 | 100 | 0.2828 ± 0.0032 | 100 |
| Ovx | 0.2051 ± 0.0037 | — | 0.2709 ± 0.0036 | — | 0.2560 ± 0.0028 | — |
| Ovx + EM-652.HCI | 0.2232 ± 0.0031 | 86 | 0.3008 ± 0.0055 | 95 | 0.2806 ± 0.0035 | 92 |
| Ovx + TSE-424 | 0.2162 ± 0.0035 | 53 | 0.2929 ± 0.0042 | 70 | 0.2750 ± 0.0039 | 71 |
| Ovx + ERA-923 | 0.2214 ± 0.0029 | 78 | 0.2969 ± 0.0029 | 83 | 0.2805 ± 0.0034 | 91 |
| Ovx + DHEA | 0.2144 ± 0.0028 | 44 | 0.2934 ± 0.0046 | 71 | 0.2672 ± 0.0041 | 42 |
| Ovx + DHEA + EM-652.HCI | 0.2249 ± 0.0023 | 94 | 0.3122 ± 0.0045 | 131 | 0.2867 ± 0.0047 | 115 |
| Ovx + DHEA + TSE-424 | 0.2271 ± 0.0030 | 105 | 0.3099 ± 0.0040 | 124 | 0.2833 ± 0.0034 | 102 |
| Ovx + DHEA + ERA-923 | 0.2271 ± 0.0030 | 105 | 0.3072 ± 0.0053 | 115 | 0.2817 ± 0.0034 | 96 |

Example 5

Effect of Compounds of the Invention on Alkaline Phosphatase Activity in Human Endometrial Adenocarcinoma Ishikawa Cells Materials Maintenance of Stock Cell Cultures The human Ishikawa cell line derived from a well differentiated endometrial adenocarcinoma was kindly provided by Dr. Erlio Gurpide, The Mount Sinai Medical Center, New York, N.Y. The Ishikawa cells were routinely maintained in Eagle's Minimum Essential Medium (MEM) containing 5% (vol/vol) FBS (Fetal Bovine Serum) and supplemented with 100 U/mL penicillin, 100 μg/mL streptomycin, 0.1 mM non-essential amino acids solution. Cells were plated in Falcon T75 flasks at a density of 1.5×10$^6$ cells at 37° C.

Cell Culture Experiments

Twenty four hours before the start of the experiment, the medium of near confluent Ishikawa cells was replaced by fresh estrogen-free basal medium (EFBM) consisting of a 1:1 (v:v) mixture of phenol red-free Ham's F-12 and Dulbecco's Modified Eagle's Medium (DMEM) supplemented with 100 U/mL penicillin, 100 μg/mL streptomycin, 2 mM glutamine, and 5% FBS treated twice with dextran-coated charcoal to remove endogenous steroids. Cells were then harvested by 0.1% pancreatin (Sigma) and 0.25 mM HEPES, resuspended in EFBM and plated in Falcon 96, well flat-bottomed microtiter plates at a density of 2.2×10$^4$ cells/well in a volume of 100 μl and allowed to adhere to the surface of the plates for 24 h. Thereafter, medium was replaced with fresh EFBM containing the indicated concentrations of compounds in a final volume of 200 μl. Cells were incubated for five days, with a medium change after 48 h.

Alkaline Phosphatase Assay

At the end of the incubation period, microtiter plates were inverted and growth medium was decanted. The plates were rinsed with 200 μl by well of PBS (0.15 M NaCl, 10 mM sodium phosphate, pH 7.4). PBS was then removed from the plates while carefully leaving some residual PBS, and the wash procedure was repeated once. The buffered saline was then decanted, and the inverted plates were blotted gently on a paper towel. Following replacement of the covers, the plates were placed at −80° C. for 15 min followed by thawing at room temperature for 10 min. The plates were then placed on ice, and 50 μl of an ice-cold solution containing 5 mM p-nitrophenyl phosphate, 0.24 mM MgCl$_2$, and 1 M diethanolamine (pH 9.8) were added. Plates were then warmed to room temperature, and the yellow color from the production of p-nitrophenyl was allowed to develop (8 min). Plates were monitored at 405 nm in an enzyme-linked immunosorbent assay plate reader (BIO-RAD, model 2550 EIA Reader).

Calculations

Dose-response curves as well as IC$_{50}$ values were calculated using a weighted iterative nonlinear squares regression.

TABLE 10

| NAME | CODE NAME | STRUCTURE | Maximal stimulation of alkaline phosphatase % of 1 nM $E_2$ stimulation * (nb of experiments) | Inhibition of 1 nM $E_2$-induced stimulation of alkaline phosphatase $IC_{50}$ (nM) (nb of experiments) | Maximal inhibition of 1 nM $E_2$-induced stimulation of alkaline phosphatase (nb of experiments) |
|---|---|---|---|---|---|
| EM-652.HCl (acolbifene) | EM-652.HCl; (EM-1538) | 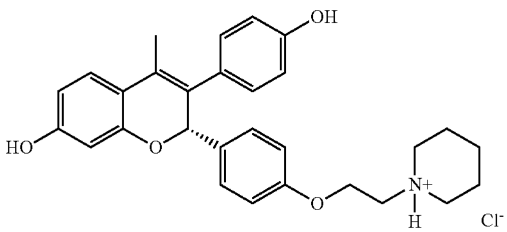 [SMILES: CC1=C(c2ccc(O)cc2)[C@H](c2ccc(OCC[NH+]3CCCCC3)cc2)Oc2cc(O)ccc21 ; [Cl-]] | 1.88 ± 0.26 (22) | 1.52 ± 0.22 (18) | 98.97 ± 0.174 (18) |
| OH-toremifene | EM-880 | 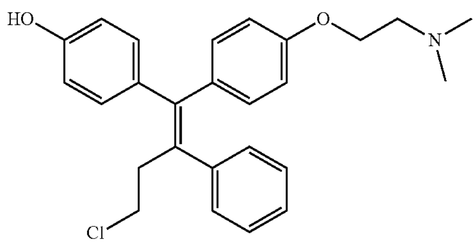 [SMILES: CN(C)CCOc1ccc(/C(=C(/CCCl)c2ccccc2)c2ccc(O)cc2)cc1] | 29.6 ± 2.1 (6) | 72.1 ± 7.6 (3) | 75.73 ± 3.52 (3) |
| GW-5638 | EM-1796 | 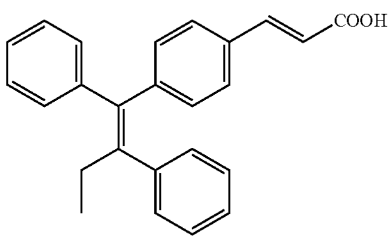 [SMILES: CC/C(=C(\c1ccccc1)c1ccc(/C=C/C(=O)O)cc1)c1ccccc1] | 7.75 ± 5.5 (2) | No inhibition | |
| raloxifene LY 156758 | EM-1105 | 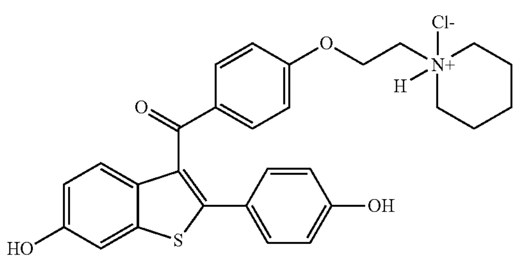 | 12.8 ± 1.7 (8) | 3.39 ± 0.9 (6) | 94.31 ± 1.74 (5) |
| LY 353381 | EM-1665 | 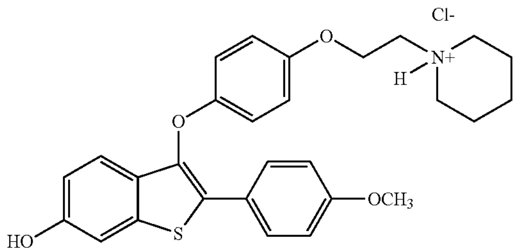 [SMILES: [Cl-] ; COc1ccc(-c2sc3cc(O)ccc3c2Oc2ccc(OCC[NH+]3CCCCC3)cc2)cc1] | 15.5 ± 0.25 (5) | 1.87 ± 0.07 (2) | 90.25 ± 0.127 (2) |

TABLE 10-continued

| NAME | CODE NAME | STRUCTURE | Maximal stimulation of alkaline phosphatase % of 1 nM $E_2$ stimulation * (nb of experiments) | Inhibition of 1 nM $E_2$-induced stimulation of alkaline phosphatase $IC_{50}$ (nM) (nb of experiments) | Maximal inhibition of 1 nM $E_2$-induced stimulation of alkaline phosphatase (nb of experiments) |
|---|---|---|---|---|---|
| lasofoxifene (free base) | EM-3114 | 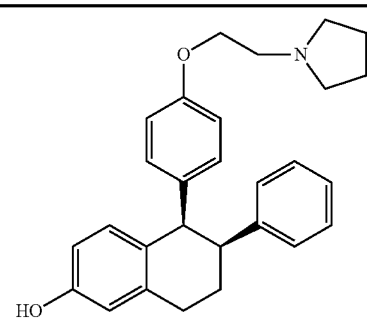 | 17.9 (1) | 4.24 (1) | 85.14 (1) |
| ERA-923 | EM-3527 | 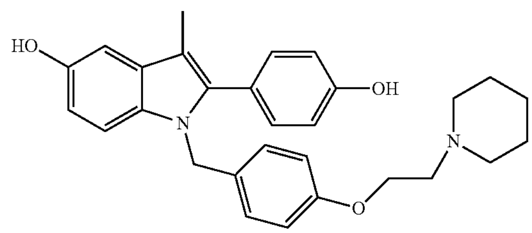 [SMILES: Cc1c(-c2ccc(O)cc2)n(Cc2ccc(OCCN3CCCCC3)cc2)c2ccc(O)cc12] | 0.6 (1) | 5.84 (1) | 100.16 (1) |

* % of 1 nM $E_2$ stimulation = OD 405 nm compound-OD 405 nm basal/OD 405 nm 1 nM $E_2$-OD 405 nm basal
Please see also Labrie et al. 1999.

Example 6

Effect of EM-652.HCl (Acolbifene), TSE 424, and Lasofoxifene on the Proliferation of Human Breast Cancer MCF-7 Cells Methods:

Maintenance of Stock Cell Cultures

MCF-7 human breast cancer cells were obtained from the American Type Culture Collection # HTB 22 at passage 147 and routinely grown in phenol red-free Dulbecco's Modified Eagle's-Ham's F12 medium, the supplements mentioned above and 5% FBS. The MCF-7 human breast adenocarcinoma cell line was derived from the pleural effusion of a Caucasian 69-year-old female patient. MCF-7 cells were used between passages 148 and 165 and subcultured weekly.

Cell Proliferation Studies

Cells in their late logarithmic growth phase were harvested with 0.1% pancreatin (Sigma) and resuspended in the appropriate medium containing 50 ng bovine insulin/mL and 5% (v/v) FBS treated twice with dextran-coated charcoal to remove endogenous steroids. Cells were plated in 24-well Falcon plastic culture plates (2 $Cm^2$/well) at the indicated density and allowed to adhere to the surface of the plates for 72 h. Thereafter, medium was replaced with fresh medium containing the indicated concentrations of compounds diluted from 1000× stock solutions in 99% redistilled ethanol in the presence or absence of $E_2$. Control cells received only the ethanolic vehicle (0.1% EtOH, v/v). Cells were incubated for the specified time intervals with medium changes at 2- or 3-day intervals. Cell number was determined by measurement of DNA content.

Calculations and Statistical Analysis

Dose-response curves as well $IC_{50}$ values were calculated using a weighted iterative nonlinear least-squares regression. All results are expressed as means±SEM.

TABLE 11

| Experiment 1 | | | |
|---|---|---|---|
| NAME | CODE NAME | Maximal stimulation of DNA by tested compounds % of 1nM $E_2$ stimulation * | Inhibition of 1nM $E_2$ stimulation of DNA by tested compounds $IC_{50}$ (nM) |
| EM-652.HCl | EM-652.HCl; EM-1538 | N.S. | 0.796 |
| TSE 424 | EM-4803 | N.S. | 3.68 |

| Experiment 2 | | | |
|---|---|---|---|
| NAME | CODE NAME | Stimulation of DNA by tested compounds % of 1nM $E_2$ stimulation * | Inhibition of 1nM $E_2$ stimulation of DNA by tested compounds $IC_{50}$ (nM) |
| EM-652.HCl | EM-652.HCl; EM-1538 | N.S. | 0.205 |
| lasofoxifene (free base) | EM-3114 | N.S. | 0.379 |

Example 7

Comparison of the Effects of EM-652.HCl (Acolbifene), Tamoxifen, Toremifene, Droloxifene, Idoxifene, GW-5638, and Raloxifene on the Growth of Human RZ-75-1 Breast Tumors in Nude Mice The objective of this example was to compare the agonistic and antagonistic effects of EM-652.HCl and six other oral antiestrogens (SERMs) on the growth of the well-characterized estrogen-sensitive ZR-75-1 breast cancer xenografts in ovariectomized nude mice.

Materials and Methods

Human ZR-75-1 Breast Cancer Cells

ZR-75-1 human breast cancer cells were obtained from the American Type Culture Collection (Rockville, Md.) and cultured in phenol red-free RPMI-1640 medium. The cells were supplemented with 2 mM L-glutamine, 1 mM sodium pyruvate, 100 IU penicillin/mL, 100 µg streptomycin/mL, and 10% (v/v) fetal bovine serum and incubated under an humidified atmosphere of 95% air/5% $CO_2$ at 37° C. Cells were passaged weekly and harvested at 85-90% confluence using 0.083% pancreatin/0.3 mM EDTA.

Animals and Tumor Inoculation

Homozygous female nu/nu Br athymic mice (28- to 42-day old) were obtained from Charles River, Inc. (Saint-Constant, Québec, Canada). The mice (5 per cage) were housed in vinyl cages equipped with air filter lids, which were kept in laminar airflow hoods and maintained under pathogen-limiting conditions. The photoperiod was 12 hours of light and 12 hours of darkness (lights on at 07:15). Cages, bedding and food (Agway Pro-Lab R-M-H Diet #4018) were autoclaved before use. Water was autoclaved and provided ad libitum. Bilateral ovariectomy was performed under isoflurane-induced anesthesia. At the time of ovariectomy, an implant of estradiol ($E_2$) was inserted subcutaneously to stimulate initial tumor growth. $E_2$ implants were prepared in 1 cm-long Silastic tubing (inside diameter: 0.062 inch; outside diameter: 0.095 inch) containing 0.5 cm of a 1:10 (w/w) mixture of estradiol and cholesterol. One week after ovariectomy, 2×10 6 ZR-75-1 (passage 93) cells were inoculated subcutaneously in 0.1 mL of RPMI-1640 medium+30% Matrigel on both flanks of each ovariectomized (OVX) mouse through a 2.5-cm-long 22-gauge needle. After four weeks, the $E_2$ implants were replaced in all animals by estrone-containing implants of the same size ($E_1$:chol, 1:25, w:w). Randomization and treatments were started one week later.

Treatments

One day prior to initiation of treatments, 255 mice bearing ZR-75-1 tumors of an average area of 24.4±0.4 $mm^2$ (range 5.7 to 50.7 $mm^2$) were randomly assigned to 17 groups (with respect to tumor size), each containing 15 mice (total of 29 or 30 tumors). The 17 groups included two control groups (OVX and OVX+Estrone), seven groups supplemented with an estrone implant and treated with an antiestrogen and eight other groups that received an antiestrogen alone. The estrone implants were then removed from the animals in the ovariectomized control group (OVX) and in groups that were to receive the antiestrogen alone. Estrone-containing implants in the nine other groups were changed thereafter every 6 weeks. EM-652.HCl, raloxifene, droloxifene, idoxifene and GW 5638 were synthesized in the medicinal chemistry division of the Oncology and Molecular Endocrinology Research Center. tamoxifen was purchased from Plantex (Netanya, Israel) while toremifene citrate was purchased from Orion (Espoo, Finland). Under estrone stimulation, the antiestrogens were given at the daily oral dose of 50 µg (2 mg/kg, on average) suspended in 0.2 mL of 0.4% (w/v) methylcellulose. In the absence of estrone stimulation, animals were treated with 200 µg (8 mg/kg on average) of each antiestrogen once daily by the oral route. Animals in both control groups received 0.2 mL of the vehicle alone. The antiestrogen suspensions at the appropriate concentration were prepared each month, stored at 4° C. and used under constant agitation. Powder stock were hermetically stored at 4° C. (idoxifene, raloxifene, toremifene, GW 5638, droloxifene) or at room temperature (tamoxifen, EM-652.HCl).

Tumor Measurements and Necropsy

Two perpendicular diameters were recorded and tumor area ($mm^2$) was calculated using the formula: L/2×W/2×π. The area measured on the first day of treatment was taken as 100%.

After 161 days of treatment, the remaining animals were anesthetized with isoflurane and killed by exsanguination. To further characterize the effect of the estrogen and antiestrogens, estrogen-responsive tissues, such as the uterus and vagina, were immediately removed, freed from connective and adipose tissue and weighed. The uteri were prepared to evaluate endometrial thickness by image analysis performed with Image Pro-Plus (Media Cybernetics, Md., USA). In brief, uteri were fixed in 10% formalin and embedded in parafin. Hematoxylin- and eosin-stained sections of mice uteri were analyzed. Four images per uterus (2 per uterine horn) were analyzed. Mean epithelial cell height was measured in all animals of each group.

Response Criteria

Tumor response was assessed at the end of the study or at death of each animal, if it occurred during the course of the experiment. In this case, only data of mice that survived for at least half of the study (84 days) were used in the tumor response analysis. In brief, complete regression identifies those tumors that were undetectable at the end of the experiment; partial regression corresponds to the tumors that regressed ≥50% of their original size; stable response refers to tumors that regressed <50% or progressed ≤50%; and progression refers to tumors that progressed ≥0.50% compared with their original size.

Statistical Analyses

The change in total tumors surface areas between Day 1 and Day 161 were analyzed according to an ANOVA for repeated measurements. The model included the treatment, time, and time-treatment interaction effects plus the term to account for the strata at randomization. The significance of the different treatments effects at 161 days was thus tested by the time-treatment interaction. Analysis of the residuals indicated that the measurements on the original scale were not fitted for analysis by an ANOVA nor any of the transformations that were tried. The ranks were therefore selected for the analyses. The effect of the treatments on the epithelial thickness was assessed by a one-way ANOVA including also the strata at randomization. A posteriori pairwise comparisons were performed using least square means statistics. The overall type 1 error rate (α) was controlled at 5% to declare significance of the differences. All calculations were performed using Proc MIXED on the SAS Software (SAS Institute, Carry, N.C.).

Results

Antagonistic Effects on ZR-75-1 Tumor Growth

Figure 19:
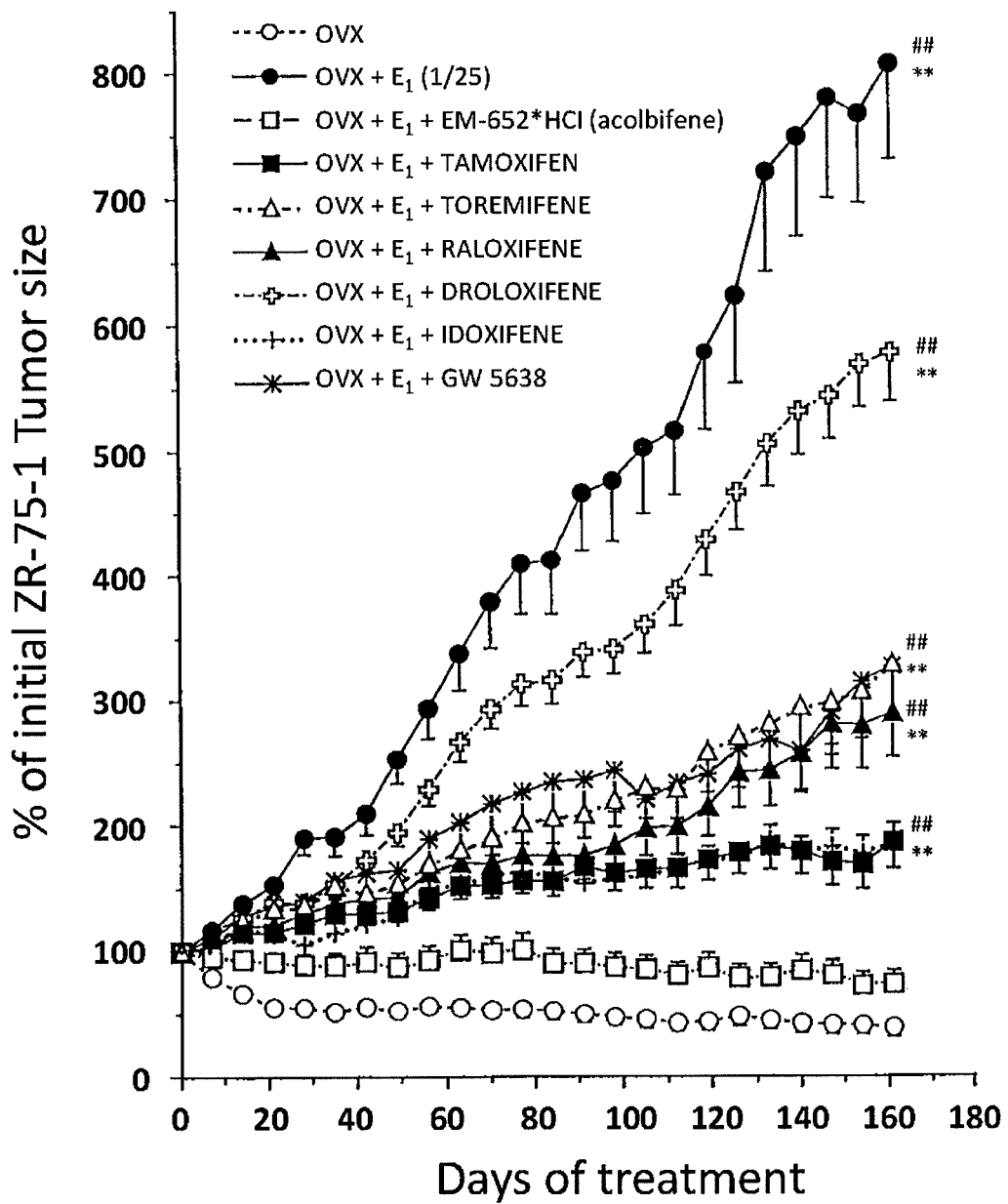
FIG. 19 shows the effects of antiestrogens on ZR-75-1 tumor growth. Effect of treatment with 7 antiestrogens for 161 days, on estrone-induced growth of human ZR-75-1 breast tumors in ovariectomized nude mice. Tumor size is expressed as the percentage of initial tumor area (Day 1=100%). Data is expressed as means±SEM (n=18-30 tumors/group); ## $p<0.01$ vs EM-652.HCl (acolbifene); **$p<0.01$ vs OVX. Antiestrogens were administered orally once daily at the dose of 50 µg/mouse under estrone stimulation obtained with subcutaneous 0.5-cm silastic implants containing 1:25 ratio of estrone and cholesterol.

Estrone alone (OVX+$E_1$) caused a 707% increase in ZR-75-1 tumor size during the 23 week-treatment period (FIG. 19). Administration of the pure antiestrogen EM-652.HCl (acolbifene) at the daily oral dose of 50 µg to estrone-stimulated mice completely prevented tumor growth. In fact, not only tumor growth was prevented but after 23 weeks of treatment, tumor size was 26% lower than the initial value at start of treatment (p<0.04). This value obtained after treatment with EM-652.HCl was not statistically different from that observed after ovariectomy alone (OVX) where tumor size decreased by 61% below initial tumor size. At the same dose (50 µg) and treatment period, the six other antiestrogens did not decrease initial average tumor size. Tumors in these groups were all significantly higher than the OVX control group and to the EM-652.HCl-treated group (p<0.01). In fact, compared to pretreatment values, 23 weeks of treatment with droloxifene, toremifene, GW 5638, raloxifene, tamoxifen and idoxifene led to average tumor sizes 478%, 230%, 227%, 191%, 87% and 86% above pretreatment values, respectively (FIG. 19).

Agonistic Effects on ZR-75-1 Tumor Growth

Figure 20:
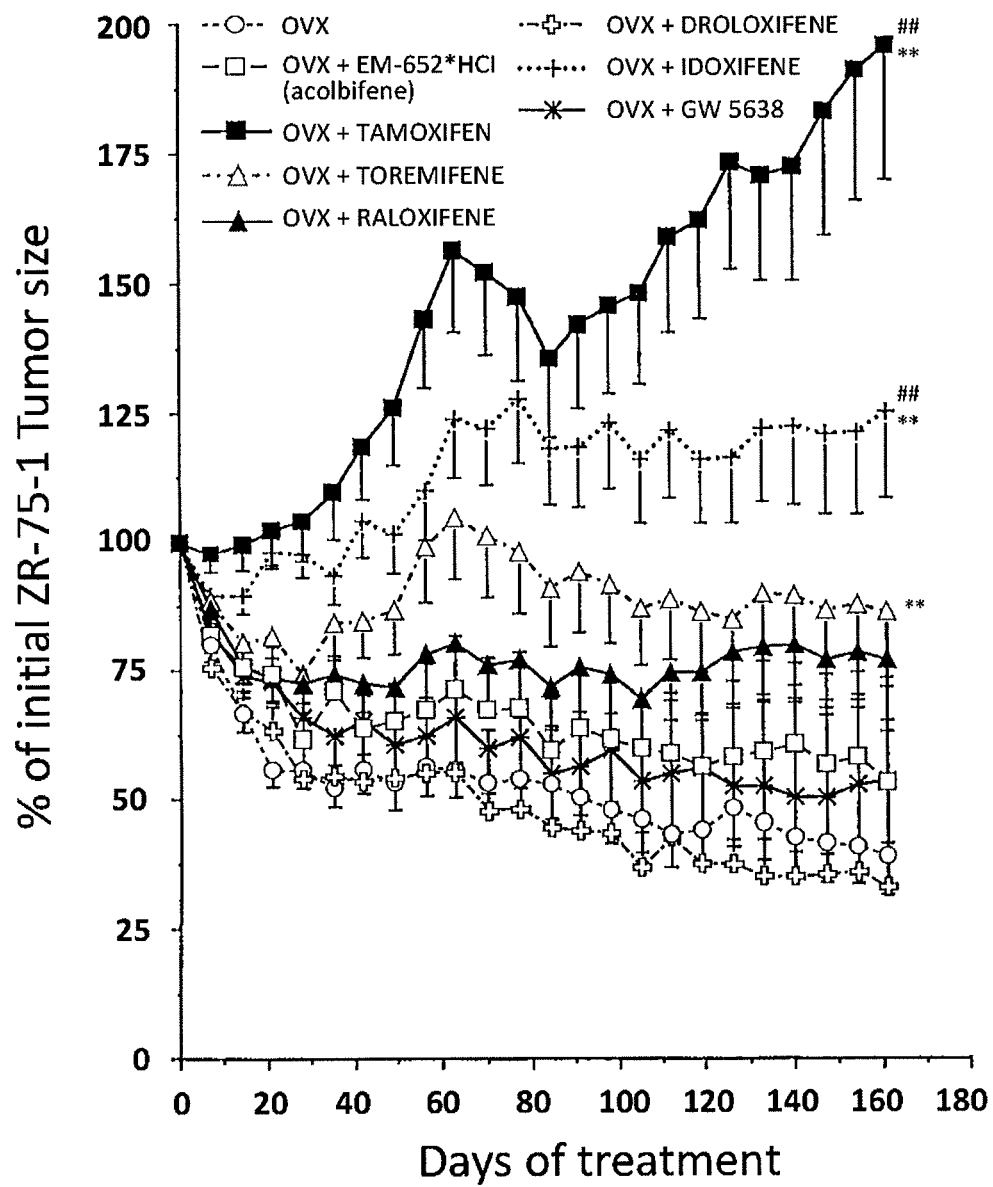
FIG. 20 shows the effects of antiestrogens on ZR-75-1 tumor growth. Effect of treatment with 7 antiestrogens for 161 days, on the growth of human ZR-75-1 breast tumors in ovariectomized nude mice. Tumor size is expressed as the percentage of initial tumor area (Day 1=100%). Date is expressed as means±SEM (n=18-30 tumors/group); ## $p<0.01$ vs EM-652.HCl (acolbifene); **$p<0.01$ vs OVX. Antiestrogens were administered orally once daily at the dose of 100 µg/mouse in absence of estrogen stimulation.
Figure 21:
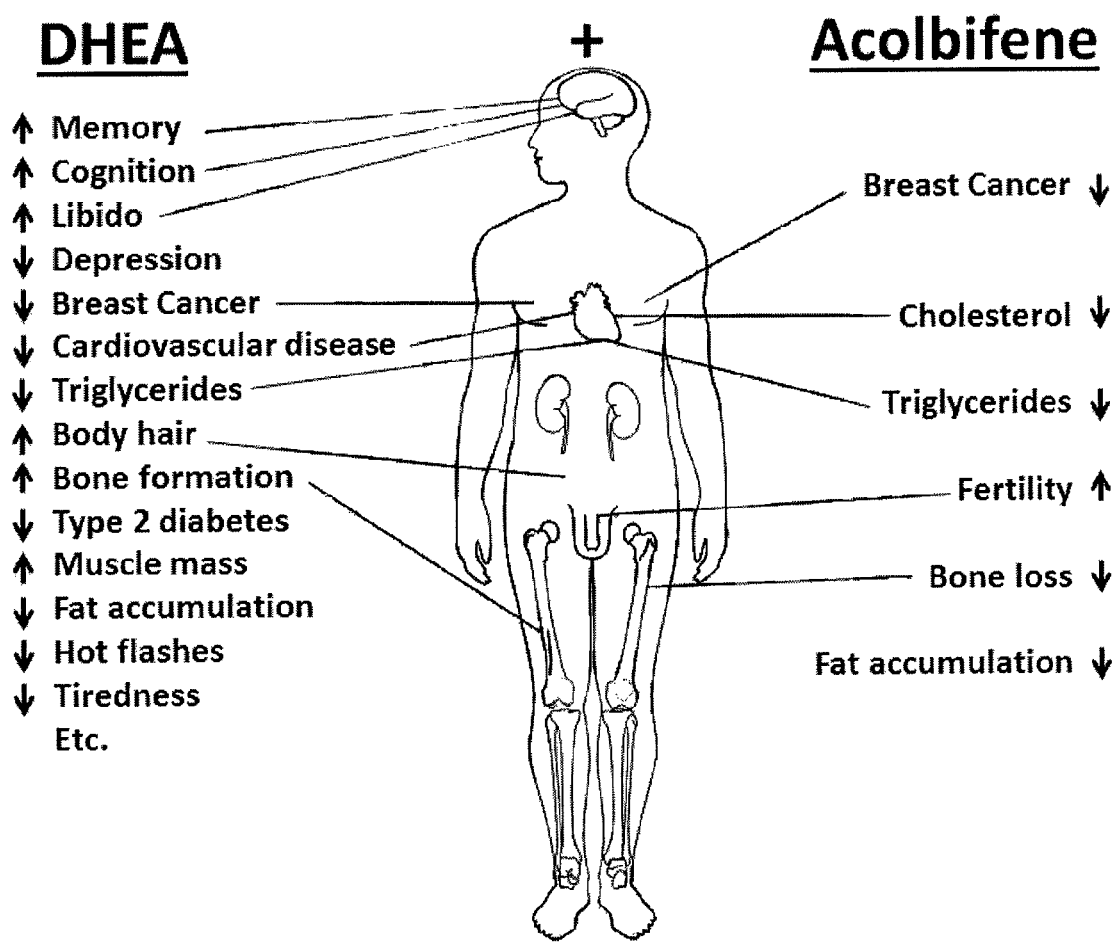
FIG. 21 shows the effects of the combination of dehydroepiandrosterone and the SERM acolbifene on various parameters. The addition of acolbifene to dehydroepiandrosterone will treat or reduce the indicated negative effects of low androgens.

After 161 days of treatment with a daily dose of 200 µg of tamoxifen, in the absence of estrone supplementation, the average tumor size increased to 196% over baseline (p<0.01 vs OVX) (FIG. 20). On the other hand, the average tumor size of mice treated with idoxifene increased (125%) (p<0.01) while tumor size in mice treated with toremifene increased by 86% (p<0.01) (FIG. 20). The addition of 200 µg of EM-652.HCl to 200 µg of tamoxifen completely inhibited the proliferation observed with tamoxifen alone (FIG. 15). On the other hand, treatment with EM-652.HCl (p=0.44), raloxifene (p=0.11), droloxifene (p=0.36) or GW 5638 (p=0.17) alone did not significantly change ZR-75-1 tumor size compared to the OVX control group, at the end of the experiment (FIG. 20).

Effects of Antiestrogens on Thickness of Uterine Epithelial Cells

The height of the endometrial epithelial cells was measured as the most direct parameter of agonistic and antagonistic effect of each compound in the endometrium.

Effect of Daily 50 µg of Antiestrogen in the Presence of Estrone Stimulation on Thickness of Uterine Epithelial Cells At the daily oral dose of 50 µg, EM-652.HCl (acolbifene) inhibited the stimulatory effect of estrone on epithelial height by 70%. The efficacy of the six other antiestrogens tested were significantly lower (p<0.01). In fact, droloxifene, GW 5638, raloxifene, tamoxifen, toremifene and idoxifene inhibited estrone stimulation by 17%, 24%, 26%, 32%, 41% and 50%, respectively (Table 12).

Effect of Daily 200 µg of Antiestrogen in Absence of Estrone Stimulation on Thickness of Uterine Epithelial Cells In the absence of estrone stimulation, EM-652.HCl and droloxifene were the only compounds tested that did not significantly increase the height of epithelial cells (114% and 101% of the OVX control group value, respectively). Tamoxifen (155%), toremifene (135%) and idoxifene (176%) exerted a significant stimulation of uterine epithelial height (p<0.01 vs OVX control group). Raloxifene (122%) and GW 5638 (121%) also exerted a statistically significant stimulation of uterine epithelial height (p<0.05 vs OVX control group (Table 12). The agonistic and antagonistic effects of each antiestrogen measured on uterine and vaginal weight were in accordance with the pattern observed on uterine epithelium thickness (Data not shown).

TABLE 12

| GROUP | n | ENDOMETRIAL EPITHELIUM THICKNESS (µm) ± SEM |
|---|---|---|
| OVX CONTROL | 14 | 18.31 ± 0.04 |
| OVX + $E_1$ + CONTROL | 8 | 40.58[b,d] ± 0.63 |

TABLE 12-continued

| GROUP | n | ENDOMETRIAL EPITHELIUM THICKNESS (µm) ± SEM |
|---|---|---|
| OVX + $E_1$ + EM-652•HCl | 14 | 25.06[b] ± 0.07 |
| OVX + $E_1$ + TAMOXIFEN | 10 | 33.44[b,d] ± 0.04 |
| OVX + $E_1$ + TOREMIFENE | 13 | 31.47[b,d] ± 0.04 |
| OVX + $E_1$ + RALOXIFENE | 12 | 34.72[b,d] ± 0.06 |
| OVX + $E_1$ + DROLOXIFENE | 12 | 36.71[b,d] ± 0.12 |
| OVX + $E_1$ + IDOXIFENE | 12 | 29.35[b,d] ± 0.05 |
| OVX + $E_1$ + GW 5638 | 12 | 35.30[b,d] ± 0.07 |
| OVX + EM-652•HCl | 12 | 20.79 ± 0.10 |
| OVX + TAMOXIFEN | 11 | 28.47[b,d] ± 0.05 |
| OVX + EM-652•HCl + TAMOXIFEN | 13 | 27.95[b,d] ± 0.06[a] |
| OVX + TOREMIFENE | 13 | 24.75[b,c] ± 0.04 |
| OVX + RALOXIFENE | 12 | 22.33[a] ± 0.05 |
| OVX + DROLOXIFENE | 13 | 18.50 ± 0.07 |
| OVX + IDOXIFENE | 11 | 32.14[b,d] ± 0.05 |
| OVX + GW 5638 | 13 | 22.22[a] ± 0.05 |

[a,b]Experimental versus OVX control mice: [a]P < 0.05; [b]P < 0.01.
[c,d]Experimental versus EM-652•HCl treated-mice: [c]P < 0.05; [d]P < 0.01.

Example 8

Radioactivity in the Brain of Female Rats Following a Single Oral Dose of $^{14}$C-EM-800 (20 Mg/Kg)

Example 8 shows the radioactivity in brain of rats following single oral dose of $^{14}$C-EM-800 (20 mg/kg), a SERM of the present invention. For comparison purposes, values for the blood, plasma, liver and uterus from each of these animals were included (Table 14). Tissue Distribution and Excretion of Radioactivity Following a Single Oral Dose of $^{14}$C-EM-800 (20 ring/2 mL/kg) to Male and Female Long-Evans Rats. These numbers indicate that the amount of total drug-derived radioactivity in the brain of female Long-Evans rats was very low (ng equiv/g tissue) and was not detected after 12 hr post dose. At 2 hours, radioactivity in the brain was 412 lower than in liver, 21 times lower than in the uterus, 8.4 times lower that in the blood and 13 times lower than in plasma. Since an unknown proportion of total brain radioactivity is due to contamination by blood radioactivity, the values shown in Table 13 for brain radioactivity are an overestimate of the level of $^{14}$C (EM-800)—related radioactivity in the brain tissue itself. Such data suggest that the level of the antiestrogen in the brain tissue is too low, to counteract the effect of exogenous estrogen. It is important to note that some of the radioactivity detected in the brain tissue may be due to residual blood in the tissue (Table 14). Additionally, the radiochemical purity of the $^{14}$C-EM-800 used for this study was minimally 96.25%.

TABLE 13

Mean Concentration of Drug-Derived Radioactivity (ng EM-800 equiv/g tissue) in Selected Tissues of Female Long-Evans Rats Following a Single Oral Dose of $^{14}$C-EM-800 (20 mg/kg)[a]

| Time (hr) | Brain Mean[b] (% CV) | Blood Mean[b] (% CV) | Plasma Mean[b] (% CV) |
|---|---|---|---|
| 2 | 17.6 (29) | 148.7 (22) | 224.6 (20) |
| 4 | 17.1 (29) | 66.9 (45) | 103.2 (39) |
| 6 | 15.6 (8) | 48.3 (29) | 74.1 (31) |
| 8 | 16.8 (31) | 41.1 (12) | 64.1 (14) |
| 12 | 10.0[c] (87) | 28.7 (54) | 40.7 (55) |
| 24 | 0 (NC) | 4.7[d] (173) | 10.1 (86) |
| 36 | 0 (NC) | 0 (NC) | 0 (NC) |
| 48 | 0 (NC) | 0 (NC) | 0 (NC) |

TABLE 13-continued

Mean Concentration of Drug-Derived Radioactivity (ng EM-800 equiv/g tissue) in Selected Tissues of Female Long-Evans Rats Following a Single Oral Dose of $^{14}$C-EM-800 (20 mg/kg)$^a$

| Time (hr) | Brain Mean$^b$ (% CV) | Blood Mean$^b$ (% CV) | Plasma Mean$^b$ (% CV) |
|---|---|---|---|
| 72 | 0 (NC) | 0 (NC) | 0 (NC) |
| 96 | 0 (NC) | 0 (NC) | 0 (NC) |
| 168 | 0 (NC) | 0 (NC) | 0 (NC) |

$^a$Values from report tables for LREM 1129 (EM-800: Tissue Distribution and Excretion of Radioactivity Following a Single Oral Dose of $^{14}$C-EM-800 (20 mg/2 mL/kg) to Male and Female Long-Evans Rats).
$^b$Limit of quantification (LOQ) of 1.2 ng EM-800 equivalent.
$^c$One sample below the LOQ; 0 used in calculation of mean.
$^d$Two samples below the LOQ; 0 used in calculation of mean.
% CV: Coefficient of variation expressed as a percent, where n = 3.
NC: Not calculated.

TABLE 14

Mean Concentration of Drug-Derived Radioactivity (μg EM-800 equiv/g tissue) in Selected Tissues of Female Long-Evans Rats Following a Single Oral Dose of $^{14}$C-EM-800 (20 mg/kg)$^a$

| Time (hr) | Brain Mean$^b$ (% CV) | Liver Mean$^b$ (% CV) | Uterus Mean$^b$ (% CV) | Blood Mean$^b$ (% CV) | Plasma Mean$^b$ (% CV) |
|---|---|---|---|---|---|
| 2 | 0.0176 (29) | 7.2547 (30) | 0.3675 (36) | 0.1487 (22) | 0.2246 (20) |
| 4 | 0.0171 (29) | 3.2201 (48) | 0.2866 (83) | 0.0669 (45) | 0.1032 (39) |
| 6 | 0.0156 (8) | 2.7462 (8) | 0.2757 (19) | 0.0483 (29) | 0.0741 (31) |
| 8 | 0.0168 (31) | 2.7748 (8) | 0.3332 (46) | 0.0411 (12) | 0.0641 (14) |
| 12 | 0.0100$^c$ (87) | 1.8232 (38) | 0.2407 (25) | 0.0287 (54) | 0.0407 (55) |
| 24 | 0 (NC) | 0.6391 (52) | 0.0837 (54) | 0.0047$^d$ (173) | 0.0101 (86) |
| 36 | 0 (NC) | 0.4034 (22) | 0.0261 (15) | 0 (NC) | 0 (NC) |
| 48 | 0 (NC) | 0.2196 (37) | 0.0238 (44) | 0 (NC) | 0 (NC) |
| 72 | 0 (NC) | 0.1326 (4) | 0 (NC) | 0 (NC) | 0 (NC) |
| 96 | 0 (NC) | 0.0944 (15) | 0 (NC) | 0 (NC) | 0 (NC) |
| 168 | 0 (NC) | 0.0348 (14) | 0 (NC) | 0 (NC) | 0 (NC) |

$^a$Values from report tables for LREM 1129 (EM-800: Tissue Distribution and Excretion of Radioactivity Following a Single Oral Dose of $^{14}$C-EM-800 (20 mg/2 mL/kg) to Male and Female Long-Evans Rats).
$^b$Limit of quantification (LOQ) of 1.2 ng EM-800 equivalent.
$^c$One sample below the LOQ; 0 used in calculation of mean.
$^d$Two samples below the LOQ; 0 used in calculation of mean.
% CV: Coefficient of variation expressed as a percent, where n = 3.
NC: Not calculated.

Example 9

Animals

Female BALB/c mice (BALB/cAnNCrlBR), approximately 50 days old and weighing 18-20 g, were obtained from Charles-River, Inc. (St-Constant, Quebec, Canada) and housed 4-5/cage in a temperature (23±1° C.)- and light (12 h light/day, lights on at 7:15)-controlled environment. The mice were fed rodent chow and tap water ad libitum. The animals were ovariectomized (OVX) under general anesthesia (Avertin) via bilateral flank incisions and randomly assigned to groups of 9-10 animals.

Treatments

CS-115-1 (racemic EM-652) and EM-762 (racemic EM-800) were administered orally by gavage or by topical application on the dorsal skin once daily at different doses, namely 0.75, 2.5, 7.5, 25 or 75 nmol of compound/gavage or application/animal. Treatment with the antiestrogens (0.2 mL/mouse/gavage or application) was initiated 2 days after ovariectomy, while treatment with estrone (0.06 μg, subcutaneous injection (s.c.), twice daily) was started 3 days later (5 days post-ovariectomy). Thereafter, estrone and antiestrogens were administered in combination for a 6 day-period. For oral administration, compounds were dissolved in a 50:50 (vol/vol) mixture of polyethylene glycol 600 (PEG-600) and ethanol and administered in a 1% (w/v) gelatin-0.9% NaCl solution (final concentration of PEG-600:ETOH was 8%) while for the percutaneous administration, compounds were solubilized in 50% ETOH-50% propylene glycol. Mice in the OVX control group received the oral vehicle alone during the 9-day period. The animals were killed by cervical dislocation on the 11$^{th}$ morning following ovariectomy. Uteri were rapidly dissected and weighed.

As can be seen on FIG. 16, comparable effects are observed after administration of acolbifene derivatives by the oral and percutaneous routes.

PHARMACEUTICAL COMPOSITION EXAMPLES

Set forth below, by way of example and not of limitation, are several pharmaceutical compositions utilizing preferred active SERM acolbifene (EM-652.HCl; EM-1538) and preferred active sex steroid precursor dehydroepiandrosterone (DHEA, Prasterone). Other compounds of the invention or combination thereof, may be used in place of (or in addition to) acolbifene or dehydroepiandrosterone. The concentration of active ingredient may be varied over a wide range as discussed herein. The amounts and types of other ingredients that may be included are well known in the art.

Example A

Pharmaceutical Composition for Orally Administration (Capsules)

| Ingredient | Weight % (by weight of total composition) |
|---|---|
| Acolbifene | 5.0 |
| DHEA | 10.0 |
| Lactose hydrous | 70.0 |
| Starch | 4.8 |
| Cellulose microcrystalline | 9.8 |
| Magnesium stearate | 0.4 |

Example B

Pharmaceutical Composition for Orally Administration (Tablets)

| Ingredient | Weight % (by weight of total composition) |
| --- | --- |
| Acolbifene | 5.0 |
| DHEA | 15.0 |
| Gelatin | 5.0 |
| Lactose | 58.5 |
| Starch | 16.5 |

Example C

Topical Administration (Cream)

| Ingredient | Weight % (by weight of total composition) |
| --- | --- |
| DHEA | 1.0 |
| Acolbifene | 0.2 |
| Emulsifying Wax, NF | 18.0 |
| Light mineral oil, NF | 12.0 |
| Benzyl alcohol | 1.0 |
| Ethanol 95% USP | 33.8 |
| Purifed water, USP | 34.0 |

Example D

Rectal Administration

Rectal Suppository or Ovule

| Ingredient | Weight % (by weight of total composition) |
| --- | --- |
| DHEA | 0.25 to 2.0 |
| Acolbifene | 0.25 to 3.0 |
| Witepsol H-15 base | 95.0 to 99.5 |

DHEA suppositories were prepared using Witepsol H-15 base (Medisca, Montreal, Canada). Any other lipophilic base such as Hard Fat, Fattibase, Wecobee, cocoa butter, *theobroma* oil or other combinations of Witepsol bases could used. Preferred SERMs are EM-800 and acolbifene

Kit Examples

Set forth below, by way of example and not of limitation, are several kits utilizing preferred active SERM acolbifene, preferred antiestrogen Faslodex and preferred active a sex steroid precursor DHEA. The concentration of active ingredient may be varied over a wide range as discussed herein. The amounts and types of other ingredients that may be included are well known in the art.

Example D

Kit

The SERM and Sex Steroid Precursor are Orally Administered

SERM Composition for Oral Administration (Capsules)

| Ingredient | Weight % (by weight of total composition) |
| --- | --- |
| Acolbifene | 5.0 |
| Lactose hydrous | 80.0 |
| Starch | 4.8 |
| Cellulose microcrystalline | 9.8 |
| Magnesium stearate | 0.4 |

+

DHEA Composition for Oral Administration (Gelatin Capsule)

| Ingredient | Weight % (by weight of total composition) |
| --- | --- |
| DHEA | 25.0 |
| Lactose hydrous | 27.2 |
| Sodium Starch Glycolate | 20.0 |
| Microcrystalline Cellulose, Colloidal Silicon Dioxide, Silica Colloidal Anhydrous and Light Anhydrous Silicic Acid | 27.2 |
| Colloidal Silicon Dioxide | 0.1 |
| Magnesium stearate | 0.5 |

Other SERMs may be substituted for acolbifene in the above formulations, as well as other sex steroid precursors may be substituted for DHEA. More than one SERM or more than one sex steroid precursor may be included in which case the combined weight percentage is preferably that of the weight percentage for the single sex steroid precursor or single SERM given in the examples above.

Example E

Kit

The SERM is Orally Administered and the Sex Steroid Precursor is Rectally Administered

SERM Composition for Oral Administration (Capsules)

| Ingredient | Weight % (by weight of total composition) |
| --- | --- |
| Acolbifene | 5.0 |
| Lactose hydrous | 80.0 |
| Starch | 4.8 |
| Cellulose microcrystalline | 9.8 |
| Magnesium stearate | 0.4 |

Rectal Suppository

| Ingredient | Weight % (by weight of total composition) |
|---|---|
| DHEA | 0.25 to 2.0 |
| Witepsol H-15 base | 98 to 99.75 |

DHEA suppositories were prepared using Witepsol H-15 base (Medisca, Montreal, Canada). Any other lipophilic base such as Hard Fat, Fattibase, Wecobee, cocoa butter, *theobroma* oil or other combinations of Witepsol bases could used.

Example F

Kit

The SERM and the Sex Steroid Precursor are Rectally Administered Rectal Suppository

| Ingredient | Weight % (by weight of total composition) |
|---|---|
| DHEA | 0.25 to 2.0 |
| Witepsol H-15 base | 98 to 99.75 |

+

Rectal Suppository

| Ingredient | Weight % (by weight of total composition) |
|---|---|
| Acolbifene | 0.3 to 3.0 |
| Hard Fat | 97.0 to 99.7 |

Acolbifene suppositories were prepared using Hard Fat (Witepsol). Any other bases such as Fattibase, Wecobee, cocoa butter, *theobroma* oil or other combinations of Hard Fat could be used.

Example G

The SERM is Orally Administered and the Sex Steroid Precursor is Percutaneously Administered

SERM Composition for Oral Administration (Capsules)

| Ingredient | Weight % (by weight of total composition) |
|---|---|
| Acolbifene | 5.0 |
| Lactose hydrous | 80.0 |
| Starch | 4.8 |
| Cellulose microcrystalline | 9.8 |
| Magnesium stearate | 0.4 |

+

Sex Steroid Precursor Composition for Transdermal Administration (Gel)

| Ingredient | Weight % (by weight of total composition) |
|---|---|
| DHEA | 2.0 |
| Caprylic-capric Triglyceride (Neobee M-5) | 5.0 |
| Hexylene Glycol | 15.0 |
| Transcutol (diethyleneglycol monomethyl ether) | 5.0 |
| Benzyl alcohol | 2.0 |
| Cyclomethicone (Dow corning 345) | 5.0 |
| Ethanol (absolute) | 64.0 |
| Hydroxypropylcellulose (1500 cps) (KLUCEL) | 2.0 | or

Sex Steroid Precursor Composition for Transdermal Administration (Cream)

| Ingredient | Weight % (by weight of total composition) Formulation EM-760-48-1.0% |
|---|---|
| Cyclometicone | 5.0% |
| Light mineral oil | 3.0% |
| 2-ethylhexyl stearate | 10.0% |
| Cutina E24 | 1.0% |
| DC emulsifier 10 | 3.0% |
| BHT | 0.09% |
| Propyleneglycol | 46.01% |
| Ethanol 95 | 10.0% |
| DHEA | 1.0% |
| Eau purifiee | 15.0% |
| MgSO4 | 0.65% |
| Ethanol 95 | 5.25% |
| Total | 100.0% |

Example H

Kit

The Antiestrogen is Intramuscularly Administered and Sex Steroid Precursor is Orally Administered Commercially Available Steroidal Antiestrogen
Faslodex

+

DHEA Composition for Oral Administration
(Gelatin Capsule)

| Ingredient | Weight % (by weight of total composition) |
|---|---|
| DHEA | 25.0 |
| Lactose hydrous | 27.2 |
| Sodium Starch Glycolate | 20.0 |
| Microcrystalline Cellulose, Colloidal Silicon Dioxide, Silica Colloidal Anhydrous and Light Anhydrous Silicic Acid | 27.2 |
| Colloidal Silicon Dioxide | 0.1 |
| Magnesium stearate | 0.5 |

Other SERMs (toremifene, ospemifene, raloxifene, arzoxifene, lasofoxifene, TSE-424, ERA-923, EM-800, SERM 3339, GW-5638) may be substituted for acolbifene in the above formulations, as well as other sex steroid precursors may be substituted for DHEA. More than one SERM or more than one precursor may be included in which case the combined weight percentage is preferably that of the weight percentage for the single precursor or single SERM given in the examples above.

The invention has been described in terms of preferred embodiments and examples, but is not limited thereby. Those of skill in the art will readily recognize the broader applicability and scope of the invention which is limited only by the patent claims herein.

Recommandations

We suggest men having a palpable prostatic nodule or induration or with a serum PSA above 3 ng/mL to have further urological evaluation before treatment as suggested by the Guidelines of the Endocrine Society (Bhasin, Cunningham et al. 2006).

Similarly, treatment is not recommended in men with erythrocytosis (hematocrit>50%), untreated obstructive sleep apnea, severe untreated benign prostatic hyperplasia with IPSS score>19 or uncontrolled heart failure.

REFERENCES

Akaza, H. (2006). "Trends in primary androgen depletion therapy for patients with localized and locally advanced prostate cancer: Japanese perspective." *Cancer Sci* 97(4): 243-247.

Alexandersen, P., J. Haarbo, et al. (1996). "The relationship of natural androgens to coronary heart disease in males: a review." *Atherosclerosis* 125(1): 1-13.

Almeida, O. P., B. B. Yeap, et al. (2008). "Low free testosterone concentration as a potentially treatable cause of depressive symptoms in older men." *Arch Gen Psychiatry* 65(3): 283-289.

Amano, T., T. Imao, et al. (2010). "Testosterone replacement therapy by testosterone ointment relieves lower urinary tract symptoms in late onset hypogonadism patients." *Aging Male* 13(4): 242-246.

American Society of Andrology (2006). "Testosterone replacement therapy for male aging: ASA position statement." *J Androl* 27(2): 133-134.

Anker, S. D., T. P. Chua, et al. (1997). "Hormonal changes and catabolic/anabolic imbalance in chronic heart failure and their importance for cardiac cachexia." *Circulation* 96(2): 526-534.

Anker, S. D., A. L. Clark, et al. (1997). "Tumor necrosis factor and steroid metabolism in chronic heart failure: possible relation to muscle wasting." *J Am Coll Cardiol* 30(4): 997-1001.

Araujo, A. B. and G. A. Wittert (2011). "Endocrinology of the aging male." *Best Pract Res Clin Endocrinol Metab* 25(2): 303-319.

Arlt, W., F. Callies, et al. (1999). "Dehydroepiandrosterone replacement in women with adrenal insufficiency." *N. Engl. J. Med.* 341(14): 1013-1020.

Arlt, W., H. G. Justl, et al. (1998). "Oral dehydroepiandrosterone for adrenal androgen replacement: pharmacokinetics and peripheral conversion to androgens and estrogens in young healthy females after dexamethasone suppression." *J. Clin. Endocrinol. Metab.* 83(6): 1928-1934.

Azad, N., S. Pitale, et al. (2003). "Testosterone treatment enhances regional brain perfusion in hypogonadal men." *J Clin Endocrinol Metab* 88(7): 3064-3068.

Bachmann, G., J. Bancroft, et al. (2002). "Female androgen insufficiency: the Princeton consensus statement on definition, classification, and assessment." *Fertil Steril* 77(4): 660-665.

Baillargeon, J., R. J. Urban, et al. (2013). "Trends in androgen prescribing in the United States, 2001 to 2011." *JAMA Intern Med* 173(15): 1465-1466.

Barnhart, K. T., E. Freeman, at al. (1999). "The effect of dehydroepiandrosterone supplementation to symptomatic perimenopausal women on serum endocrine profiles, lipid parameters, and health-related quality of life." *J Clin Endocrinol Metab* 84(11): 3896-3902.

Barrett-Connor, E. and S. L. Edelstein (1994). "A prospective study of dehydroepiandrosterone sulfate and cognitive function in an older population: the Rancho Bernardo Study." *J Am Geriatr Soc* 42(4): 420-423.

Barrett-Connor, E., K. T. Khaw, et al. (1986). "A prospective study of dehydroepiandrosterone sulfate, mortality and cardiovascular disease." *N. Engl. J. Med.* 315(24): 1519-1524.

Basaria, S., A. D. Coviello, et al. (2010). "Adverse events associated with testosterone administration." *N Engl J Med* 363(2): 109-122.

Basaria, S., M. N. Davda, et al. (2013). "Risk factors associated with cardiovascular events during testosterone administration in older men with mobility limitation." *J Gerontol A Biol Sci Med Sci* 68(2): 153-160.

Bassil, N., S. Alkaade, et al. (2009). "The benefits and risks of testosterone replacement therapy: a review." *Ther Clin Risk Manag* 5(3): 427-448.

Basson, R. (2004). "A New Model of Female Sexual Desire." *Endocrine News* 29: 22.

Beck, S. G. and R. J. Handa (2004). "Dehydroepiandrosterone (DHEA): a misunderstood adrenal hormone and spine-tingling neurosteroid?" *Endocrinology* 145(3): 1039-1041.

Beer, N. A., D. J. Jakubowicz, et al. (1996). "Dehydroepiandrosterone reduces plasma plasminogen activator inhibitor type 1 and tissue plasminogen activator antigen in men." *Am J Med Sci* 311(5): 205-210.

Behre, H. M., J. Bohmeyer, et al. (1994). "Prostate volume in testosterone-treated and untreated hypogonadal men in comparison to age-matched normal controls." *Clin Endocrinol (Oxf)* 40(3): 341-349.

Bélanger, A., M. Brochu, et al. (1986). "Levels of plasma steroid glucuronides in intact and castrated men with prostatic cancer." *J. Clin. Endocrinol. Metab.* 62: 812-815.

Bélanger, B., A. Bélanger, et al. (1989). "Comparison of residual C-19 steroids in plasma and prostatic tissue of human, rat and guinea pig after castration: unique importance of extratesticular androgens in men." *J. Steroid Biochem.* 32: 695-698.

Benz, D. J., M. R. Haussler, et al. (1991). "High-affinity androgen binding and androgenic regulation of a1(I)-procollagen and transforming growth factor-b steady state messenger ribonucleic acid levels in human osteoblast-like osteosarcoma cells." *Endocrinology* 128: 2723-2730.

Bhasin, S., G. R. Cunningham, et al. (2006). "Testosterone therapy in adult men with androgen deficiency syndromes: an endocrine society clinical practice guideline." *J Clin Endocrinol Metab* 91(6): 1995-2010.

Bhasin, S., G. R. Cunningham, et al. (2010). "Testosterone therapy in men with androgen deficiency syndromes: an Endocrine Society clinical practice guideline." *J Clin Endocrinol Metab* 95(6): 2536-2559.

Bhasin, S., T. W. Storer, et al. (1996). "The effects of supraphysiologic doses of testosterone on muscle size and strength in normal men." *N Engl J Med* 335(1): 1-7.

Bhasin, S., T. W. Storer, et al. (1997). "Testosterone replacement increases fat-free mass and muscle size in hypogonadal men." *J Clin Endocrinol Metab* 82(2): 407-413.

Bhasin, S., L. Woodhouse, et al. (2001). "Testosterone dose-response relationships in healthy young men." *Am J Physiol Endocrinol Metab* 281(6): E1172-1181.

Bhasin, S., L. Woodhouse, et al. (2005). "Older men are as responsive as young men to the anabolic effects of graded doses of testosterone on the skeletal muscle." *J Clin Endocrinol Metab* 90(2): 678-688.

Bolona, E. R., M. V. Uraga, et al. (2007). "Testosterone use in men with sexual dysfunction: a systematic review and meta-analysis of randomized placebo-controlled trials." *Mayo Clin Proc* 82(1): 20-28.

Bonnefoy, M., M. C. Patricot, et al. (2002). "[Relation between physical activity, muscle function and IGF-1, testosterone and DHEAS concentrations in the elderly]." *Rev Med Interne* 23(10): 819-827.

Bross, R., R. Casaburi, et al. (1998). "Androgen effects on body composition and muscle function: implications for the use of androgens as anabolic agents in sarcopenic states." *Baillieres Clin Endocrinol Metab* 12(3): 365-378.

Burger, H. G., J. Hailes, et al. (1984). "The management of persistent menopausal symptoms with oestradiol-testosterone implants: clinical, lipid and hormonal results." *Maturitas* 6: 351-358.

Callies, F., M. Fassnacht, et al. (2001). "Dehydroepiandrosterone replacement in women with adrenal insufficiency: effects on body composition, serum leptin, bone turnover, and exercise capacity." *J Clin Endocrinol Metab* 86(5): 1968-1972.

Calof, O. M., A. B. Singh, et al. (2005). "Adverse events associated with testosterone replacement in middle-aged and older men: a meta-analysis of randomized, placebo-controlled trials." *J Gerontol A Biol Sci Med Sci* 60(11): 1451-1457.

Cappola, A. R. (2013). "Testosterone therapy and risk of cardiovascular disease in men." *Jama* 310(17): 1805-1806.

Casson, P. R., R. N. Andersen, et al. (1993). "Oral dehydroepiandrosterone in physiologic doses modulates immune function in postmenopausal women." *Am. J. Obstet. Gynecol.* 169: 1536-1539.

Casson, P. R., N. Santoro, et al. (1998). "Postmenopausal dehydroepiandrosterone administration increases free insulin-like growth factor-I and decreases high-density lipoprotein: a six-month trial." *Fertil Steril* 70(1): 107-110.

Caubet, J. F., T. D. Tosteson, et al. (1997). "Maximum androgen blockade in advanced prostate cancer: a meta-analysis of published randomized controlled trials using nonsteroidal antiandrogens." *Urology* 49: 71-78.

Cefalu, W. T., Z. Q. Wang, et al. (1995). "Contribution of visceral fat mass to the insulin resistance of aging." *Metabolism* 44(7): 954-959.

Chang, D. M., J. L. Lan, et al. (2002). "Dehydroepiandrosterone treatment of women with mild-to-moderate systemic lupus erythematosus: a multicenter randomized, double-blind, placebo-controlled trial." *Arthritis Rheum* 46(11): 2924-2927.

Chang, J. T., S. C. Morton, et al. (2004). "Interventions for the prevention of falls in older adults: systematic review and meta-analysis of randomised clinical trials." *Bmj* 328(7441): 680.

Chen, S., J. Nilsen, at al. (2006). "Dose and temporal pattern of estrogen exposure determines neuroprotective outcome in hippocampal neurons: therapeutic implications." *Endocrinology* 147(11): 5303-5313.

Christopher-Hennings, J., I. D. Kurzman, et al. (1995). "The effect of high fat diet and dehydroepiandrosterone (DHEA) administration in the rhesus monkey." *In Vivo* 9(5): 415-420.

Cleary, M. P. and J. Zisk (1986). "Antiobesity effect of two different levels of dehydroepiandrosterone in lean and obese middle-aged female Zucker rats." *Int. J. Obes.* 10: 193-204.

Coleman, D. L., E. H. Leiter, et al. (1982). "Therapeutic effects of dehydroepiandrosterone (DHEA) in diabetic mice." *Diabetes* 31: 830-833.

Comhaire, F. H. (2000). "Andropause: hormone replacement therapy in the ageing male." *Eur Urol* 38(6): 655-662.

Corona, G., E. A. Jannini, et al. (2006). "Inventories for male and female sexual dysfunctions." *Int J Impot Res* 18(3): 236-250.

Corona, G., E. Mannucci, et al. (2006). "ANDROTEST: a structured interview for the screening of hypogonadism in patients with sexual dysfunction." *J Sex Med* 3(4): 706-715.

Corona, G., G. Rastrelli, et al. (2013). "Dehydroepiandrosterone supplementation in elderly men: a meta-analysis study of placebo-controlled trials." *J Clin Endocrinol Metab* 98(9): 3615-3626.

Corona, G., G. Rastrelli, et al. (2012). "Emerging medication for the treatment of male hypogonadism." *Expert Opin Emerg Drugs* 17(2): 239-259.

Couillard, S., C. Labrie, et al. (1998). "Effect of dehydroepiandrosterone and the antiestrogen EM-800 on the growth of human ZR-75-1 breast cancer xenografts." *J. Natl. Cancer Inst.* 90: 772-778.

Crawford, B. A., P. Y. Liu, et al. (2003). "Randomized placebo-controlled trial of androgen effects on muscle and bone in men requiring long-term systemic glucocorticoid treatment." *J Clin Endocrinol Metab* 88(7): 3167-3176.

Cummings, S. R. and M. C. Nevitt (1989). "A hypothesis: the causes of hip fractures." *J Gerontol* 44(4): M107-111.

Cusan, L., A. Dupont, et al. (1994). "Comparison of flutamide and spironolactone in the treatment of hirsutism: a randomized controlled trial." *Fertil. Steril.* 61: 281-287.

Davis, S. R., P. McCloud, et al. (1995). "Testosterone enhances estradiol's effects on postmenopausal density and sexuality." *Maturitas* 21: 227-236.

Dennerstein, L., E. C. Dudley, et al. (1997). "Sexuality, hormones and the menopausal transition." *Maturitas* 26(2): 83-93.

Dhatariya, K., M. L. Bigelow, et al. (2005). "Effect of dehydroepiandrosterone replacement on insulin sensitivity and lipids in hypoadrenal women." *Diabetes* 54(3): 765-769.

Diamond, P., L. Cusan, et al. (1996). "Metabolic effects of 12-month percutaneous DHEA replacement therapy in postmenopausal women." *J. Endocrinol.* 150: S43-S50.

Ding, E. L., Y. Song, et al. (2006). "Sex differences of endogenous sex hormones and risk of type 2 diabetes: a systematic review and meta-analysis." *Jama* 295(11): 1288-1299.

Ebert, T., F. Jockenhovel, et al. (2005). "The current status of therapy for symptomatic late-onset hypogonadism with transdermal testosterone gel." *Eur Urol* 47(2): 137-146.

Eich, D. M., J. E. Nestler, et al. (1993). "Inhibition of accelerated coronary atherosclerosis with dehydroepiandrosterone in the heterotopic rabbit model of cardiac transplantation." *Circulation* 87(1): 261-269.

Elashoff, J. D., A. D. Jacknow, et al. (1991). "Effects of anabolic-androgenic steroids on muscular strength." *Ann Intern Med* 115(5): 387-393.

English, K. M., R. P. Steeds, et al. (2000). "Low-dose transdermal testosterone therapy improves angina threshold in men with chronic stable angina: A randomized, double-blind, placebo-controlled study." *Circulation* 102 (16): 1906-1911.

Evans, W. (1997). "Functional and metabolic consequences of sarcopenia." *J Nutr* 127(5 Suppl): 998S-1003S.

Farhat, R., F. Al-zidjali, et al. (2010). "Outcome of gonadotropin therapy for male infertility due to hypogonadotrophic hypogonadism." *Pituitary* 13(2): 105-110.

Fernandez-Balsells, M. M., M. H. Murad, et al. (2010). "Clinical review 1: Adverse effects of testosterone therapy in adult men: a systematic review and meta-analysis." *J Clin Endocrinol Metab* 95(6): 2560-2575.

Ferrannini, E., A. Natali, et al. (1997). "Insulin resistance, hyperinsulinemia, and blood pressure: role of age and obesity. European Group for the Study of Insulin Resistance (EGIR)." *Hypertension* 30(5): 1144-1149.

Flood, J. F. and E. Roberts (1988). "Dehydroepiandrosterone sulfate improves memory in aging mice." *Brain Res* 448(1): 178-181.

Foy, M. R. (2001). "17beta-estradiol: effect on CA1 hippocampal synaptic plasticity." *Neurobiol Learn Mem* 76(3): 239-252.

Franchi F, Luisi M, at al. (1978). "Long-term study of oral testosterone undecanoate in hypogonadal males." *Int J Androl.* 1: 270-278.

Frontera, W. R., V. A. Hughes, et al. (2000). "Aging of skeletal muscle: a 12-yr longitudinal study." *J Appl Physiol* 88(4): 1321-1326.

Gallagher, A., T. J. Chambers, et al. (1993). "The estrogen antagonist ICI 182780 reduces cancellous bone volume in female rats." *Endocrinology* 133: 2787-2791.

Gauthier, S., B. Caron, et al. (1997). "(S)-(+)-4-[7-(2,2-dimethyl-1-oxopropoxy)-4-methyl-2-[4-[2-(1-piperidinyl)-ethoxy]phenyl]-2H-1-benzopyran-3-yl]-phenyl 2,2-dimethylpropanoate (EM-800): a highly potent, specific, and orally active nonsteroidal antiestrogen." *J. Med. Chem.* 40: 2117-2122.

Gebre-Medhin, G., E. S. Husebye, et al. (2000). "Oral dehydroepiandrosterone (DHEA) replacement therapy in women with Addison's disease." *Clin Endocrinol (Oxf)* 52(6): 775-780.

Genazzani, A. R., S. Inglese, et al. (2004). "Long-term low-dose dehydroepiandrosterone replacement therapy in aging males with partial androgen deficiency." *Aging Male* 7(2): 133-143.

Gibbs, R. B. and P. Aggarwal (1998). "Estrogen and basal forebrain cholinergic neurons: implications for brain aging and Alzheimer's disease-related cognitive decline." *Horm Behav* 34(2): 98-111.

Goldstat, R., E. Briganti, et al. (2003). "Transdermal testosterone therapy improves well-being, mood, and sexual function in premenopausal women." *Menopause* 10(5): 390-398.

Gooren, L. J. (1987). "Androgen levels and sex functions in testosterone-treated hypogonadal men." *Arch Sex Behav* 16(6): 463-473.

Gooren, L. J. (1994). "A ten-year safety study of the oral androgen testosterone undecanoate." *J Androl* 15(3): 212-215.

Gordon, C. M., E. Grace, et al. (2002). "Effects of oral dehydroepiandrosterone on bone density in young women with anorexia nervosa: a randomized trial." *J Clin Endocrinol Metab* 87(11): 4935-4941.

Gordon, G. B., D. E. Bush, et al. (1988). "Reduction of atherosclerosis by administration of dehydroepiandrosterone. A study in the hypercholesterolemic New Zealand white rabbit with aortic intimal injury." *J. Clin. Invest.* 82: 712-720.

Gordon, G. B., L. M. Shantz, et al. (1987). "Modulation of growth, differentiation and carcinogenesis by dehydroepiandrosterone." *Adv. Enzyme Regul.* 26: 355-382.

Gray, P. B., A. B. Singh, et al. (2005). "Dose-dependent effects of testosterone on sexual function, mood, and visuospatial cognition in older men." *J Clin Endocrinol Metab* 90(7): 3838-3846.

Grimley Evans, J., R. Malouf, et al. (2006). "Dehydroepiandrosterone (DHEA) supplementation for cognitive function in healthy elderly people." *Cochrane Database Syst Rev*(4): CD006221.

Guay, A. T., J. Jacobson, et al. (2003). "Clomiphene increases free testosterone levels in men with both secondary hypogonadism and erectile dysfunction: who does and does not benefit?" *Int J Impot Res* 15(3): 156-165.

Gurnell, E. M., P. J. Hunt, et al. (2008). "Long-term DHEA replacement in primary adrenal insufficiency: a randomized, controlled trial." *J Clin Endocrinol Metab* 93(2): 400-409.

Hackbert, L. and J. R. Heiman (2002). "Acute dehydroepiandrosterone (DHEA) effects on sexual arousal in postmenopausal women." *J Womens Health Gend Based Med* 11(2): 155-162.

Haddad, R. M., C. C. Kennedy, et al. (2007). "Testosterone and cardiovascular risk in men: a systematic review and meta-analysis of randomized placebo-controlled trials." *Mayo Clin Proc* 82(1): 29-39.

Haffner, S. M., R. S. Kushwaha, et al. (1983). "Studies on the metabolic mechanism of reduced high density lipoproteins during anabolic steroid therapy." *Metabolism* 32(4): 413-420.

Hajszan, T., N. J. MacLusky, et al. (2007). "Effects of androgens and estradiol on spine synapse formation in the prefrontal cortex of normal and testicular feminization mutant male rats." *Endocrinology* 148(5): 1963-1967.

Hak, A. E., J. C. Witteman, et al. (2002). "Low levels of endogenous androgens increase the risk of atherosclerosis in elderly men: the Rotterdam study." *J Clin Endocrinol Metab* 87(8): 3632-3639.

Hall, S. A., G. R. Esche, et al. (2008). "Correlates of low testosterone and symptomatic androgen deficiency in a population-based sample." *J Clin Endocrinol Metab* 93(10): 3870-3877.

Han, D. H., P. A. Hansen, et al. (1998). "DHEA treatment reduces fat accumulation and protects against insulin resistance in male rats." *J Gerontol A Biol Sci Med Sci* 53(1): B19-24.

Handelsman, D. J. (2006). "Clinical review: The rationale for banning human chorionic gonadotropin and estrogen blockers in sport." *J Clin Endocrinol Metab* 91(5): 1646-1653.

Hansen, P. A., D. H. Han, et al. (1997). "DHEA protects against visceral obesity and muscle insulin resistance in rats fed a high-fat diet." *Am J Physiol* 273(5 Pt 2): R1704-1708.

Harman, S. M., E. J. Metter, et al. (2001). "Longitudinal effects of aging on serum total and free testosterone levels in healthy men. Baltimore Longitudinal Study of Aging." *J Clin Endocrinol Metab* 86(2): 724-731.

Hayashi, T., T. Esaki, et al. (2000). "Dehydroepiandrosterone retards atherosclerosis formation through its conversion to estrogen: the possible role of nitric oxide." *Arterioscler Thromb Vasc Biol* 20(3): 782-792.

Hazzard, W. R., S. M. Haffner, et al. (1984). "Preliminary report: kinetic studies on the modulation of high-density lipoprotein, apolipoprotein, and subfraction metabolism by sex steroids in a postmenopausal woman." *Metabolism* 33(9): 779-784.

Henderson, E., J. Y. Yang, et al. (1992). "Dehydroepiandrosterone (DHEA) and synthetic DHEA analogs are modest inhibitors of HIV-1 IIIB replication." *Aids Res. Hum. Retroviruses* 8: 625-631.

Hennernan, P. M. and S. Wallach (1957). "The role of androgens and estrogens and their metabolic effects. A review of the prolonged use of estrogens and androgens in postmenopausal and senile osteoporosis." *AMA: Arch. Int. Med.* 100: 715-723.

Herrington, D. M., G. B. Gordon, et al. (1990). "Plasma dehydroepiandrosterone and dehydroepiandrosterone sulfate in patients undergoing diagnostic coronary angiography." *J. Am. Coll. Cardiol.* 16: 862-870.

Herrington, D. M., N. Nanjee, et al. (1996). "Dehydroepiandrosterone and cardiac allograft vasculopathy." *J Heart Lung Transplant* 15(1 Pt 1): 88-93.

Hogervorst, E., S. Bandelow, et al. (2004). "Low free testosterone is an independent risk factor for Alzheimer's disease." *Exp Gerontol* 39(11-12): 1633-1639.

Hogervorst, E., J. Williams, et al. (2000). "The nature of the effect of female gonadal hormone replacement therapy on cognitive function in post-menopausal women: a meta-analysis." *Neuroscience* 101(3): 485-512.

Holland, J., S. Bandelow, et al. (2011). "Testosterone levels and cognition in elderly men: a review." *Maturitas* 69(4): 322-337.

Holmang, S., P. Marin, et al. (1993). "Effect of long-term oral testosterone undecanoate treatment on prostate volume and serum prostate-specific antigen concentration in eugonadal middle-aged men." *Prostate* 23(2): 99-106.

Huang, J., H. Guan, et al. (2004). "Estrogen regulates neprilysin activity in rat brain." *Neurosci Lett* 367(1): 85-87.

Huggins, C. and C. V. Hodges (1941). "Studies of prostatic cancer. I. Effect of castration, estrogen and androgen injections on serum phosphatases in metastatic carcinoma of the prostate." *Cancer Res.* 1: 293-307.

Hughes, V. A., W. R. Frontera, et al. (2002). "Longitudinal changes in body composition in older men and women: role of body weight change and physical activity." *Am J Clin Nutr* 76(2): 473-481.

Hunt, P. J., E. M. Gurnell, et al. (2000). "Improvement in mood and fatigue after dehydroepiandrosterone replacement in Addison's disease in a randomized, double blind trial." *J Clin Endocrinol Metab* 85(12): 4650-4656.

Huppert, F. A. and J. K. Van Niekerk (2001). "Dehydroepiandrosterone (DHEA) supplementation for cognitive function." *Cochrane Database Syst Rev* 2(2): CD 000304.

Iannuzzi-Sucich, M., K. M. Prestwood, et al. (2002). "Prevalence of sarcopenia and predictors of skeletal muscle mass in healthy, older men and women." *J Gerontol A Biol Sci Med Sci* 57(12): M772-777.

Isidori, A. M., M. Caprio, et al. (1999). "Leptin and androgens in male obesity: evidence for leptin contribution to reduced androgen levels." *J Clin Endocrinol Metab* 84(10): 3673-3680.

Isidori, A. M., E. Giannetta, et al. (2005). "Effects of testosterone on body composition, bone metabolism and serum lipid profile in middle-aged men: a meta-analysis." *Clin Endocrinol (Oxf)* 63(3): 280-293.

Johannsson, G., P. Burman, et al. (2002). "Low dose dehydroepiandrosterone affects behavior in hypopituitary androgen-deficient women: a placebo-controlled trial." *J Clin Endocrinol Metab* 87(5): 2046-2052.

Jones, T. H., S. Arver, et al. (2011). "Testosterone replacement in hypogonadal men with type 2 diabetes and/or metabolic syndrome (the TIMES2 study)." *Diabetes Care* 34(4): 828-837.

Jones, T. H. and F. Saad (2009). "The effects of testosterone on risk factors for, and the mediators of, the atherosclerotic process." *Atherosclerosis* 207(2): 318-327.

Jordan, V. C., E. Phelps, et al. (1987). "Effects of antiestrogens on bone in castrated and intact female rats." *Breast Cancer Res. Treat.* 10: 31-35.

Kallman, D. A., C. C. Plato, et al. (1990). "The role of muscle loss in the age-related decline of grip strength: cross-sectional and longitudinal perspectives." *J Gerontol* 45(3): M82-88.

Kantor, M. A., A. Bianchini, et al. (1985). "Androgens reduce HDL2-cholesterol and increase hepatic triglyceride lipase activity." *Med Sci Sports Exerc* 17(4): 462-465.

Kapoor, D., E. Goodwin, et al. (2006). "Testosterone replacement therapy improves insulin resistance, glycaemic control, visceral adiposity and hypercholesterolaemia in hypogonadal men with type 2 diabetes." *Eur J Endocrinol* 154(6): 899-906.

Kapoor, D., C. J. Malkin, et al. (2005). "Androgens, insulin resistance and vascular disease in men." *Clin Endocrinol (Oxf)* 63(3): 239-250.

Kapur, S. P. and A. H. Reddi (1989). "Influence of testosterone and dihydrotestosterone on bone-matrix induced endochondral bone formation." *Calcif. Tissue Int.* 44: 108-113.

Katz, D. J., O. Nabulsi, et al. (2011). "Outcomes of clomiphene citrate treatment in young hypogonadal men." *BJU Int* 110(4): 573-578.

Kawano, H., H. Yasue, et al. (2003). "Dehydroepiandrosterone supplementation improves endothelial function and insulin sensitivity in men." *J Clin Endocrinol Metab* 88(7): 3190-3195.

Kelleher, S., A. J. Conway, et al. (2004). "Blood testosterone threshold for androgen deficiency symptoms." *J Clin Endocrinol Metab* 89(8): 3813-3817.

Kenny, A. M., K. M. Prestwood, et al. (2001). "Effects of transdermal testosterone on bone and muscle in older men with low bioavailable testosterone levels." *J Gerontol A Biol Sci Med Sci* 56(5): M266-272.

Khaw, K. T., M. Dowsett, et al. (2007). "Endogenous testosterone and mortality due to all causes, cardiovascular disease, and cancer in men: European prospective investigation into cancer in Norfolk (EPIC-Norfolk) Prospective Population Study." *Circulation* 116(23): 2694-2701.

Kim, E. D., L. Crosnoe, et al. (2013). "The treatment of hypogonadism in men of reproductive age." *Fertil Steril* 99(3): 718-724.

Kleerekoper, M., A. R. Villanueva, et al. (1985). "The role of three-dimensional trabecular microstructure in the pathogenesis of vertebral compression fractures." *Calcif. Tissue Int.* 37: 594-597.

Komesaroff, P. A. (2008). "Unravelling the enigma of dehydroepiandrosterone: moving forward step by step." *Endocrinology* 149(3): 886-888.

Kopelman, P. G. (2000). "Obesity as a medical problem." *Nature* 404(6778): 635-643.

Kostka, T., L. M. Arsac, et al. (2000). "Leg extensor power and dehydroepiandrosterone sulfate, insulin-like growth factor-I and testosterone in healthy active elderly people." *Eur J Appl Physiol* 82(1-2): 83-90.

Kramer, C. Y. (1956). "Extension of multiple range tests to group means with unique numbers of replications." *Biometrics* 12: 307-310.

Koller, C. and P. Buri (1987). "Propriétés et intérêt pharmaceutique des gels thermoréversibles à base de poloxamers et poloxamines." S. T. P. PHARMA 3(2): 115-124.

Kurzman, I. D., D. L. Panciera, et al. (1998). "The effect of dehydroepiandrosterone combined with a low-fat diet in spontaneously obese dogs: a clinical trial." *Obes Res* 6(1): 20-28.

Kushnir, M. M., T. Blamires, et al. (2010). "Liquid chromatography-tandem mass spectrometry assay for androstenedione, dehydroepiandrosterone, and testosterone with pediatric and adult reference intervals." *Clin Chem* 56(7): 1138-1147.

Labrie, C., A. Bélanger, et al. (1988). "Androgenic activity of dehydroepiandrosterone and androstenedione in the rat ventral prostate." *Endocrinology* 123: 1412-1417.

Labrie, F. (1991). "Intracrinology." *Mol. Cell. Endocrinol.* 78: C113-C118.

Labrie, F. (2010a). "DHEA after Menopause—Sole source of sex steroids and potential sex steroid deficiency treatment." *Menopause Management* 19: 14-24.

Labrie, F. (2010b). DHEA, important source of sex steroids in men and even more in women. *Neuroendocrinology, The Normal Neuroendocrine System, Progress in Brain Research.* L. Martini, Chrousos G. P, Labrie F, Pacak K and D. Pfaff, eds., Elsevier. 182 (Chapter 4): 97-148.

Labrie, F. (2011). "Blockade of testicular and adrenal androgens in prostate cancer treatment." *Nat Rev Urol* 8(2): 73-85.

Labrie, F., D. Archer, et al. (2009a). "Effect on intravaginal dehydroepiandrosterone (Prasterone) on libido and sexual dysfunction in postmenopausal women." *Menopause* 16: 923-931.

Labrie, F., D. Archer, et al. (2009b). "Intravaginal dehydroepiandrosterone (Prasterone), a physiological and highly efficient treatment of vaginal atrophy." *Menopause* 16: 907-922.

Labrie, F., D. Archer, et al. (2009c). "Serum steroid levels during 12-week intravaginal dehydroepiandrosterone administration." *Menopause* 16: 897-906.

Labrie, F.; A. Bélanger, et al. (2006). "Androgen glucuronides, instead of testosterone, as the new markers of androgenic activity in women." *J Steroid Biochem Mol Biol* 99: 182-188.

Labrie, F., A. Bélanger, et al. (1997a). "Physiological changes in dehydroepiandrosterone are not reflected by serum levels of active androgens and estrogens but of their metabolites: intracrinology." *J Clin Endocrinol Metab* 82(8): 2403-2409.

Labrie, F., A. Bélanger, et al. (1997b). "Marked decline in serum concentrations of adrenal C19 sex steroid precursors and conjugated androgen metabolites during aging." *J Clin Endocrinol Metab* 82: 2396-2402.

Labrie, F., A. Bélanger, et al. (1993). "Science behind total androgen blockade: from gene to combination therapy." *Clin. Invest. Med.* 16: 475-492.

Labrie, F., A. Bélanger, et al. (1998). "DHEA and the intracrine formation of androgens and estrogens in peripheral target tissues: its role during aging." *Steroids* 63(5-6): 322-328.

Labrie, F., A. Bélanger, et al. (2005). "Gonadotropin-releasing hormone agonists in the treatment of prostate cancer." *Endocrine Reviews* 26(3): 361-379.

Labrie, F., B. Candas, et al. (2002). "Can combined androgen blockade provide long-term control or possible cure of localized prostate cancer?" *Urology* 60(1): 115-119.

Labrie, F., L. Cusan, et al. (2009). "Comparable amounts of sex steroids are made outside the gonads in men and women: strong lesson for hormone therapy of prostate and breast cancer." *J Steroid Biochem Mol Biol* 113: 52-56.

Labrie, F., P. Diamond, et al. (1997a). "Effect of 12-month DHEA replacement therapy on bone, vagina, and endometrium in postmenopausal women." *J. Clin. Endocrinol. Metab.* 82: 3498-3505.

Labrie, F., A. Dupont, et al. (1985). Complete androgen blockade for the treatment of prostate cancer. *Important Advances in Oncology.* V. T. de Vita, S. Hellman and S. A. Rosenberg. Philadelphia, J. B. Lippincott: 193-217.

Labrie, F., A. Dupont, et al. (1982). "New hormonal therapy in prostatic carcinoma: combined treatment with an LHRH agonist and an antiandrogen." *Clin. Invest. Med.* 5: 267-275.

Labrie, F., V. Luu-The, et al. (1997). "The key role of 17b-HSDs in sex steroid biology." *Steroids* 62: 148-158.

Labrie, F., C. Martel, et al. (2011). "Wide distribution of the serum dehydroepiandrosterone and sex steroid levels in postmenopausal women: role of the ovary?" *Menopause* 18(1): 30-43.

Labrie, F., J. Simard, et al. (1992a). "Structure, function and tissue-specific gene expression of 3b-hydroxysteroid dehydrogenase/5-ene-4-ene isomerase enzymes in classical and peripheral intracrine steroidogenic tissues." *J. Steroid Biochem. Mol. Biol.* 43: 805-826.

Labrie, F., J. Simard, et al. (1996a). The 3b-hydroxysteroid dehydrogenase/isomerase gene family: lessons from type II 3b-HSD congenital deficiency. *Signal Transduction in*

Testicular Cells. *Ernst Schering Research Foundation Workshop.* V. Hansson, F. O. Levy and K. Taskén. Berlin, Heidelberg, N.Y., Springer-Verlag. Suppl. 2: 185-218.

Labrie, F., J. Simard, et al. (1992b). "Structure and tissue-specific expression of 3b-hydroxysteroid dehydrogenase/ 5-ene-4-ene isomerase genes in human and rat classical and peripheral steroidogenic tissues." *J. Steroid Biochem. Mol. Biol.* 41: 421-435.

Labrie, F., J. Simard, et al. (1994). "Structure, regulation and role of 3b-hydroxysteroid dehydrogenase, 17b-hydroxysteroid dehydrogenase and aromatase enzymes in formation of sex steroids in classical and peripheral intracrine tissues." *Hormone, Enzymes and Receptors:* 451-474.

Labrie, F., Y. Sugimoto, et al. (1992). "Structure of human type II 5a-reductase." *Endocrinology* 131: 1571-1573.

Labrie, Y., F. Durocher, et al. (1995). "The human type II 17b-hydroxysteroid dehydrogenase gene encodes two alternatively-spliced messenger RNA species." *DNA Cell Biol.* 14: 849-861.

Lamberts, S. W. (2003). "The endocrinology of gonadal involution: menopause and andropause." *Ann Endocrinol (Paris)* 64(2): 77-81.

Larsson, L., G. Grimby, et al. (1979). "Muscle strength and speed of movement in relation to age and muscle morphology." *J Appl Physiol* 46(3): 451-456.

Lasco, A., N. Frisina, et al. (2001). "Metabolic effects of dehydroepiandrosterone replacement therapy in postmenopausal women." *Eur J Endocrinol* 145: 457-461.

Lauffenburger, T., A. J. Olah, et al. (1977). "Bone remodeling and calcium metabolism: a correlated histomorphometric, calcium kinetic, and biochemical study in patients with osteoporosis and Paget's disease." *Metabolism* 26: 589-606.

Laumann, E. O., A. Paik, et al. (1999). "Sexual dysfunction in the United States: prevalence and predictors." *Jama* 281(6): 537-544.

LeBlanc, E. S., J. Janowsky, et al. (2001). "Hormone replacement therapy and cognition: systematic review and meta-analysis." *Jama* 285(11): 1489-1499.

Li, S., X. Yan, et al. (1993). "Prevention by dehydroepiandrosterone of the development of mammary carcinoma induced by 7,12-dimethylbenz(a)anthracene (DMBA) in the rat." *Breast Cancer Res. Treat.* 29: 203-217.

Libe, R., L. Barbetta, et al. (2004). "Effects of dehydroepiandrosterone (DHEA) supplementation on hormonal, metabolic and behavioral status in patients with hypoadrenalism." *J Endocrinol Invest* 27(8): 736-741.

Liu, P. Y., H. W. Baker, et al. (2009). "Induction of spermatogenesis and fertility during gonadotropin treatment of gonadotropin-deficient infertile men: predictors of fertility outcome." *J Clin Endocrinol Metab* 94(3): 801-808.

Liu, P. Y., R. S. Swerdloff, et al. (2006). "Rate, extent, and modifiers of spermatogenic recovery after hormonal male contraception: an integrated analysis." *Lancet* 367(9520): 1412-1420.

Lobo, R. A. (1991). "Clinical review 27: Effects of hormonal replacement on lipids and lipoproteins in postmenopausal women." *J. Clin. Endocrinol. Metab.* 73(5): 925-930.

Lobo, R. A., R. C. Rosen, et al. (2003). "Comparative effects of oral esterified estrogens with and without methyltestosterone on endocrine profiles and dimensions of sexual function in postmenopausal women with hypoactive sexual desire." *Fertil Steril* 79(6): 1341-1352.

Lovas, K., G. Gebre-Medhin, et al. (2003). "Replacement of dehydroepiandrosterone in adrenal failure: no benefit for subjective health status and sexuality in a 9-month, randomized, parallel group clinical trial." *J Clin Endocrinol Metab* 88(3): 1112-1118.

Lovas, K. and E. S. Husebye (2008). "Replacement therapy for Addison's disease: recent developments." *Expert Opin Investig Drugs* 17(4): 497-509.

Lunenfeld, B. and E. Nieschlag (2007). "Testosterone therapy in the aging male." *Aging Male* 10(3): 139-153.

Luo, S., A. Sourla, et al. (1997). "Combined effects of dehydroepiandrosterone and EM-800 on bone mass, serum lipids, and the development of dimethylbenz(a) anthracene (DMBA)-induced mammary carcinoma in the rat." *Endocrinology* 138: 4435-4444.

Luu-The, V., I. Dufort, et al. (1995). "Structural characterization and expression of the human dehydroepiandrosterone sulfotransferase gene." *DNA Cell Biol.* 14: 511-518.

Luu-The, V., Y. Zhang, et al. (1995). "Characteristics of human types 1, 2 and 3 17b-hydroxysteroid dehydrogenase activities: oxidation-reduction and inhibition." *J. Steroid Biochem. Mol. Biol.* 55: 581-587.

MacEwen, E. G. and I. D. Kurzman (1991). "Obesity in the dog: role of the adrenal steroid dehydroepiandrosterone (DHEA)." *J. Nutr.* 121: S51-S55.

Maggi, M., J. Buvat, et al. (2013). "Hormonal causes of male sexual dysfunctions and their management (hyperprolactinemia, thyroid disorders, GH disorders, and DHEA)." *J Sex Med* 10(3): 661-677.

Malkin, C. J., P. J. Pugh, et al. (2004). "Testosterone replacement in hypogonadal men with angina improves ischaemic threshold and quality of life." *Heart* 90(8): 871-876.

Malkin, C. J., P. J. Pugh, et al. (2006). "Testosterone therapy in men with moderate severity heart failure: a double-blind randomized placebo controlled trial." *Eur Heart J* 27(1): 57-64.

Manson, J. E., S. S. Bassuk, et al. (2006). "Postmenopausal hormone therapy: new questions and the case for new clinical trials." *Menopause* 13(1): 139-147.

Marin, P., S. Holmang, et al. (1993). "Androgen treatment of abdominally obese women." *Obes. Res.* 1: 245-251.

Marks, L. S., N. A. Mazer, et al. (2006). "Effect of testosterone replacement therapy on prostate tissue in men with late-onset hypogonadism: a randomized controlled trial." *Jama* 296(19): 2351-2361.

Martel, C., A. Sourla, et al. (1998). "Predominant androgenic component in the stimulatory effect of dehydroepiandrosterone on bone mineral density in the rat." *J. Endocrinol.* 157: 433-442.

Matsumoto, A. M. (2002). "Andropause: clinical implications of the decline in serum testosterone levels with aging in men." *J Gerontol A Biol Sci Med Sci* 57(2): M76-99.

McEwen, B. S. and S. E. Alves (1999). "Estrogen actions in the central nervous system." *Endocr Rev* 20(3): 279-307.

McEwen, B. S., E. Gould, et al. (1995). "Oestrogens and the structural and functional plasticity of neurons: implications for memory, ageing and neurodegenerative processes." *Ciba Found Symp* 191: 52-66; discussion 66-73.

Melsen, F., B. Melsen, et al. (1978). "Histomorphometric analysis of normal bone from the iliac crest." *Acta Pathol. Microbiol. Scand.* 86: 70-81.

Melton, L. J., 3rd, S. Khosla, et al. (2000). "Epidemiology of sarcopenia." *Mayo Clin Proc* 75 Suppl: S10-12; discussion S12-13.

Meunier, P. J., C. Salson, et al. (1987). "Skeletal distribution and biochemical parameters of Paget's disease." *Clin. Orthop.* 217: 37-44.

Miller, K. K., W. Rosner, et al. (2004). "Measurement of free testosterone in normal women and women with androgen deficiency: comparison of methods." *J Clin Endocrinol Metab* 89(2): 525-533.

Mitchell, L. E., D. L. Sprecher, et al. (1994). "Evidence for an association between dehydroepiandrosterone sulfate and nonfatal, premature myocardial infarction in males." *Circulation* 89(1): 89-93.

Mohan, P. F., J. S. Ihnen, et al. (1990). "Effects of dehydroepiandrosterone treatment in rats with diet-induced obesity." *J. Nutr.* 120: 1103-1114.

Monk, D. and H. Brodaty (2000). "Use of estrogens for the prevention and treatment of Alzheimer's disease." *Dement Geriatr Cogn Disord* 11(1): 1-10.

Moore, C., D. Huebler, et al. (2004). "The Aging Males' Symptoms scale (AMS) as outcome measure for treatment of androgen deficiency." *Eur Urol* 46(1): 80-87.

Morales, A. J., R. H. Haubrich, et al. (1998). "The effect of six months treatment with a 100 mg daily dose of dehydroepiandrosterone (DHEA) on circulating sex steroids, body composition and muscle strength in age-advanced men and women." *Clin Endocrinol (Oxf)* 49(4): 421-432.

Morales, A. J., J. J. Nolan, et al. (1994). "Effects of replacement dose of dehydroepiandrosterone in men and women of advancing age." *J. Clin. Endocrinol. Metab.* 78: 1360-1367.

Morley, J. E. (2003). "Testosterone and behavior." *Clin Geriatr Med* 19(3): 605-616.

Morley, J. E., E. Charlton, et al. (2000). "Validation of a screening questionnaire for androgen deficiency in aging males." *Metabolism* 49(9): 1239-1242.

Morley, J. E. and H. M. Perry, 3rd (2003). "Andropause: an old concept in new clothing." *Clin Geriatr Med* 19(3): 507-528.

Morrison, J. H., R. D. Brinton, et al. (2006). "Estrogen, menopause, and the aging brain: how basic neuroscience can inform hormone therapy in women." *J Neurosci* 26(41): 10332-10348.

Mortola, J. F. and S. S. Yen (1990). "The effects of oral dehydroepiandrosterone on endocrine-metabolic parameters in postmenopausal women." *J Clin Endocrinol Metab* 71(3): 696-704.

Mostaghel, E. A., S. T. Page, et al. (2007). "Intraprostatic androgens and androgen-regulated gene expression persist after testosterone suppression: therapeutic implications for castration-resistant prostate cancer." *Cancer Res* 67(10): 5033-5041.

Murray, R. and P. Pitt (1985). "Treatment of advanced prostatic cancer, resistant to conventional therapy, with aminoglutethimide." *Eur J Cancer Clin Oncol* 21(4): 453-458.

Nair, K. S., R. A. Rizza, et al. (2006). "DHEA in elderly women and DHEA or testosterone in elderly men." *N Engl J Med* 355(16): 1647-1659.

Nathorst-Boos, J. and B. von Schoultz (1992). "Psychological reactions and sexual life after hysterectomy with and without oophorectomy." *Gynecol Obstet Invest* 34(2): 97-101.

Need, A. G., M. Horowitz, et al. (1989). "Effects of nandrolone decanoate and antiresorptive therapy on vertebral density in osteoporotic postmenopausal women." *Arch. Intern. Med.* 149: 57-60.

Nestler, J. E., C. O. Barlascini, et al. (1988). "Dehydroepiandrosterone reduces serum low density lipoprotein levels and body fat but does not alter insulin sensitivity in normal men." *J. Clin. Endocrinol. Metab.* 66: 57-61.

Nishiyama, T., Y. Hashimoto, et al. (2004). "The influence of androgen deprivation therapy on dihydrotestosterone levels in the prostatic tissue of patients with prostate cancer." *Clin Cancer Res* 10(21): 7121-7126.

Notelovitz, M., N. Watts, et al. (1992). Effects of estrogen plus low dose androgen vs estrogen alone on menopausal symptoms in oophorectomized/hysterectomized women. North Am. Menopause Soc., Cleveland.

O'Connor, D. B., D. M. Lee, et al. (2011). "The Relationships between Sex Hormones and Sexual Function in Middle-Aged and Older European Men." *J Clin Endocrinol Metab* 96(10): E1577-E1587.

O'Leary, M. P., F. J. Fowler, et al. (1995). "A brief male sexual function inventory for urology." *Urology* 46(5): 697-706.

Ohlsson, C., F. Labrie, et al. (2010). "Low serum levels of dehydroepiandrosterone sulfate predict all-cause and cardiovascular mortality in elderly men." *J Clin Endocrinol Metab* 95: 4406-4414.

Ota, H., M. Akishita, et al. (2012). "Testosterone deficiency accelerates neuronal and vascular aging of SAMP8 mice: protective role of eNOS and SIRT1." *PLoS One* 7(1): e29598.

Page, S. T., J. K. Amory, et al. (2005). "Exogenous testosterone (T) alone or with finasteride increases physical performance, grip strength, and lean body mass in older men with low serum T." *J Clin Endocrinol Metab* 90(3): 1502-1510.

Pechersky, A. V., V. I. Mazurov, et al. (2002). "Androgen administration in middle-aged and ageing men: effects of oral testosterone undecanoate on dihydrotestosterone, oestradiol and prostate volume." *Int J Androl* 25(2): 119-125.

Percheron, G., J. Y. Hogrel, et al. (2003). "Effect of 1-year oral administration of dehydroepiandrosterone to 60- to 80-year-old individuals on muscle function and cross-sectional area: a double-blind placebo-controlled trial." *Arch Intern Med* 163(6): 720-727.

Petri, M. A., R. G. Lahita, et al. (2002). "Effects of prasterone on corticosteroid requirements of women with systemic lupus erythematosus: a double-blind, randomized, placebo-controlled trial." *Arthritis Rheum* 46(7): 1820-1829.

Petri, M. A., P. J. Mease, et al. (2004). "Effects of prasterone on disease activity and symptoms in women with active systemic lupus erythematosus." *Arthritis Rheum* 50(9): 2858-2868.

Pike, C. J., J. C. Carroll, et al. (2009). "Protective actions of sex steroid hormones in Alzheimer's disease." *Front Neuroendocrinol* 30(2): 239-258.

Poretsky, L., D. J. Brillon, et al. (2006). "Endocrine effects of oral dehydroepiandrosterone in men with HIV infection: a prospective, randomized, double-blind, placebo-controlled trial." *Metabolism* 55(7): 858-870.

Prostate Cancer Triallists' Collaborative Group (2000). "Maximum androgen blockade in advanced prostate cancer: an overview of the randomised trials." *Lancet* 355: 1491-1498.

Pugh, P. J., R. D. Jones, et al. (2004). "Testosterone treatment for men with chronic heart failure." *Heart* 90(4): 446-447.

Raisz, L. G., B. Wiita, et al. (1996). "Comparison of the effects of estrogen alone and estrogen plus androgen on biochemical markers of bone formation and resorption in postmenopausal women." *J Clin Endocrinol Metab* 81(1): 37-43.

Rasmussen, K. R., M. J. Arrowood, et al. (1992). "Effectiveness of dehydroepiandrosterone in reduction of cryptosporidial activity in immunosuppressed rats." *Antimicrob. Agents Chemother.* 36: 220-222.

Raven, P. W. and J. P. Hinson (2007). "Dehydroepiandrosterone (DHEA) and the menopause: an update." *Menopause Int* 13(2): 75-78.

Rocca, W. A., J. H. Bower, et al. (2007). "Increased risk of cognitive impairment or dementia in women who underwent oophorectomy before menopause." *Neurology* 69(11): 1074-1083.

Rocca, W. A., B. R. Grossardt, et al. (2006). "Survival patterns after oophorectomy in premenopausal women: a population-based cohort study." *Lancet Oncol* 7(10): 821-828.

Roy, T. A., M. R. Blackman, et al. (2002). "Interrelationships of serum testosterone and free testosterone index with FFM and strength in aging men." *Am J Physiol Endocrinol Metab* 283(2): E284-294.

Saad, F., L. J. Gooren, et al. (2008). "A dose-response study of testosterone on sexual dysfunction and features of the metabolic syndrome using testosterone gel and parenteral testosterone undecanoate." *J Androl* 29(1): 102-105.

Salmimies, P., G. Kockott, et al. (1982). "Effects of testosterone replacement on sexual behavior in hypogonadal men." *Arch Sex Behav* 11(4): 345-353.

Savvas, M., J. W. W. Studd, et al. (1988). "Skeletal effects of oral oestrogen compared with subcutaneous oestrogen and testosterone in postmenopausal women." *Br. Med. J.* 297: 331-333.

Schaap, L. A., S. M. Pluijm, et al. (2005). "The association of sex hormone levels with poor mobility, low muscle strength and incidence of falls among older men and women." *Clin Endocrinol (Oxf)* 63(2): 152-160.

Schriock, E. D., C. K. Buffington, et al. (1988). "Divergent correlations of circulating dehydroepiandrosterone sulfate and testosterone with insulin levels and insulin receptor binding." *J. Clin. Endocrinol. Metab.* 66: 1329-1331.

Schwartz, A. G., L. Pashko, et al. (1986). "Inhibition of tumor development by dehydroepiandrosterone and related steroids." *Toxicol. Pathol.* 14: 357-362.

Seftel, A. D., R. J. Mack, et al. (2004). "Restorative increases in serum testosterone levels are significantly correlated to improvements in sexual functioning." *J Androl* 25(6): 963-972.

Shabsigh, A., Y. Kang, et al. (2005). "Clomiphene citrate effects on testosterone/estrogen ratio in male hypogonadism." *J Sex Med* 2(5): 716-721.

Sherwin, B. B. (1988). "Affective changes with estrogen and androgen replacement therapy in surgically menopausal women." *J. Affect. Disord.* 14: 177-187.

Sherwin, B. B. and M. M. Gelfand (1985). "Differential symptom response to parenteral estrogen and/or androgen administration in the surgical menopause." *Am. J. Obstet. Gynecol.* 151: 153-160.

Sherwin, B. B. and M. M. Gelfand (1987). "The role of androgen in the maintenance of sexual functioning in oophorectomized women." *Psychosom Med.* 49: 397-409.

Shifren, J. L., G. D. Braunstein, at al. (2000). "Transdermal testosterone treatment in women with impaired sexual function after oophorectomy." *N Engl J Med* 343(10): 682-688.

Shigehara, K. and M. Namiki (2011). "Late-onset hypogonadism syndrome and lower urinary tract symptoms." *Korean J Urol* 52(10): 657-663.

Shimokata, H., J. D. Tobin, et al. (1989). "Studies in the distribution of body fat: I. Effects of age, sex, and obesity." *J Gerontol* 44(2): M66-73.

Shores, M. M., N. L. Smith, et al. (2012). "Testosterone treatment and mortality in men with low testosterone levels." *J Clin Endocrinol Metab* 97(6): 2050-2058.

Sibonga, J. D., G. L. Evans, et al. (1996). "Ovarian status influences the skeletal effects of tamoxifen in adult rats." *Breast Cancer Res. Treat.* 41: 71-79.

Sih, R., J. E. Morley, et al. (1997). "Testosterone replacement in older hypogonadal men: a 12-month randomized controlled trial." *J Clin Endocrinol Metab* 82(6): 1661-1667.

Simard, J., R. Sanchez, et al. (1997). "Blockade of the stimulatory effect of estrogens, OH-Tamoxifen, OH-Toremifene, Droloxifene and Raloxifene on alkaline phosphatase activity by the antiestrogen EM-800 in human endometrial adenocarcinoma Ishikawa cells." *Cancer Res.* 57: 3494-3497.

Simpkins, J. W., P. S. Green, et al. (1997). "Role of estrogen replacement therapy in memory enhancement and the prevention of neuronal loss associated with Alzheimer's disease." *Am J Med* 103(3A): 19S-25S.

Siris, E. S., Y. T. Chen, et al. (2004). "Bone mineral density thresholds for pharmacological intervention to prevent fractures." *Arch Intern Med* 164(10): 1108-1112.

Smith, K. W., H. A. Feldman, et al. (2000). "Construction and field validation of a self-administered screener for testosterone deficiency (hypogonadism) in ageing men." *Clin Endocrinol (Oxf)* 53(6): 703-711.

Smith, M. R. (2006). "Treatment-related osteoporosis in men with prostate cancer." *Clin Cancer Res* 12(20 Pt 2): 6315s-6319s.

Snyder, P. J., H. Peachey, et al. (2000). "Effects of testosterone replacement in hypogonadal men." *J Clin Endocrinol Metab* 85(8): 2670-2677.

Snyder, P. J., H. Peachey, et al. (1999). "Effect of testosterone treatment on body composition and muscle strength in men over 65 years of age." *J Clin Endocrinol Metab* 84(8): 2647-2653.

Storer, T. W., L. Magliano, et al. (2003). "Testosterone dose-dependently increases maximal voluntary strength and leg power, but does not affect fatigability or specific tension." *J Clin Endocrinol Metab* 88(4): 1478-1485.

Studd, J. W., W. P. Collins, et al. (1977). "Oestradiol and testosterone implants in the treatment of psychosexual problems in the post-menopausal woman." *Br. J. Obstet. Gynecol.* 84: 314-315.

Suzuki, T., N. Suzuki, et al. (1991). "Dehydroepiandrosterone enhances IL2 production and cytotoxic effector function of human T cells." *Clin. Immunol. Immunopathol.* 61: 202-211.

Tagliaferro, A. R., J. R. Davis, et al. (1986). "Effects of dehydroepiandrosterone acetate on metabolism, body weight and composition of male and female rats." *J. Nutr.* 116: 1977-1983.

Takao, T., A. Tsujimura, et al. (2009). "Lower urinary tract symptoms after hormone replacement therapy in Japanese patients with late-onset hypogonadism: a preliminary report." *Int J Urol* 16(2): 212-214.

Tan, K. C., S. W. Shiu, et al. (1998). "Effects of testosterone replacement on HDL subfractions and apolipoprotein A-I containing lipoproteins." *Clin Endocrinol (Oxf)* 48(2): 187-194.

Tan, R. S. and S. J. Pu (2003). "A pilot study on the effects of testosterone in hypogonadal aging male patients with Alzheimer's disease." *Aging Male* 6(1): 13-17.

Taylor, F. and L. Levine (2010). "Clomiphene citrate and testosterone gel replacement therapy for male hypogonadism: efficacy and treatment cost." *J Sex Med* 7(1 Pt 1): 269-276.

Tchernof, A., J. P. Després, et al. (1995). "Reduced testosterone and adrenal C19 steroid levels in obese men." *Metabolism* 44: 513-519.

Tchernof, A., F. Labrie, et al. (1996). "Obesity and metabolic complications: contribution of DHEA and other steroid hormones." *J. Endocrinol.* 150: S155-S164.

Tenover, J. S. (1992). "Effects of testosterone supplementation in the aging male." *J Clin Endocrinol Metab* 75(4): 1092-1098.

Tivesten, A., L. Vandenput, et al. (2009). "Low serum testosterone and estradiol predict mortality in elderly men." *J Clin Endocrinol Metab* 94(7): 2482-2488.

Traish, A. M., A. Guay, et al. (2009). "The dark side of testosterone deficiency: I. Metabolic syndrome and erectile dysfunction." *J Androl* 30(1): 10-22.

Traish, A. M., A. Haider, et al. (2013). "Long-term testosterone therapy in hypogonadal men ameliorates elements of the metabolic syndrome: an observational, long-term registry study." *Int J Clin Pract.*

Traish, A. M., H. P. Kang, et al. (2011). "Dehydroepiandrosterone (DHEA)—a precursor steroid or an active hormone in human physiology." *J Sex Med* 8(11): 2960-2982; quiz 2983.

Travison, T. G., J. E. Morley, et al. (2006). "The relationship between libido and testosterone levels in aging men." *J Clin Endocrinol Metab* 91(7): 2509-2513.

Trenell, M. I., N. S. Marshall, et al. (2007). "Sleep and metabolic control: waking to a problem?" *Clin Exp Pharmacol Physiol* 34(1-2): 1-9.

Turhan, S., C. Tulunay, et al. (2007). "The association between androgen levels and premature coronary artery disease in men." *Coron Artery Dis* 18(3): 159-162.

Ueno, S., M. Namiki, et al. (2006). "Efficacy of primary hormonal therapy for patients with localized and locally advanced prostate cancer: a retrospective multicenter study." *Int J Urol* 13(12): 1494-1500.

Valenti, G., L. Denti, et al. (2004). "Effect of DHEAS on skeletal muscle over the life span: the InCHIANTI study." *J Gerontol A Biol Sci Med Sci* 59(5): 466-472.

Vallee, M., W. Mayo, et al. (2001). "Role of pregnenolone, dehydroepiandrosterone and their sulfate esters on learning and memory in cognitive aging." *Brain Res Brain Res Rev* 37(1-3): 301-312.

Vermeulen, A. (2003). "Diagnosis of partial androgen deficiency in the aging male." *Ann Endocrinol (Paris)* 64(2): 109-114.

Vigen, R., C. I. O'Donnell, et al. (2013). "Association of testosterone therapy with mortality, myocardial infarction, and stroke in men with low testosterone levels." *Jama* 310(17): 1829-1836.

Villareal, D. T. and J. O. Holloszy (2004). "Effect of DHEA on abdominal fat and insulin action in elderly women and men: a randomized controlled trial." *JAMA* 292(18): 2243-2248.

Villareal, D. T., J. O. Holloszy, et al. (2000). "Effects of DHEA replacement on bone mineral density and body composition in elderly women and men." *Clin Endocrinol (Oxf)* 53(5): 561-568.

Wakeling, A. E. (1993). "The future of new pure antiestrogens in clinical breast cancer." *Breast Cancer Res. Treat.* 25: 1-9.

Wang, C., G. Cunningham, et al. (2004). "Long-term testosterone gel (AndroGel) treatment maintains beneficial effects on sexual function and mood, lean and fat mass, and bone mineral density in hypogonadal men." *J Clin Endocrinol Metab* 89(5): 2085-2098.

Wang, C., E. Nieschlag, et al. (2009a). "Investigation, treatment, and monitoring of late-onset hypogonadism in males: ISA, ISSAM, EAU, EAA, and ASA recommendations." *J Androl* 30(1): 1-9.

Wang, C., E. Nieschlag, et al. (2009b). "ISA, ISSAM, EAU, EAA and ASA recommendations: investigation, treatment and monitoring of late-onset hypogonadism in males." *Aging Male* 12(1): 5-12.

Wang, C., R. S. Swerdloff, et al. (2000). "Transdermal testosterone gel improves sexual function, mood, muscle strength, and body composition parameters in hypogonadal men." *J Clin Endocrinol Metab* 85(8): 2839-2853.

Weill-Engerer, S., J. P. David, et al. (2002). "Neurosteroid quantification in human brain regions: comparison between Alzheimer's and nondemented patients." *J Clin Endocrinol Metab* 87(11): 5138-5143.

Weinstein, R. S. and M. S. Hutson (1987). "Decreased trabecular width and increased trabecular spacing contribute to bone loss with aging." *Bone* 8: 137-142.

Whitten, S. J., A. K. Nangia, et al. (2006). "Select patients with hypogonadotropic hypogonadism may respond to treatment with clomiphene citrate." *Fertil Steril* 86(6): 1664-1668.

Williams, M. R., T. Dawood, et al. (2004). "Dehydroepiandrosterone increases endothelial cell proliferation in vitro and improves endothelial function in vivo by mechanisms independent of androgen and estrogen receptors." *J Clin Endocrinol Metab* 89(9): 4708-4715.

Wolkowitz, O. M., V. I. Reus, et al. (1999). "Double-blind treatment of major depression with dehydroepiandrosterone." *Am J Psychiatry* 156(4): 646-649.

Wu, F. C., A. Tajar, et al. (2010). "Identification of late-onset hypogonadism in middle-aged and elderly men." *N Engl J Med* 363(2): 123-135.

Wu, F. C. and A. von Eckardstein (2003). "Androgens and coronary artery disease." *Endocr Rev* 24(2): 183-217.

Xu, H., G. K. Gouras, et al. (1998). "Estrogen reduces neuronal generation of Alzheimer beta-amyloid peptides." *Nat Med* 4(4): 447-451.

Yaffe, K. (1998). "Estrogen therapy in postmenopausal women: effects on cognitive function and dementia." *JAMA* 279: 688-695.

Yau, J. L., S. Rasmuson, et al. (2003). "Dehydroepiandrosterone 7-hydroxylase CYP7B: predominant expression in primate hippocampus and reduced expression in Alzheimer's disease." *Neuroscience* 121(2): 307-314.

Yen, S. S., A. J. Morales, et al. (1995). "Replacement of DHEA in aging men and women. Potential remedial effects." *Ann. N.Y. Acad. Sci.* 774: 128-142.

Yen, T. T., J. A. Allan, et al. (1977). "Prevention of obesity in Avy/a mice by dehydroepiandrosterone." *Lipids* 12: 409-413.

Zitzmann, M. (2009). "Testosterone deficiency, insulin resistance and the metabolic syndrome." *Nat Rev Endocrinol* 5(12): 673-681.

Zitzmann, M., S. Faber, et al. (2006). "Association of specific symptoms and metabolic risks with serum testosterone in older men." *J Clin Endocrinol Metab* 91(11): 4335-4343.

What is claimed is:

1. A method of reducing the incidence of male androgen deficiency symptoms or diseases, said method comprising administering to an aging male patient in need of said reduction, wherein said aging male patient has functional adrenals and testis, (i) a therapeutically effective amount of a sex steroid precursor or prodrug thereof in association with (ii) a therapeutically effective amount of a selective estrogen receptor modulator or prodrug thereof, wherein the selective estrogen receptor modulator stimulates LH secretion which increases the level of circulating testosterone; wherein the selective estrogen receptor modulator is acolbifene:

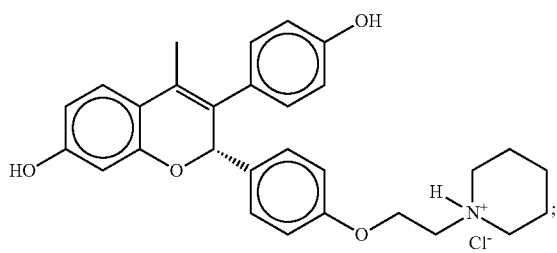

And is an optically active compound having an absolute configuration S on carbon 2; and wherein the sex steroid precursor is dehydroepiandrosterone.

2. The method of claim 1 wherein the symptoms or diseases are selected from the group comprising of loss of libido, erectile dysfunction, tiredness, loss of energy, depression, bone loss, muscle loss, muscle weakness, fat accumulation, memory loss, cognition loss, Alzheimer's disease, dementia, loss of body hair, fertility problems, insomnia, gynecomastia, anemia, hot flushes, sweats, decreased sense of well-being, obesity, osteoporosis, hypercholesterolemia, hyperlipidemia, atherosclerosis, hypertension, insulin resistance, cardiovascular disease and type 2 diabetes.

3. The method of claim 1, wherein the selective estrogen receptor modulator has no estrogenic activity in breast, uterine or endometrial tissues.

4. The method of claim 1 which reduces the risk of the male patients acquiring breast cancer.

5. The method of claim 1, further comprising administering as part of a combination therapy, a therapeutically effective amount of human chorionic gonadotropin.

6. The method of claim 1 wherein the selective estrogen receptor modulator and/or sex steroid precursor are/is rectally administered.

7. The method of claim 1 wherein the selective estrogen receptor modulator and/or sex steroid precursor are/is orally administered.

8. The method of claim 1 wherein the selective estrogen receptor modulator and/or sex steroid precursor are/is percutaneously administered.

9. The method of claim 2, wherein the symptom or disease is loss of libido.

10. The method of claim 2, wherein the symptom or disease is erectile dysfunction.

11. The method of claim 2 wherein the symptom or disease is tiredness.

12. The method of claim 2, wherein the symptom or disease is loss of energy.

13. The method of claim 2, wherein the symptom or disease is depression.

14. The method of claim 2, wherein the symptom or disease is bone loss.

15. The method of claim 2, wherein the symptom or disease is muscle loss.

16. The method of claim 2, wherein the symptom or disease is muscle weakness.

17. The method of claim 2, wherein the symptom or disease is fat accumulation.

18. The method of claim 2, wherein the symptom or disease is memory loss.

19. The method of claim 2, wherein the symptom or disease is cognition loss.

20. The method of claim 2, wherein the symptom or disease is Alzheimer's disease.

21. The method of claim 2, wherein the symptom or disease is dementia.

22. The method of claim 2, wherein the symptom or disease is loss of body hair.

23. The method of claim 2, wherein the symptom or disease is fertility problems.

24. The method of claim 2, wherein the symptom or disease is insomnia.

25. The method of claim 2, wherein the symptom or disease is gynecomastia.

26. The method of claim 2, wherein the symptom or disease is anemia.

27. The method of claim 2, wherein the symptom or disease is hot flushes.

28. The method of claim 2, wherein the symptom or disease is sweats.

29. The method of claim 2, wherein the symptom or disease is decreased sense of well-being.

30. The method of claim 2, wherein the symptom or disease is obesity.

31. The method of claim 2, wherein the symptom or disease is osteoporosis.

32. The method of claim 2, wherein the symptom or disease is hypercholesterolemia.

33. The method of claim 2, wherein the symptom or disease is hyperlipidemia.

34. The method of claim 2, wherein the symptom or disease is atherosclerosis.

35. The method of claim 2, wherein the symptom or disease is hypertension.

36. The method of claim 2, wherein the symptom or disease is insulin resistance.

37. The method of claim 2, wherein the symptom or disease is cardiovascular disease.

38. The method of claim 2, wherein the symptom or disease is type 2 diabetes.

39. The method of claim 1, wherein the male androgen deficiency symptoms or diseases are associated with male hypogonadism.

* * * * *